US008859550B2

(12) United States Patent
Chen et al.

(10) Patent No.: US 8,859,550 B2
(45) Date of Patent: *Oct. 14, 2014

(54) HETEROCYCLIC INHIBITORS OF HISTAMINE RECEPTORS FOR THE TREATMENT OF DISEASE

(75) Inventors: Pingyun Chen, Chapel Hill, NC (US); Stephen A. R. Carino, Del Mar, CA (US); Ricky Wayne Couch, Durham, NC (US); Daniel S. Kinder, Del Mar, CA (US); Beth A. Norton, Del Mar, CA (US)

(73) Assignee: Kalypsys, Inc., Del Mar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/606,947

(22) Filed: Sep. 7, 2012

(65) Prior Publication Data

US 2013/0245001 A1    Sep. 19, 2013

Related U.S. Application Data

(60) Provisional application No. 61/533,455, filed on Sep. 12, 2011.

(51) Int. Cl.
| | |
|---|---|
| *C07D 487/04* | (2006.01) |
| *A61K 9/00* | (2006.01) |
| *A61K 31/4985* | (2006.01) |
| *A61P 37/08* | (2006.01) |
| *C07C 309/04* | (2006.01) |
| *C07C 53/126* | (2006.01) |
| *C07C 55/10* | (2006.01) |
| *C07C 59/245* | (2006.01) |

(52) U.S. Cl.
CPC .......... *C07D 487/04* (2013.01); *C07C 309/04* (2013.01); *A61K 9/00* (2013.01); *C07C 53/126* (2013.01); *C07C 55/10* (2013.01); *C07C 59/245* (2013.01); *C70C 59/255* (2013.01); *C07B 2200/13* (2013.01)
USPC .......... 514/249; 544/350; 544/359; 548/953; 549/59

(58) Field of Classification Search
CPC ..... C07D 487/04; A61K 9/00; C07B 2200/13
USPC .................. 514/249; 544/350, 359; 548/953; 549/59
See application file for complete search history.

(56) References Cited

U.S. PATENT DOCUMENTS

| | | | | |
|---|---|---|---|---|
| 8,569,300 B2* | 10/2013 | Borchardt et al. | ............ | 514/249 |
| 2008/0139572 A1 | 6/2008 | Wang et al. | | |
| 2010/0120741 A1 | 5/2010 | Borchardt | | |
| 2010/0249142 A1 | 9/2010 | Deleuze-Masquefa et al. | | |
| 2011/0237565 A1* | 9/2011 | Borchardt et al. | ....... | 514/210.21 |
| 2011/0237599 A1 | 9/2011 | Borchardt | | |

FOREIGN PATENT DOCUMENTS

| | | |
|---|---|---|
| EP | 1972629 | 9/2008 |
| WO | 2004022060 A2 | 3/2004 |
| WO | 2008031556 A2 | 3/2008 |
| WO | 2009089547 A1 | 7/2009 |
| WO | 2009098320 A2 | 8/2009 |
| WO | 2010030785 A2 | 3/2010 |
| WO | 2011112687 A1 | 3/2011 |
| WO | 2011075591 A1 | 6/2011 |
| WO | 2011089400 A1 | 7/2011 |

OTHER PUBLICATIONS

Khankari et al. Thermochimica Acta 1995, 248, 61-79.*
Conalty, M.L. et akl., "Anticancer agents—XII. Pyridazine and Benzodiazine derivatives," Proceedings of the Royal Irish Academy, Section B: Biological, Geological and Chemical Science (1976), 76(10), 151-63.
Kim, HS et al., "Synthesis of tetrazolo[1,5-a]quinoxalines with antimicrobial activity," Journal of the Korean Chemical Society (2001), 45(4), 325-333.
Smits R. A. et al., "Major advances in the developments of histamine H4 receptor ligands," Drug Discovery Today, vol. 14, No. 15/16, Aug. 2009.
Beres M. et al., "Ring Opening of [1,2,3]Triazolo[1,5-alpha]pyrazinium Salts: Synthesis and Some Transformations of a Novel Type of 2-Aza-1,3-butadienes," Tetrahedron 53 (1997) 27, 9393-9400.
Makata S. et al., "Reduction of 4, 7-Diphenyl-1,2,5-thia(oxa)diazolo[3,4-c]pyridines Affording 2,5-Diphenyl-3,4-diaminopyridines and Ring Closure of the Diamines to Fluorescent Azaheterocycles," Journal of Heterocyclic Chemistry vol. 19, Issue 6, pp. 1481-1488, 1982.
Paparin JL et al., "Synthesis of 2,5-bis-Arylpyridines by [4 + 2] Cycloaddition of 1,4-bisAryl-2-aza-1,3-butadienes with Electron-Poor Dienophiles," J. Heterocyclic Chem. 37, 411 (2000).
Tetrazolopyrazines Registry Records Not Indexed in CAS subset from STN (accessed approx. Jul. 20, 2009).
WO2010030785A2 Int'l Search Report, May 10, 2010.
WO2010030785A2 Written Opinion of the Int'l Searching Authority, May 10, 2010.
WO2010030785A2 Int'l Preliminary Report on Patentability, Mar. 24, 2011.
EP2324029 Extended European Search Report, Aug. 17, 2011.
Sarges R. et al., "4-Amino[ 1,2,4]triazolo[4,3-a Iquinoxalines. A Novel Class of Potent Adenosine Receptor Antagonists and Potential Rapid-Onset Antidepressants," Journal of Medicinal Chemistry (1990), 33(8), 2240-54.

(Continued)

*Primary Examiner* — Sreeni Padmanabhan
*Assistant Examiner* — Irina Neagu
(74) *Attorney, Agent, or Firm* — Dennis A. Bennett; Cynthia Hathaway

(57) ABSTRACT

The present invention relates to salts, hydrates, and polymorphs of bicyclic heteroaryl compounds, and pharmaceutical compositions thereof, which may be useful as inhibitors of $H_4R$ for the treatment or prevention of diseases including allergic rhinitis.

59 Claims, 32 Drawing Sheets

(56) References Cited

OTHER PUBLICATIONS

Nagarajan K et al., "Displacement reactions of 2,3-dichloro-6-nitroquinoxaline: Synthesis of s-Triazolo[3,4-a]quinoxaline," Indian Journal of Chemistry, Section B: Organic Chemistry Including Medicinal Chemistry (1986), 25B(7), 739-40.

Badran MM et al., "Part I: Novel quinoxaline derivatives of biological interest," Bulletin of Pharmaceutical Sciences, Assiut University (2001), 24(2), 135-144.

Campiani G. et al., "Pyrroloquinoxaline Derivatives as High-Affinity and Selective 5-HT3 Receptor Agonists: Synthesis, Further Structure-Activity Relationships, and Biological Studies," J. Med. Chem. 1999, 42, 4362-4379.

EP11754043 Extended European Search Report, Jun. 20, 2013.

WO2011112687 International Search Report and Written Opinion of the Int'l Searching Authority, Nov. 25, 2011.

WO2011112766 International Search Report and Written Opinion of the Int'l Searching Authority, Nov. 25, 2011.

Non-final rejection dated Jan. 2, 2013 in U.S. Appl. No. 13/044,661, filed Mar. 10, 2011 (publ. No. US2011/0237565A1, now patent No. 8,569,300).

* cited by examiner

HETEROCYCLIC INHIBITORS OF HISTAMINE RECEPTORS FOR THE TREATMENT OF DISEASE

This application claims the benefit of priority of U.S. provisional Application No. 61/533,455, filed Sep. 12, 2011, the contents of which are hereby incorporated by reference as if written herein in its entirety.

Disclosed herein are new compounds, and salts, hydrates, and polymorphs thereof, of heterocyclic compounds, as well as compositions comprising them, and their application as pharmaceuticals for the treatment of disease.

Histamine, a low molecular weight biogenic amine, is a potent chemical mediator of normal and pathological physiology. Histamine functions as a secreted signal in immune and inflammatory responses, as well as a neurotransmitter. The functions of histamine are mediated through four distinct cell surface receptors ($H_1R$, $H_2R$, $H_3R$ and $H_4R$). Histamine receptors vary in expression, signaling, function and histamine affinity, and therefore have different potential therapeutic applications (Zhang M, Thurmond R L, and Dunford P J *Pharmacology & Therapeutics*. 2007).

All four histamine receptors are G protein-coupled receptors (GPCRs). Upon histamine or other agonist binding, they activate distinct signaling pathways through different heterotrimeric G proteins. The $H_1R$ couples to the $G_q$ family of G proteins, whose primary signaling cascade induces second messenger calcium mobilization from intracellular stores, followed by multiple downstream effects. $H_1R$ can also increase cyclic GMP (cGMP) production and activate NFκB, a potent, positive transcriptional regulator of inflammation. The $H_2R$ couples to the $G_s$ family of G proteins and increases cyclic AMP (cAMP) formation by stimulating adenylate cyclase, although it can also induce calcium mobilization in some cell types. The $H_3R$ mediates its function through $G_{i/o}$ proteins and decreases cAMP formation by inhibiting adenylate cyclase. Like other $G_{i/o}$-coupled receptors, $H_3R$ also activates the mitogen-activated protein/extracellular-signal regulated protein (MAP/ERK) kinase pathway. $H_4R$ has also been demonstrated to couple to $G_{i/o}$ proteins, with canonical inhibition of cAMP formation and MAP kinase activation. However, $H_4R$ also couples to calcium mobilization in certain cell types. In fact, $H_4R$ signaling in mast cells is primarily through calcium mobilization with little to no impact on cAMP formation.

The $H_1R$ is expressed in many cell types, including endothelial cells, most smooth muscle cells, cardiac muscle, central nervous system (CNS) neurons, and lymphocytes. $H_1R$ signaling causes smooth muscle contraction (including bronchoconstriction), vasodilation, and increased vascular permeability, hallmarks of allergic and other immediate hypersensitivity reactions. In the CNS, $H_1R$ activation is associated with wakefulness. Its activation is also associated with pruritus and nociception in skin and mucosal tissues. For many years, the anti-allergic and anti-inflammatory activities of $H_1R$ antagonists have been utilized to treat acute and chronic allergic disorders and other histamine-mediated pathologies, such as itch and hives.

The $H_2R$ is expressed similarly to the $H_1R$, and can also be found in gastric parietal cells and neutrophils. $H_2R$ is best known for its central role in gastric acid secretion but has also been reported to be involved in increased vascular permeability and airway mucus production. Antagonists of $H_2R$ are widely used in treating peptic ulcers and gastroesophageal reflux disease. These drugs are also used extensively to reduce the risk of gastrointestinal (GI) bleeding associated with severe upper GI ulcers and GI stress in the inpatient setting.

The $H_3R$ is primarily found in the CNS and peripheral nerves innervating cardiac, bronchial, and GI tissue. $H_3R$ signaling regulates the release of multiple neurotransmitters, such as acetylcholine, dopamine, serotonin, and histamine itself (where it acts as a CNS autoreceptor). In the CNS, $H_3R$ participates in the processes of cognition, memory, sleep, and feeding behaviors. $H_3R$ antagonists may be used potentially for treating cognition disorders (such as Alzheimer's disease), sleep and wakefulness disorders, attention disorders, and metabolic disorders (especially related to obesity).

Existence of the $H_4R$ was predicted in the early 1990s, but its cloning by multiple groups was not reported until 2000. In contrast to the other histamine receptors, the $H_4R$ has a distinctly selective expression profile in bone marrow and on certain types of hematopoietic cells. $H_4R$ signaling modulates the function of mast cells, eosinophils, dendritic cells, and subsets of T cells. The $H_4R$ appears to control multiple behaviors of these cells, such as activation, migration, and cytokine and chemokine production (Zhang M, Thurmond R L, and Dunford P J *Pharmacology & Therapeutics*. 2007).

Of the 4 known histamine receptors, $H_1R$, $H_2R$ and $H_4R$ have been shown clearly to affect inflammation and other immune responses and are proposed therapeutic targets for treating immune and inflammatory disorders (Jutel et al., 2002; Akdis & Simons, 2006). The $H_1R$ was the first described histamine receptor, and ligands targeting this receptor were initially developed in the 1930s and in widespread use by the 1940s. Common $H_1R$ antagonist drugs currently approved for use include systemic agents such as diphenhydramine (Benadryl, also used topically), cetirizine (Zyrtec), fexofenadine (Allegra), loratadine (Claritin) and desloratadine (Clarinex), and topical agents such as olopatadine (Patanol, Pataday, Patanase), ketotifen, azelastine (Optivar, Astelin) and epinastine (Elestat). Traditional uses have included allergic diseases and reactions such as asthma, rhinitis, and other chronic obstructive pulmonary disorders, ocular disorders such as allergic conjunctivitis, and pruritus of varying etiologies.

However, $H_1$ receptor antagonists have certain deficiencies as therapeutic agents in the treatment of diseases where histamine is an important mediator. First, their effects are often only moderate and reduce allergic symptoms by only 40 to 50%. In particular, $H_1$ receptor antagonists, especially systemic agents, have little to no effect in relieving nasal congestion. In allergic asthma, despite the fact that histamine levels rapidly increase in the airways and in plasma (correlating with disease severity), $H_1$ receptor antagonists have largely failed as a therapeutic strategy, though some effect is seen with administration during the priming phase as opposed to the challenge phase (Thurmond R L et al., *Nat Rev Drug Discov*, 2008, 7:41-53). Additionally, although the efficacy of $H_1$ receptor antagonists against pruritus in acute urticarias, associated with hives and insect stings, and in chronic idiopathic urticaria is well proven, $H_1R$ antagonists are mostly ineffective in the treatment of atopic dermatitis-associated pruritus, with the only modest benefits derived from some first-generation compounds likely a consequence of their sedative properties (Sharpe, G. R. & Shuster, S. *Br. J Dermatol*. 1993, 129:575-9). Finally, sedation caused by $H_1R$ antagonists that cross the blood-brain barrier, among other side effects, limits the utility of many $H_1R$ antagonists in diseases for which they would otherwise be efficacious. These deficiencies render $H_1R$ antagonists amenable to replacement by or supplementation with other agents.

Consequently, attention has focused on the more recently discovered $H_4$ receptor as a therapeutic target. Given the ability of $H_4R$ to modulate the cellular function of eosinophils, mast cells, dendritic cells and T cells (M. Zhang et al., *Pharmacol Ther* 2007), it is natural to speculate that the $H_4R$ may be involved in various inflammatory diseases, and that $H_4R$ antagonists would have therapeutic potential (Jutel et al., 2006). Indeed, both in vitro and in vivo evidence has been demonstrated for the utility of $H_4R$ antagonists as anti-inflammatory agents in inflammatory bowel disease (IBD) (Sander L E et al., *Gut* 2006; 55:498-504). The finding that $H_4$ receptor antagonists inhibit histamine-induced migration of mast cells and eosinophils in vitro and in vivo, both of which are important effector cells in the allergic response, raises the possibility that this class of compounds could reduce the allergic hyper-responsiveness developed upon repeated exposure to antigens, which is characterized by an increase in the number of mast cells and other inflammatory cells in the nasal and bronchial mucosa (Fung-Leung W P et al., *Curr Opin Inves Drugs*, 2004 5:11 1174-1182). In contrast to some of the $H_1R$ antagonists, $H_4R$ antagonists given during the allergen challenge phase of a mouse model of asthma are equally effective to those given during sensitization (Thurmond R L et al., *Nat Rev Drug Discov*, 2008, 7:41-53). In two recent mouse studies, a selective $H_4R$ agonist was shown to induce itch, whereas these responses, and those of histamine, were blocked by pretreatment with $H_4R$ antagonists. Similarly, histamine or $H_4$ receptor agonist-induced itch was markedly attenuated in $H_4$ receptor-deficient animals (Dunford, P. J. et al., *J. Allergy Clin. Immunol*, 2007, 119:176-183). The presence of the $H_4R$ in nasal tissue was first discovered by Nakaya et al. (Nakaya, M. et al., *Ann Otol Rhinol Laryngol*, 2004, 113: 552-557). In addition, a more recent finding showed that there is a significant increase in the level of $H_4R$ in human nasal polyp tissue taken from patients with chronic rhinosinusitis (infection of the nose and nasal cavities) when compared to normal nasal mucosa. Jókúti et al. suggest that the administration of $H_4R$ antagonists might be a new way to treat nasal polyps and chronic rhinosinusitis. The administration of $H_4R$ antagonists may prevent the accumulation of eosinophils as a result of impaired cell chemotaxis toward polypous tissue (Jókúti, A. et al., *Cell Biol Int*, 2007, 31: 1367). Although scientific data on the role of the $H_4R$ in rhinitis is limited, at present, it is the only indication for which an $H_4R$ inverse agonist (CZC-13788) is reported to be in preclinical development (Hale, R. A. et al., *Drug News Perspect*, 2007, 20: 593-600).

Additional reports have shown potential for $H_4R$ antagonists in the treatment of metabolic disorders such as obesity (Jorgensen E et al., *Neuroendocrinology*. 2007; 86(3):210-4), vascular or cardiovascular diseases such as atherosclerosis (Tanihide A et al., *TCM* 2006: 16(8): 280-4), inflammation and pain (Coruzzi G et al., *Eur J Pharmacol*. 2007 Jun. 1; 563(1-3):240-4), rheumatoid arthritis (Grzybowska-Kowalczyk A et al., *Inflamm Res*. 2007 April; 56 Suppl 1:S59-60) and other inflammatory and autoimmune diseases including systemic lupus erythematosus (Zhang M, Thurmond R L, and Dunford P J *Pharmacology & Therapeutics*. 2007). What is clear is that a need still exists in the art for improved and varied antihistamines for the treatment of disease, and that compounds with $H_4R$ antagonist activity may fill this need.

At least some selective $H_4R$ antagonists have been previously disclosed. Nevertheless, a need still exists for compounds with $H_4R$ antagonist activity which have properties making them suitable for development as drugs, such as the ability to be isolated in a solid (preferably crystalline) form and appropriate solubility for formulation and delivery, for example in a tablet or capsule, or alternatively as a solution for intranasal delivery, for the treatment of allergic disorders.

Novel salts and polymorphs of compounds which have been found to inhibit the histamine type-4 receptor ($H_4R$) are herein disclosed, together with pharmaceutical compositions comprising them, methods of synthesizing, characterizing, and using the salts and polymorphs including methods for the treatment of histamine receptor-mediated diseases in a patient by administering the salts and polymorphs.

Provided herein are salts and polymorphs which comprise compounds of structural Formula (I) together with a counterion:

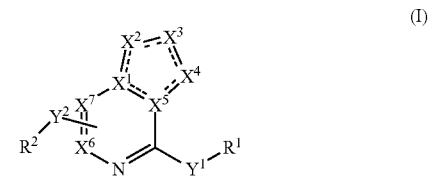

wherein:

the ring comprising $X^1$-$X^5$ is aromatic;

$X^1$ and $X^5$ are independently chosen from C, CH and N;

$X^2$ is chosen from $[C(R^6)(R^7)]$, $NR^8$, O and S;

$X^3$ is chosen from)$[C(R^9)(R^{10})]$, $NR^{11}$, O, and S;

$X^4$ is chosen from $[C(R^{12})(R^{13})]$, $NR^{14}$, O and S;

$X^6$ is chosen from $CR^{18}$ and N;

$X^7$ is chosen from $CR^{19}$ and N;

$Y^1$ is chosen from a bond, lower alkyl, lower alkoxy, $OR^{15}$, $NR^{16}R^{17}$, and lower aminoalkyl;

$Y^2$ is chosen from a bond, lower alkyl, lower alkoxy, $OR^{20}$, $NR^{21}R^{22}$, S, $C(O)NH_2$, $C(O)NHR_{23}$, $C(O)NR_{23}R_{24}$ and lower aminoalkyl;

$R^1$ is selected from the group consisting of:

aryl, heterocycloalkyl, cycloalkyl, and heteroaryl, any of which may be optionally substituted, when $Y^1$ is a bond; and null, when $Y^1$ is chosen from $OR^{15}$, $NR^{16}R^{17}$, lower alkyl, lower alkoxy, or lower aminoalkyl;

$R^2$ is chosen from alkyl, alkenyl, alkynyl, aryl, cycloalkyl, heterocycloalkyl, and heteroaryl, any of which may be optionally substituted;

$R^6$, $R^7$, $R^9$, $R^{10}$, $R^{12}$, $R^{13}$, $R^{18}$, and $R^{19}$ are independently chosen from null, hydrogen, alkyl, alkenyl, alkynyl, heteroalkyl, alkoxy, halogen, haloalkyl, perhaloalkyl, amino, aminoalkyl, amido, carboxyl, acyl, hydroxy, cyano, nitro, aryl, arylalkyl, cycloalkyl, cycloalkylalkyl, heterocycloalkyl, heterocycloalkylalkyl, heteroaryl, and heteroarylalkyl, any of which may be optionally substituted;

$R^8$, $R^{11}$, and $R^{14}$ are independently chosen from null, hydrogen, alkyl, heteroalkyl, alkoxy, haloalkyl, perhaloalkyl, aminoalkyl, C-amido, carboxyl, acyl, hydroxy, aryl, arylalkyl, cycloalkyl, cycloalkylalkyl, heterocycloalkyl, heterocycloalkylalkyl, heteroaryl, and heteroarylalkyl, any of which may be optionally substituted;

$R^{15}$, $R^{16}$, $R^{20}$, and $R^{21}$ are independently chosen from aminoalkyl, alkylaminoalkyl, aryl, arylalkyl, cycloalkyl, cycloalkylalkyl, ether, heterocycloalkyl, lower alkylaminoheterocycloalkyl, heterocycloalkylalkyl, heteroaryl, and heteroarylalkyl, any of which may be optionally substituted;

$R^{17}$ and $R^{22}$ are independently chosen from hydrogen, aminoalkyl, alkylaminoalkyl aryl, arylalkyl, cycloalkyl, cycloalkylalkyl, ether, heterocycloalkyl, lower alkylaminoheterocycloalkyl, heterocycloalkylalkyl, heteroaryl, and heteroarylalkyl, any of which may be optionally substituted; and $R_{23}$ and $R_{24}$ are independently chosen from hydrogen, alkyl, alkenyl, alkynyl, heteroalkyl, alkoxy, halogen, haloalkyl, perhaloalkyl, perhaloalkoxy, amino, aminoalkyl, amido, carboxyl, acyl, hydroxy, cyano, nitro, aryl, arylalkyl, cycloalkyl, cycloalkylalkyl, heterocycloalkyl, heterocycloalkylalkyl, heteroaryl, and heteroarylalkyl, any of which may be optionally substituted.

Salts and polymorphs disclosed herein may possess useful histamine receptor inhibitory activity, and may be used in the treatment or prophylaxis of a disease or condition in which $H_4R$ plays an active role. Thus, in broad aspect, certain embodiments also provide pharmaceutical compositions comprising one or more compounds, salts, hydrates, or polymorphs disclosed herein together with a pharmaceutically acceptable carrier, as well as methods of making and using the compounds and compositions. Certain embodiments provide methods for inhibiting $H_4R$. Other embodiments provide methods for treating an $H_4R$-mediated disorder in a patient in need of such treatment, comprising administering to said patient a therapeutically effective amount of a compound, salt, hydrate, or polymorph or a composition comprising it. Also provided is the use of certain compounds, salts, hydrates, or polymorphs disclosed herein for use in the manufacture of medicaments for the treatment of a disease or condition ameliorated by the inhibition of $H_4R$.

BRIEF DESCRIPTION OF THE DRAWINGS

FIG. 4: GVS Isotherm Plot of 8-(4-Methylpiperazin-1-yl)-5-(thiophen-2-yl)tetrazolo[1,5-a]pyrazine Tartrate Hemihydrate Form 1, also known as Compound 1, Tartrate Salt, Form 1. In the figure legend, "Cycle 1 S" means Cycle 1 Sorption, "Cycle 1 DS" means Cycle 1 Desorption, and so on.

Figure 1:
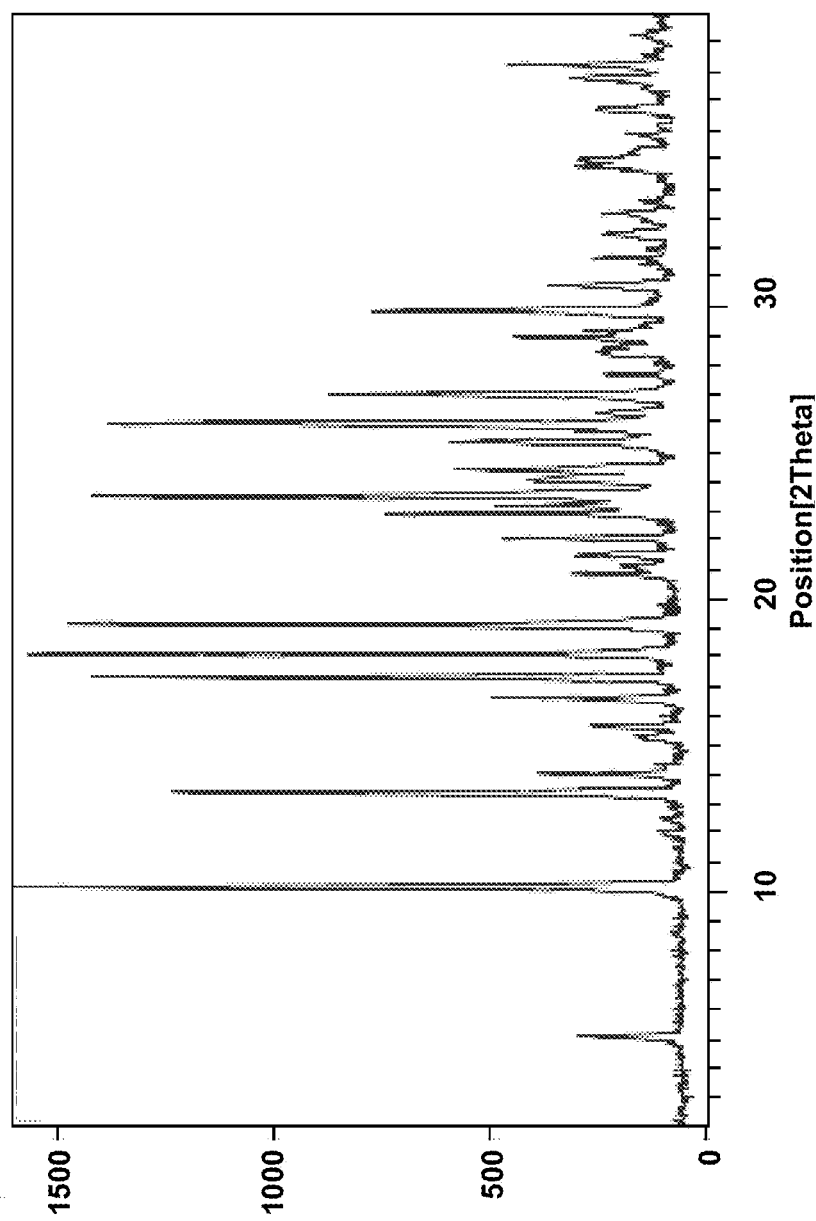
FIG. 1: PXRD diffractogram of 8-(4-Methylpiperazin-1-yl)-5-(thiophen-2-yl)tetrazolo[1,5-a]pyrazine Tartrate Hemihydrate Form 1 also known as Compound 1 Tartrate Salt Form 1.

In certain embodiments, compounds, salts, hydrates, and polymorphs of compounds disclosed herein are solid.

In further embodiments, compounds, salts, hydrates, and polymorphs of compounds disclosed herein are crystalline.

In certain embodiments provided herein, at least two of $X^1$-$X^7$ are ring heteroatoms.

In certain embodiments provided herein,
$X^7$ is N;
$X^6$ is $CR^{18}$; and
$Y^1$ and $Y^2$ are each independently a bond.

Also provided herein are salts and polymorphs which comprise compounds of structural Formula (II) together with a counterion

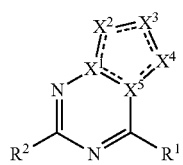

(II)

wherein:
$X^1$ and $X^5$ are independently chosen from C and N;
$X^2$ is chosen from $[C(R^6)(R^7)]$, and $NR^8$;
$X^3$ is chosen from $[C(R^9)(R^{10})]$, and $NR^{11}$;
$X^4$ is chosen from $[C(R^{12})(R^{13})]$, and $NR^{14}$;
$R^1$ is chosen from aryl, heterocycloalkyl, cycloalkyl, and heteroaryl, any of which may be optionally substituted;
$R^2$ is chosen from alkyl, alkenyl, alkynyl, aryl, cycloalkyl, heterocycloalkyl and heteroaryl, any of which may be optionally substituted;
$R^6$, $R^7$, $R^9$, $R^{10}$, $R^{12}$, and $R^{13}$ are independently chosen from null, hydrogen, alkyl, alkenyl, alkynyl, heteroalkyl, alkoxy, halogen, haloalkyl, perhaloalkyl, amino, aminoalkyl, amido, carboxyl, acyl, hydroxy, cyano, nitro, aryl, arylalkyl, cycloalkyl, cycloalkylalkyl, heterocycloalkyl, heterocycloalkylalkyl, heteroaryl, and heteroarylalkyl, any of which may be optionally substituted; and
$R^8$, $R^{11}$, and $R^{14}$ are independently chosen from null, hydrogen, alkyl, heteroalkyl, alkoxy, haloalkyl, perhaloalkyl, aminoalkyl, C-amido, carboxyl, acyl, hydroxy, aryl, arylalkyl, cycloalkyl, cycloalkylalkyl, heterocycloalkyl, heterocycloalkylalkyl, heteroaryl, and heteroarylalkyl, any of which may be optionally substituted.

In certain embodiments provided herein,
$X^7$ is $CR^{19}$;
$X^6$ is N; and
$Y^1$ and $Y^2$ are each independently a bond.

Also provided herein are salts and polymorphs which comprise compounds of structural Formula (III) together with a counterion

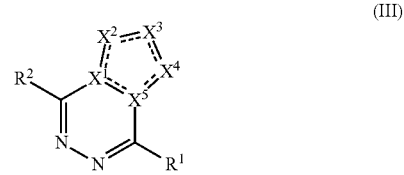

(III)

wherein:
$X^1$ and $X^5$ are independently chosen from C and N;
$X^2$ is chosen from $[C(R^6)(R^7)]$, and $NR^8$;
$X^3$ is chosen from $[C(R^9)(R^{10})]$, and $NR^{11}$;
$X^4$ is chosen from $[C(R^{12})(R^{13})]$, and $NR^{14}$;
$R^1$ is chosen from aryl, heterocycloalkyl, cycloalkyl, and heteroaryl, any of which may be optionally substituted;
$R^2$ is chosen from alkyl, alkenyl, alkynyl, aryl, cycloalkyl, heterocycloalkyl and heteroaryl, any of which may be optionally substituted;
$R^6$, $R^7$, $R^9$, $R^{10}$, $R^{12}$, and $R^{13}$ are independently chosen from null, hydrogen, alkyl, alkenyl, alkynyl, heteroalkyl, alkoxy, halogen, haloalkyl, perhaloalkyl, amino, aminoalkyl, amido, carboxyl, acyl, hydroxy, cyano, nitro, aryl, arylalkyl, cycloalkyl, cycloalkylalkyl, heterocycloalkyl, heterocycloalkylalkyl, heteroaryl, and heteroarylalkyl, any of which may be optionally substituted; and
$R^8$, $R^{11}$, and $R^{14}$ are independently chosen from null, hydrogen, alkyl, heteroalkyl, alkoxy, haloalkyl, perhaloalkyl, aminoalkyl, C-amido, carboxyl, acyl, hydroxy, aryl, arylalkyl, cycloalkyl, cycloalkylalkyl, heterocycloalkyl, heterocycloalkylalkyl, heteroaryl, and heteroarylalkyl, any of which may be optionally substituted.

In certain embodiments,
$X^7$ is $CR^{19}$;
$X^6$ is $CR^{18}$; and
$Y^1$ and $Y^2$ are each independently a bond.

Also provided herein are salts and polymorphs which comprise compounds of structural Formula (IV) together with a counterion

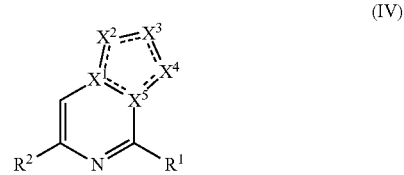

(IV)

wherein:

X¹ and X⁵ are independently chosen from C and N;

X² is chosen from [C(R⁶)(R⁷)], and NR⁸;

X³ is chosen from [C(R⁹)(R¹⁰)], and NR¹¹;

X⁴ is chosen from [C(R¹²)(R¹³)], and NR¹⁴;

R¹ is chosen from aryl, heterocycloalkyl, cycloalkyl, and heteroaryl, any of which may be optionally substituted;

R² is chosen from alkyl, alkenyl, alkynyl, aryl, cycloalkyl, heterocycloalkyl and heteroaryl, any of which may be optionally substituted;

R⁶, R⁷, R⁹, R¹⁰, R¹², and R¹³ are independently chosen from null, hydrogen, alkyl, alkenyl, alkynyl, heteroalkyl, alkoxy, halogen, haloalkyl, perhaloalkyl, amino, aminoalkyl, amido, carboxyl, acyl, hydroxy, cyano, nitro, aryl, arylalkyl, cycloalkyl, cycloalkylalkyl, heterocycloalkyl, heterocycloalkylalkyl, heteroaryl, and heteroarylalkyl, any of which may be optionally substituted; and R⁸, R¹¹, and R¹⁴ are independently chosen from null, hydrogen, alkyl, heteroalkyl, alkoxy, haloalkyl, perhaloalkyl, aminoalkyl, C-amido, carboxyl, acyl, hydroxy, aryl, arylalkyl, cycloalkyl, cycloalkylalkyl, heterocycloalkyl, heterocycloalkylalkyl, heteroaryl, and heteroarylalkyl, any of which may be optionally substituted.

In certain embodiments,

X³ is chosen from)[C(R⁹)(R¹⁰)], and NR¹¹;

R¹⁰ is chosen from null, hydrogen, and lower alkyl; and

R¹⁸ and R¹⁹ independently chosen from null, lower alkyl, and hydrogen.

Also provided herein are salts and polymorphs which comprise compounds of structural Formula (V) together with a counterion

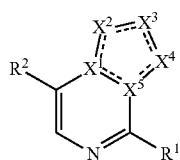

(V)

wherein:

X¹ and X⁵ are independently chosen from C and N;

X² is chosen from [C(R⁶)(R⁷)], and NR⁸;

X³ is chosen from)[C(R⁹)(R¹⁰)], and NR¹¹;

X⁴ is chosen from [C(R¹²)(R¹³)], and NR¹⁴;

R¹ is chosen from aryl, heterocycloalkyl, cycloalkyl, and heteroaryl, any of which may be optionally substituted;

R² is chosen from alkyl, alkenyl, alkynyl, aryl, cycloalkyl, heterocycloalkyl and heteroaryl, any of which may be optionally substituted;

R⁶, R⁷, R⁹, R¹⁰, R¹², and R¹³ are independently chosen from null, hydrogen, alkyl, alkenyl, alkynyl, heteroalkyl, alkoxy, halogen, haloalkyl, perhaloalkyl, amino, aminoalkyl, amido, carboxyl, acyl, hydroxy, cyano, nitro, aryl, arylalkyl, cycloalkyl, cycloalkylalkyl, heterocycloalkyl, heterocycloalkylalkyl, heteroaryl, and heteroarylalkyl, any of which may be optionally substituted; and R⁸, R¹¹, and R¹⁴ are independently chosen from null, hydrogen, alkyl, heteroalkyl, alkoxy, haloalkyl, perhaloalkyl, aminoalkyl, C-amido, carboxyl, acyl, hydroxy, aryl, arylalkyl, cycloalkyl, cycloalkylalkyl, heterocycloalkyl, heterocycloalkylalkyl, heteroaryl, and heteroarylalkyl, any of which may be optionally substituted.

In certain embodiments, compounds have structural formula (Va):

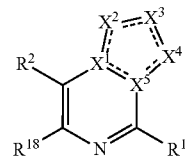

(Va)

wherein:

X¹ and X⁵ are independently chosen from C and N;

X² is chosen from [C(R⁶)(R⁷)], NR⁸, O and S;

X³ is chosen from)[C(R⁹)(R¹⁰)], and NR¹¹;

X⁴ is chosen from [C(R¹²)(R¹³)], NR¹⁴, O and S;

R¹ is chosen from aryl, heterocycloalkyl, cycloalkyl, and heteroaryl, any of which may be optionally substituted;

R² is chosen from aryl, cycloalkyl, heterocycloalkyl, and heteroaryl, any of which may be optionally substituted;

R⁶, R⁷, R⁹, R¹², and R¹³ are independently chosen from null, hydrogen, alkyl, alkynyl, heteroalkyl, alkoxy, halogen, haloalkyl, perhaloalkyl, amino, aminoalkyl, amido, carboxyl, acyl, hydroxy, cyano, nitro, aryl, arylalkyl, cycloalkyl, cycloalkylalkyl, heterocycloalkyl, heterocycloalkylalkyl, heteroaryl, and heteroarylalkyl, any of which may be optionally substituted;

R¹⁰ is chosen from null, hydrogen, and lower alkyl;

R⁸, R¹¹, and R¹⁴ are independently chosen from null, hydrogen, alkyl, heteroalkyl, alkoxy, haloalkyl, perhaloalkyl, aminoalkyl, C-amido, carboxyl, acyl, hydroxy, aryl, arylalkyl, cycloalkyl, cycloalkylalkyl, heterocycloalkyl, heterocycloalkylalkyl, heteroaryl, and heteroarylalkyl, any of which may be optionally substituted; and R¹⁸ is chosen from lower alkyl and hydrogen.

In certain embodiments:

R¹ is chosen from phenyl, monocyclic 4- to 7-membered heterocycloalkyl, monocyclic 4- to 7-membered cycloalkyl, and monocyclic 5- to 6-membered heteroaryl, any of which may be optionally substituted;

R² is chosen from phenyl, monocyclic 5- to 7-membered cycloalkyl, monocyclic 5- to 7-membered heterocycloalkyl, monocyclic 5- to 6-membered heteroaryl, and heteroarylalkyl any of which may be optionally substituted.

In certain embodiments, R⁶, R⁸, R¹¹, R¹², R¹³, and R¹⁴ are independently chosen from null and hydrogen.

In certain embodiments, compounds of Formula I have a structure chosen from:

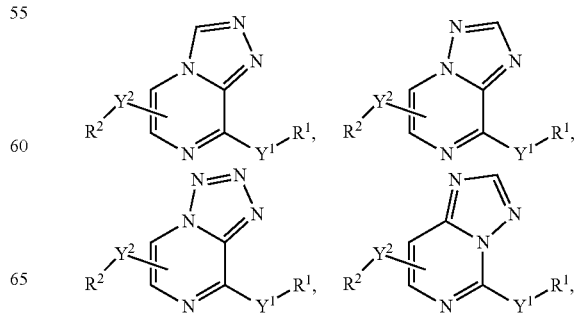

-continued

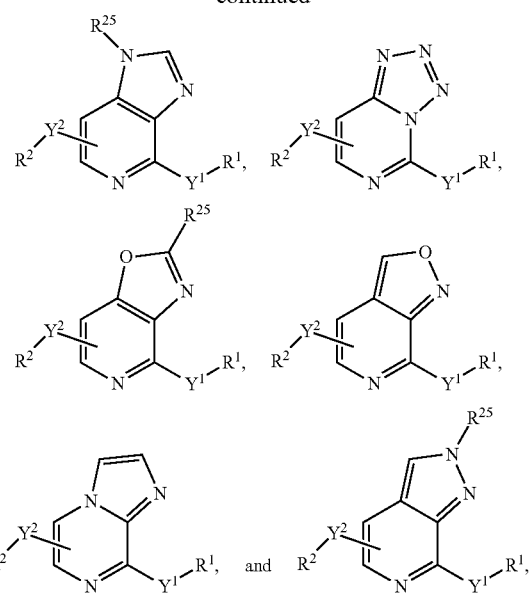

wherein:

R²⁵ is chosen from hydrogen, alkyl, alkenyl, alkynyl, heteroalkyl, alkoxy, halogen, haloalkyl, perhaloalkyl, perhaloalkoxy, amino, aminoalkyl, amido, carboxyl, acyl, hydroxy, cyano, nitro, aryl, arylalkyl, cycloalkyl, cycloalkylalkyl, heterocycloalkyl, heterocycloalkylalkyl, heteroaryl, and heteroarylalkyl, any of which may be optionally substituted; and all other groups are as disclosed in Formula I.

In certain embodiments, compounds of Formula I have a structure chosen from:

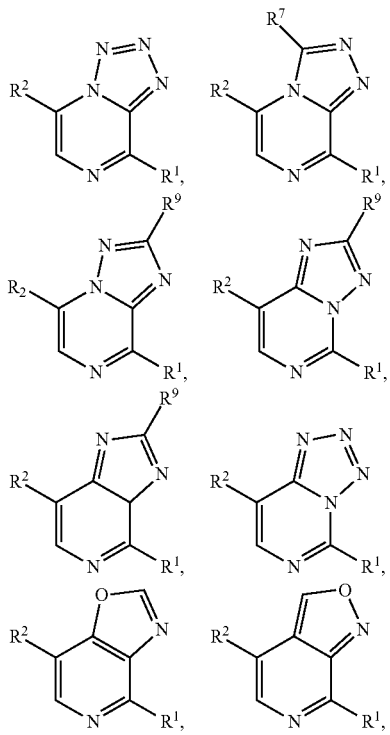

-continued

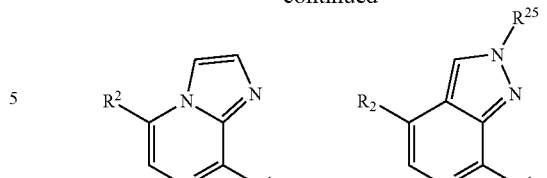

wherein:

R¹ is chosen from phenyl, monocyclic 4- to 7-membered heterocycloalkyl, monocyclic 4- to 7-membered cycloalkyl, and monocyclic 5- to 6-membered heteroaryl, any of which may be optionally substituted;

R² is chosen from alkyl, monocyclic cycloalkyl, monocyclic heterocycloalkyl and monocyclic heteroaryl, any of which may be optionally substituted;

R⁷ and R⁹ are independently chosen from null, hydrogen, alkyl, alkynyl, heteroalkyl, alkoxy, halogen, haloalkyl, perhaloalkyl, amino, aminoalkyl, amido, carboxyl, acyl, hydroxy, cyano, nitro, aryl, arylalkyl, cycloalkyl, cycloalkylalkyl, heterocycloalkyl, heterocycloalkylalkyl, heteroaryl, and heteroarylalkyl, any of which may be optionally substituted; and R²⁵ is chosen from hydrogen, alkyl, alkenyl, alkynyl, heteroalkyl, alkoxy, halogen, haloalkyl, perhaloalkyl, perhaloalkoxy, amino, aminoalkyl, amido, carboxyl, acyl, hydroxy, cyano, nitro, aryl, arylalkyl, cycloalkyl, cycloalkylalkyl, heterocycloalkyl, heterocycloalkylalkyl, heteroaryl, and heteroarylalkyl, any of which may be optionally substituted.

In certain embodiments, compounds of Formula I have a structure chosen from:

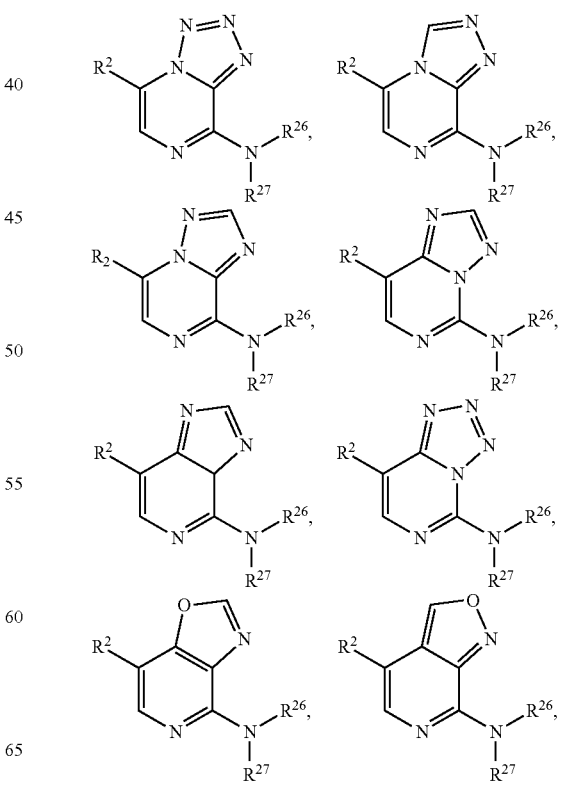

-continued

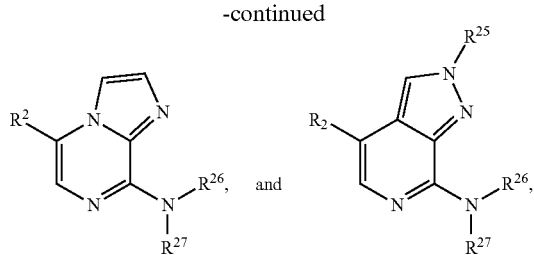 and 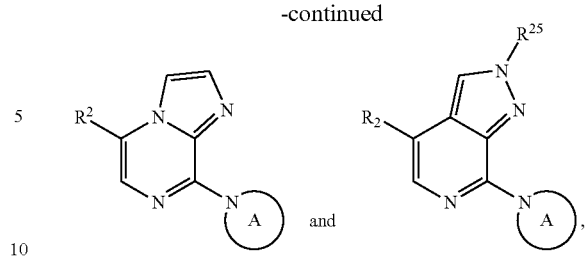

wherein

R² is chosen from alkyl, monocyclic cycloalkyl, monocyclic heterocycloalkyl and monocyclic heteroaryl, any of which may be optionally substituted;

$R^{25}$ is chosen from hydrogen, alkyl, alkenyl, alkynyl, heteroalkyl, alkoxy, halogen, haloalkyl, perhaloalkyl, perhaloalkoxy, amino, aminoalkyl, amido, carboxyl, acyl, hydroxy, cyano, nitro, aryl, arylalkyl, cycloalkyl, cycloalkylalkyl, heterocycloalkyl, heterocycloalkylalkyl, heteroaryl, and heteroarylalkyl, any of which may be optionally substituted; and $R^{26}$ and $R^{27}$ are independently chosen from hydrogen, alkyl, alkenyl, alkynyl, heteroalkyl, alkoxy, halogen, haloalkyl, perhaloalkyl, amino, aminoalkyl, amido, acyl, hydroxy, cyano, nitro, aryl, arylalkyl, cycloalkyl, cycloalkylalkyl, heterocycloalkyl, heterocycloalkylalkyl, heteroaryl, and heteroarylalkyl, any of which may be optionally substituted; or $R^{26}$ and $R^{27}$ together with the nitrogen to which they are attached may combine to form heterocycloalkyl or heteroaryl, either of which is attached through a ring nitrogen to the core and either of which may be optionally substituted.

In certain embodiments, compounds of Formula I have a structure chosen from:

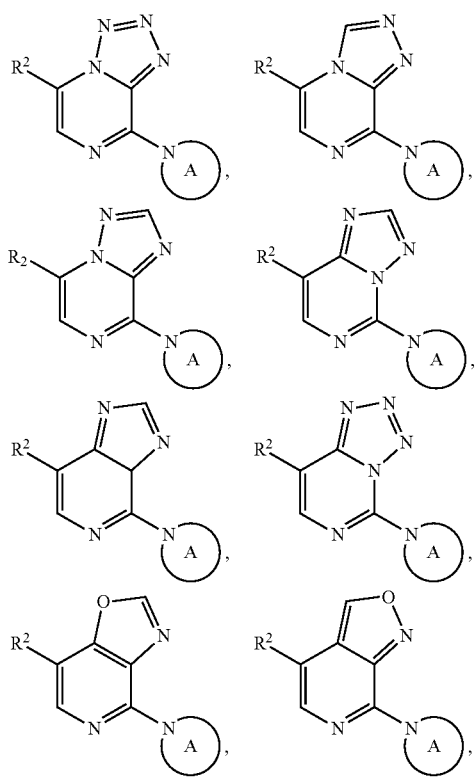

wherein

A is chosen from a monocyclic heterocycloalkyl and a monocyclic heteroaryl, either of which is attached through a ring nitrogen to the core and either of which may be optionally substituted;

R² is chosen from alkyl, phenyl, monocyclic cycloalkyl, monocyclic heterocycloalkyl and monocyclic heteroaryl, any of which may be optionally substituted; and $R^{25}$ is chosen from hydrogen, alkyl, alkenyl, alkynyl, heteroalkyl, alkoxy, halogen, haloalkyl, perhaloalkyl, perhaloalkoxy, amino, aminoalkyl, amido, carboxyl, acyl, hydroxy, cyano, nitro, aryl, arylalkyl, cycloalkyl, cycloalkylalkyl, heterocycloalkyl, heterocycloalkylalkyl, heteroaryl, and heteroarylalkyl, any of which may be optionally substituted.

In certain embodiments, A is four- to seven-membered.

In certain embodiments, $R^{25}$ is chosen from hydrogen and methyl.

In certain embodiments:

$X^2$ is chosen from $[C(R^6)(R^7)]$, and $NR^8$;

$X^4$ is chosen from $[C(R^{12})(R^{13})]$, and $NR^{14}$;

R² is chosen from monocyclic 5- to 7-membered heterocycloalkyl, phenyl, and monocyclic 5- to 6-membered heteroaryl, any of which may be optionally substituted; and $R^{18}$ is chosen from methyl and hydrogen.

In certain embodiments, R² is chosen from phenyl, furan, thiophene, pyrrole, pyrroline, pyrrolidine, oxazole, thiazole, imidazole, pyrazole, imidazoline, imidazolidine, pyrazoline, pyrazolidine, isoxazole, isothiazole, oxadiazole, thiadiazole, triazole, pyran, pyridine, piperidine, morpholine, thiomorpholine, piperazine, pyridazine, pyrimidine, and pyrazine.

In certain embodiments, $R^1$ is optionally substituted monocyclic 4- to 7-membered heterocycloalkyl.

In certain embodiments, $X^1$ is C;

$X^2$ is $NR^8$;

$X^4$ is $NR^{14}$;

$X^5$ is N; and $R^9$ is chosen from null, hydrogen, alkyl, alkoxy, halogen, haloalkyl, acyl perhaloalkyl, amino, aminoalkyl, hydroxy, cyano, any of which may be optionally substituted.

Also provided herein are salts and polymorphs which comprise compounds of structural Formula (VI) together with a counterion

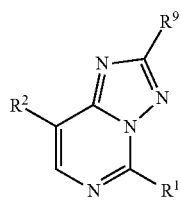

(VI)

wherein:
R¹ is optionally substituted monocyclic 4- to 7-membered heterocycloalkyl; and
R² is chosen from monocyclic 5- to 7-membered heterocycloalkyl, phenyl, and monocyclic 5- to 6-membered heteroaryl, any of which may be optionally substituted; and
R⁹ is chosen from null, hydrogen, and lower alkyl.

In certain embodiments,
X¹ is N;
X² is chosen from [C(R⁶)(R⁷)], and NR⁸;
X⁴ is NR¹⁴;
X⁵ is C;
R¹ is chosen from phenyl, monocyclic 4- to 7-membered heterocycloalkyl, monocyclic 4- to 7-membered cycloalkyl, and monocyclic 5- to 6-membered heteroaryl, any of which may be optionally substituted;
R¹ is optionally substituted monocyclic 4- to 7-membered heterocycloalkyl; and
R² is chosen from monocyclic 5- to 7-membered heterocycloalkyl, phenyl, and monocyclic 5- to 6-membered heteroaryl, either of which may be optionally substituted.

Also provided herein are salts and polymorphs which comprise compounds of structural Formula (VII) together with a counterion

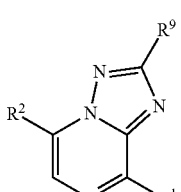

(VII)

wherein:
R¹ is chosen from phenyl, monocyclic 4- to 7-membered heterocycloalkyl, monocyclic 4- to 7-membered cycloalkyl, and monocyclic 5- to 6-membered heteroaryl, any of which may be optionally substituted;
R² is chosen from phenyl, furan, thiophene, pyrrole, pyrroline, pyrrolidine, oxazole, thiazole, imidazole, pyrazole, imidazoline, imidazolidine, pyrazoline, pyrazolidine, isoxazole, isothiazole, oxadiazole, thiadiazole, triazole, pyran, pyridine, piperidine, morpholine, thiomorpholine, piperazine, pyridazine, pyrimidine, and pyrazine, any of which may be optionally substituted; and
R⁹ is chosen from hydrogen, lower alkyl, lower alkoxy, halogen, lower haloalkyl, lower amino, lower aminoalkyl, hydroxy, cyano, any of which may be optionally substituted.

In certain embodiments,
R¹ is chosen from piperazine and azetidine, either of which may be optionally substituted with one to three substituents chosen from lower alkyl and lower amino;
R² is chosen from phenyl, furan, thiophene, and thiazole, any of which may be optionally substituted with one to three substituents chosen from halogen, lower alkyl, lower haloalkyl, lower alkoxy, lower haloalkoxy, cyano, lower amino, hyrdoxy, and nitro.

Also provided herein are salts and polymorphs which comprise compounds of structural Formula (VIII) together with a counterion

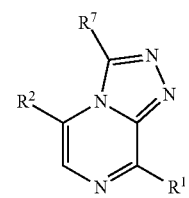

(VIII)

wherein:
R¹ is optionally substituted monocyclic 4- to 7-membered heterocycloalkyl;
R² is chosen from monocyclic 5- to 7-membered heterocycloalkyl, phenyl, and monocyclic 5- to 6-membered heteroaryl, either of which may be optionally substituted with one to three substituents chosen from halogen, lower alkyl, lower haloalkyl, lower alkoxy, lower haloalkoxy, cyano, lower amino, hyrdoxy, and nitro; and
R⁷ is chosen from hydrogen, alkyl, alkoxy, halogen, haloalkyl, perhaloalkyl, amino, aminoalkyl, hydroxy, cyano, any of which may be optionally substituted.

Also provided herein are salts and polymorphs which comprise compounds of structural Formula (IX) together with a counterion

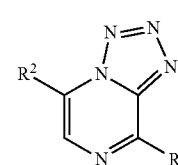

(IX)

wherein:
R¹ is optionally substituted monocyclic 4- to 7-membered heterocycloalkyl; and
R² is chosen from monocyclic 5- to 7-membered heterocycloalkyl, phenyl and monocyclic 5- to 6-membered heteroaryl, either of which may be optionally substituted with one to three substituents chosen from halogen, lower alkyl, lower haloalkyl, lower alkoxy, lower haloalkoxy, cyano, lower amino, hyrdoxy, and nitro.

Also provided herein are salts and polymorphs which comprise compounds of structural Formula (X) together with a counterion

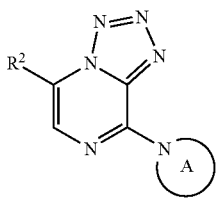

(X)

wherein:

A is chosen from a monocyclic 4- to 7-membered heterocycloalkyl and a monocyclic 5- to 6-membered heteroaryl, either of which is attached through a ring nitrogen to the core and either of which may be optionally substituted; and $R^2$ is chosen from phenyl, furan, thiophene, pyrrole, pyrroline, pyrrolidine, oxazole, thiazole, imidazole, pyrazole, imidazoline, imidazolidine, pyrazoline, pyrazolidine, isoxazole, isothiazole, oxadiazole, thiadiazole, triazole, pyran, pyridine, piperidine, morpholine, thiomorpholine, piperazine, pyridazine, pyrimidine, and pyrazine, any of which may be optionally substituted.

Also provided herein are salts and polymorphs which comprise compounds of structural Formula (XI) together with a counterion

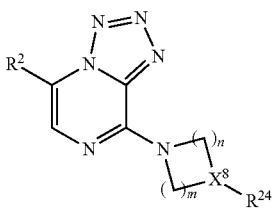

(XI)

wherein:

$X^8$ is chosen from CH and N;

m and n are each an integer chosen from 1 and 2;

$R^2$ is chosen from phenyl, furan, thiophene, and thiazole, any of which may be optionally substituted with one to three substituents chosen from halogen, lower alkyl, lower haloalkyl, lower alkoxy, lower haloalkoxy, cyano, lower amino, hyrdoxy, and nitro; and $R^{24}$ is chosen from hydrogen, amino, and lower alkyl.

In certain embodiments, $X^8$ is CH;

m and n are each 1; and $R^{24}$ is chosen from hydrogen, amino, and lower alkyl.

In certain embodiments, $R^{24}$ is amino.

In certain embodiments, $R^{24}$ is $NHCH_3$.

In certain embodiments, $X^8$ is N;

m and n are each 2; and $R^{24}$ is chosen from hydrogen and lower alkyl.

In certain embodiments, $R^{24}$ is chosen from hydrogen and methyl.

In certain embodiments, $R^{24}$ is methyl.

In certain embodiments provided herein, $R^2$ is chosen from phenyl, furan, thiophene, pyrrole, pyrroline, pyrrolidine, oxazole, thiazole, imidazole, pyrazole, imidazoline, imidazolidine, pyrazoline, pyrazolidine, isoxazole, isothiazole, oxadiazole, thiadiazole, triazole, pyran, pyridine, piperidine, morpholine, thiomorpholine, piperazine, pyridazine, pyrimidine, and pyrazine.

Also provided herein are compounds, or salts, hydrates or polymorphs thereof, of structural Formula (XII)

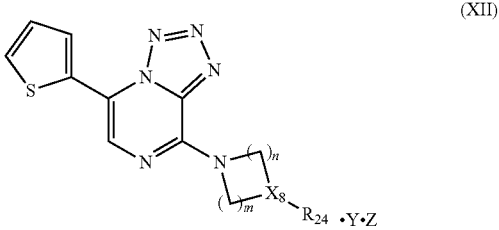

(XII)

or a salt, hydrate, or polymorph thereof, wherein:

$X^8$ is chosen from CH and N;

m and n are each an integer chosen from 1 and 2;

$R^{24}$ is chosen from lower amino, lower alkylamino, and lower alkyl;

Y is chosen from a counterion and null; and

Z is a chosen from a hydrate and null.

In certain embodiments, provided herein are compounds, or salts, polymorphs, or hydrates thereof, in which:

Y is a counterion, if the compound of Formula I is a salt, or

Y is chosen from a counterion and null, if the compound of Formula I is a polymorph.

In certain embodiments, provided herein are compounds, or salts, polymorphs, or hydrates thereof, in which:

$X^8$ is N;

m and n are each 2; and $R^{24}$ is lower alkyl.

In further embodiments, $R^{24}$ is methyl.

In certain embodiments, the compound is 8-(4-Methylpiperazin-1-yl)-5-(thiophen-2-yl)tetrazolo[1,5-a]pyrazine, or a salt, hydrate, or polymorph thereof.

In other embodiments, provided herein are compounds, or salts, polymorphs, or hydrates thereof, in which:

$X^8$ is CH;

m and n are each 1;

$R^{24}$ is lower alkylamino.

In certain embodiments, $R^{24}$ is lower alkylamino.

In further embodiments, $R^{24}$ is lower methylamino.

In certain embodiments, the compound is N-methyl-1-(5-(thiophen-2-yl)tetrazolo[1,5-a]pyrazin-8-yl)azetidin-3-amine, or a salt, hydrate, or polymorph thereof.

In certain embodiments, provided herein are compounds, or salts, polymorphs, or hydrates thereof, in which:

Y is a counterion, if the compound of Formula XII is a salt, or

Y is chosen from a counterion and null, if the compound of Formula XII is a polymorph.

In certain embodiments, Y is a counterion and the compound is a salt, or a polymorph or hydrate thereof.

In further embodiments, Y is a counterion chosen from acetate, citrate, sulfate, phosphate, hydrochloride, aspartate, mesylate, malate, tartrate, stearate, and succinate.

In further embodiments, the counterion is chosen from tartrate, mesylate, citrate, and hydrochloride.

In certain embodiments, Z is chosen from a stoichiometric hydrate and a nonstoichiometric hydrate, or a polymorph thereof.

In further embodiments, Z is chosen from a monohydrate and a hemihydrate.

In certain embodiments, provided herein are compounds, or salts, polymorphs, or hydrates thereof, having structural Formula (XIII)

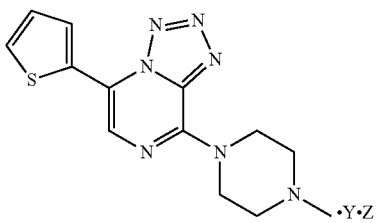

(XIII)

or a salt, polymorph or hydrate thereof, wherein:
Y is a counterion chosen from tartrate and mesylate; and
Z is a chosen from a monohydrate, a hemihydrate, and null.

In certain embodiments, provided herein is the salt 8-(4-methylpiperazin-1-yl)-5-(thiophen-2-yl)tetrazolo[1,5-a]pyrazine mesylate, or a hydrate or polymorph thereof.

In certain embodiments, provided herein is a hydrate of the salt, which is 8-(4-methylpiperazin-1-yl)-5-(thiophen-2-yl)tetrazolo[1,5-a]pyrazine mesylate monohydrate, or a polymorph thereof.

In certain embodiments, provided herein is a polymorph of the hydrate, which is 8-(4-methylpiperazin-1-yl)-5-(thiophen-2-yl)tetrazolo[1,5-a]pyrazine mesylate monohydrate Form 1. In certain embodiments, the polymorph comprises at least 75% 8-(4-Methylpiperazin-1-yl)-5-(thiophen-2-yl)tetrazolo[1,5-a]pyrazine mesylate monohydrate Form 1. In certain embodiments, the polymorph comprises at least 80% 8-(4-Methylpiperazin-1-yl)-5-(thiophen-2-yl)tetrazolo[1,5-a]pyrazine mesylate monohydrate Form 1. In certain embodiments, the polymorph comprises at least 90% 8-(4-Methylpiperazin-1-yl)-5-(thiophen-2-yl)tetrazolo[1,5-a]pyrazine mesylate monohydrate Form 1. In certain embodiments, the polymorph comprises at least 95% 8-(4-Methylpiperazin-1-yl)-5-(thiophen-2-yl)tetrazolo[1,5-a]pyrazine mesylate monohydrate Form 1. In certain embodiments, the polymorph comprises at least 96% 8-(4-Methylpiperazin-1-yl)-5-(thiophen-2-yl)tetrazolo[1,5-a]pyrazine mesylate monohydrate Form 1. In certain embodiments, the polymorph comprises at least 97% 8-(4-Methylpiperazin-1-yl)-5-(thiophen-2-yl)tetrazolo[1,5-a]pyrazine mesylate monohydrate Form 1. In certain embodiments, the polymorph comprises at least 98% 8-(4-Methylpiperazin-1-yl)-5-(thiophen-2-yl)tetrazolo[1,5-a]pyrazine mesylate monohydrate Form 1. In certain embodiments, the polymorph comprises at least 99% 8-(4-Methylpiperazin-1-yl)-5-(thiophen-2-yl)tetrazolo[1,5-a]pyrazine mesylate monohydrate Form 1.

In certain embodiments, the polymorph is 8-(4-methylpiperazin-1-yl)-5-(thiophen-2-yl)tetrazolo[1,5-a]pyrazine mesylate Form 3

In certain embodiments, provided herein is a salt, which is 8-(4-methylpiperazin-1-yl)-5-(thiophen-2-yl)tetrazolo[1,5-a]pyrazine tartrate, or a hydrate or polymorph thereof.

In certain embodiments, provided herein is a polymorph of the salt, which is 8-(4-methylpiperazin-1-yl)-5-(thiophen-2-yl)tetrazolo[1,5-a]pyrazine tartrate hemihydrate (Form 1). In certain embodiments, the polymorph comprises at least 75%, at least 80%, at least 85%, at least 90%, at least 95%, at least 96%, at least 97%, at least 98%, or at least 99% 8-(4-Methylpiperazin-1-yl)-5-(thiophen-2-yl)tetrazolo[1,5-a]pyrazine mesylate tartrate hemihydrate (Form 1).

In other embodiments, provided herein is a polymorph of the salt, which is 8-(4-methylpiperazin-1-yl)-5-(thiophen-2-yl)tetrazolo[1,5-a]pyrazine tartrate monohydrate (Form 2). In certain embodiments, the polymorph comprises at least 75%, at least 80%, at least 85%, at least 90%, at least 95%, at least 96%, at least 97%, at least 98%, or at least 99% 8-(4-Methylpiperazin-1-yl)-5-(thiophen-2-yl)tetrazolo[1,5-a]pyrazine mesylate tartrate monohydrate (Form 2).

In certain embodiments, provided herein are compounds, or salts, polymorphs, or hydrates thereof, having structural Formula (XIV)

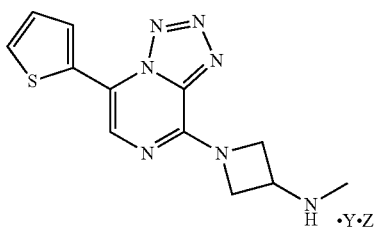

(XIV)

or a polymorph or hydrate thereof, wherein:
Y is a counterion chosen from citrate, hydrochloride, mesylate; and
Z is a chosen from a monohydrate, a hemihydrate, and null.

In certain embodiments, provided herein is the salt N-methyl-1-(5-(thiophen-2-yl)tetrazolo[1,5-a]pyrazin-8-yl)azetidin-3-amine citrate, or a hydrate or polymorph thereof.

In further embodiments, provided herein is a polymorph of the salt, which is N-methyl-1-(5-(thiophen-2-yl)tetrazolo[1,5-a]pyrazin-8-yl)azetidin-3-amine citrate Form 1. In certain embodiments, the polymorph comprises at least 75%, at least 80%, at least 85%, at least 90%, at least 95%, at least 96%, at least 97%, at least 98%, or at least 99% N-methyl-1-(5-(thiophen-2-yl)tetrazolo[1,5-a]pyrazin-8-yl)azetidin-3-amine citrate Form 1.

In other embodiments, provided herein is the salt N-methyl-1-(5-(thiophen-2-yl)tetrazolo[1,5-a]pyrazin-8-yl)azetidin-3-amine hydrochloride, or a hydrate or polymorph thereof.

In further embodiments, provided herein is a polymorph of the salt, which is N-methyl-1-(5-(thiophen-2-yl)tetrazolo[1,5-a]pyrazin-8-yl)azetidin-3-amine hydrochloride Form 1. In certain embodiments, the polymorph comprises at least 75% N-methyl-1-(5-(thiophen-2-yl)tetrazolo[1,5-a]pyrazin-8-yl)azetidin-3-amine hydrochloride Form 1. In certain embodiments, the polymorph comprises at least 80% N-methyl-1-(5-(thiophen-2-yl)tetrazolo[1,5-a]pyrazin-8-yl)azetidin-3-amine hydrochloride Form 1. In certain embodiments, the polymorph comprises at least 90% N-methyl-1-(5-(thiophen-2-yl)tetrazolo[1,5-a]pyrazin-8-yl)azetidin-3-amine hydrochloride Form 1. In certain embodiments, the polymorph comprises at least 95% N-methyl-1-(5-(thiophen-2-yl)tetrazolo[1,5-a]pyrazin-8-yl)azetidin-3-amine hydrochloride Form 1. In certain embodiments, the polymorph comprises at least 96% N-methyl-1-(5-(thiophen-2-yl)tetrazolo[1,5-a]pyrazin-8-yl)azetidin-3-amine hydrochloride Form 1. In certain embodiments, the polymorph comprises at least 97% N-methyl-1-(5-(thiophen-2-yl)tetrazolo[1,5-a]pyrazin-8-yl)azetidin-3-amine hydrochloride Form 1. In certain embodiments, the polymorph comprises at least 98% N-methyl-1-(5-(thiophen-2-yl)tetrazolo[1,5-a]pyrazin-8-yl)azetidin-3-amine hydrochloride Form 1. In certain embodiments, the polymorph comprises at least 99% N-methyl-1-(5-(thiophen-2-yl)tetrazolo[1,5-a]pyrazin-8-yl)azetidin-3-amine hydrochloride Form 1.

In yet other embodiments, provided herein is the salt N-methyl-1-(5-(thiophen-2-yl)tetrazolo[1,5-a]pyrazin-8-yl)azetidin-3-amine mesylate, or a hydrate or polymorph thereof.

In further embodiments, provided herein is a polymorph of the salt, which is N-methyl-1-(5-(thiophen-2-yl)tetrazolo[1,5-a]pyrazin-8-yl)azetidin-3-amine mesylate Form 1. In certain embodiments, provided herein is a polymorph of the hydrate, which is N-methyl-1-(5-(thiophen-2-yl)tetrazolo[1,5-a]pyrazin-8-yl)azetidin-3-amine mesylate Form 1. In certain embodiments, the polymorph comprises at least 75% N-methyl-1-(5-(thiophen-2-yl)tetrazolo[1,5-a]pyrazin-8-yl)azetidin-3-amine mesylate Form 1. In certain embodiments, the polymorph comprises at least 80% N-methyl-1-(5-(thiophen-2-yl)tetrazolo[1,5-a]pyrazin-8-yl)azetidin-3-amine mesylate Form 1. In certain embodiments, the polymorph comprises at least 90% N-methyl-1-(5-(thiophen-2-yl)tetrazolo[1,5-a]pyrazin-8-yl)azetidin-3-amine mesylate Form 1. In certain embodiments, the polymorph comprises at least 95% N-methyl-1-(5-(thiophen-2-yl)tetrazolo[1,5-a]pyrazin-8-yl)azetidin-3-amine mesylate Form 1. In certain embodiments, the polymorph comprises at least 96% N-methyl-1-(5-(thiophen-2-yl)tetrazolo[1,5-a]pyrazin-8-yl)azetidin-3-amine mesylate Form 1. In certain embodiments, the polymorph comprises at least 97% N-methyl-1-(5-(thiophen-2-yl)tetrazolo[1,5-a]pyrazin-8-yl)azetidin-3-amine mesylate Form 1. In certain embodiments, the polymorph comprises at least 98% N-methyl-1-(5-(thiophen-2-yl)tetrazolo[1,5-a]pyrazin-8-yl)azetidin-3-amine mesylate Form 1. In certain embodiments, the polymorph comprises at least 99% N-methyl-1-(5-(thiophen-2-yl)tetrazolo[1,5-a]pyrazin-8-yl)azetidin-3-amine mesylate Form 1.

In certain embodiments, provided herein is a compound of Formula XII as recited above, or a salt, hydrate, or polymorph thereof, which forms a crystalline solid which has a solubility, in aqueous media at about pH 3.5 to about pH 5.0, of at least 2.5 mg/mL.

In further embodiments, the compound of Formula XII as recited above, or a salt, hydrate, or polymorph thereof, has a solubility, in aqueous media at about pH 3.5 to about pH 5.0, of at least 5.0 mg/mL.

In further embodiments, the compound of Formula XII as recited above, or a salt, hydrate, or polymorph thereof, has a solubility, in aqueous media at about pH 3.5 to about pH 5.0, of at least 10.0 mg/mL.

In further embodiments, the compound of Formula XII as recited above, or a salt, hydrate, or polymorph thereof, has a solubility, in aqueous media at about pH 3.5 to about pH 5.0, of at least 20.0 mg/mL.

In further embodiments, the compound of Formula XII as recited above, or a salt, hydrate, or polymorph thereof, has a solubility, in aqueous media at about pH 3.5 to about pH 5.0, of at least 30.0 mg/mL.

In certain embodiments, compound is a polymorph and Y is null.

In certain embodiments, the compound is a polymorph of 8-(4-methylpiperazin-1-yl)-5-(thiophen-2-yl)tetrazolo[1,5-a]pyrazine.

In certain embodiments, the compound is a polymorph of N-methyl-1-(5-(thiophen-2-yl)tetrazolo[1,5-a]pyrazin-8-yl)azetidin-3-amine.

In certain embodiments, provided herein is 8-(4-Methylpiperazin-1-yl)-5-(thiophen-2-yl)tetrazolo[1,5-a]pyrazine Tartrate Hemihydrate, having the structural formula (XV)

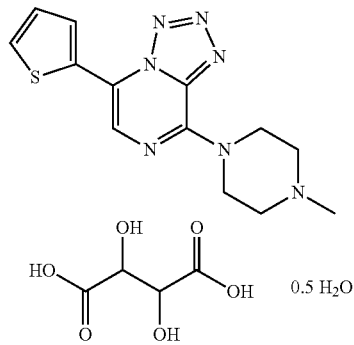

(XV)

in a crystalline form.

Figure 2:
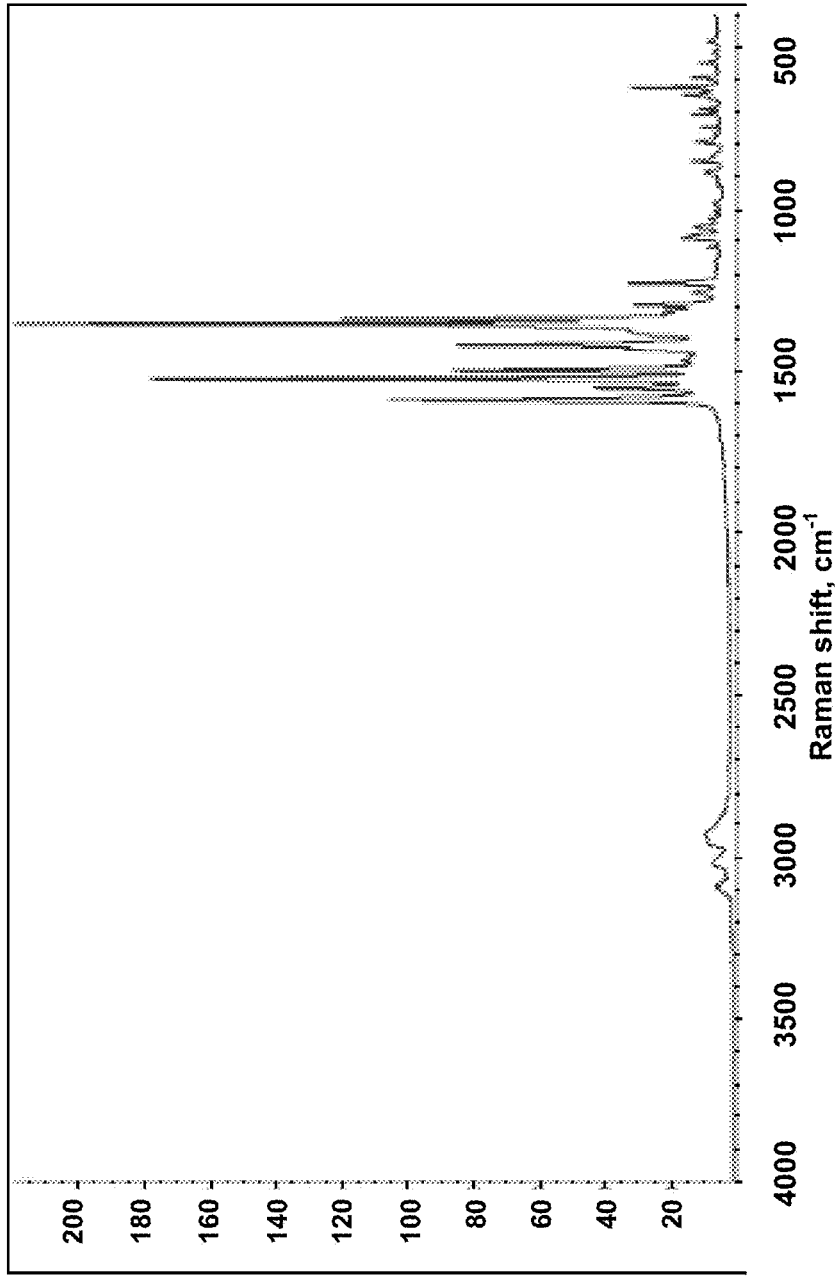
FIG. 2: FT-Raman Spectrum of 8-(4-Methylpiperazin-1-yl)-5-(thiophen-2-yl)tetrazolo[1,5-a]pyrazine Tartrate Hemihydrate Form 1, also known as Compound 1, Tartrate Salt, Form 1. In the figure, the horizontal axis is the Raman shift in units of $cm^{-1}$.

In certain embodiments, the crystalline form of 8-(4-Methylpiperazin-1-yl)-5-(thiophen-2-yl)tetrazolo[1,5-a]pyrazine Tartrate Hemihydrate is characterized in that said form has at least one of the following characteristics:

an X-ray powder diffraction pattern with peaks at 10.2, 13.4, 17.4, 18.1, 23.5 and 26.0 degrees two theta (±0.2 degree) (CuKα λ=1.54059 A), or an X-ray powder diffraction pattern substantially in accordance with that shown in FIG. 1; and an FT-Raman spectrum with the bands at 1339, 1356, 1524 and 1589 cm$^{-1}$ or an FT-Raman spectrum substantially in accordance with that shown in FIG. 2.

In certain embodiments, provided herein is 8-(4-Methylpiperazin-1-yl)-5-(thiophen-2-yl)tetrazolo[1,5-a]pyrazine Tartrate Monohydrate, having the structural formula (XVI)

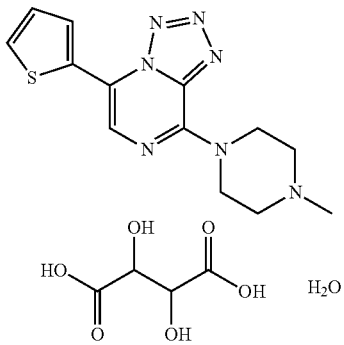

(XVI)

in a crystalline form.

Figure 5:
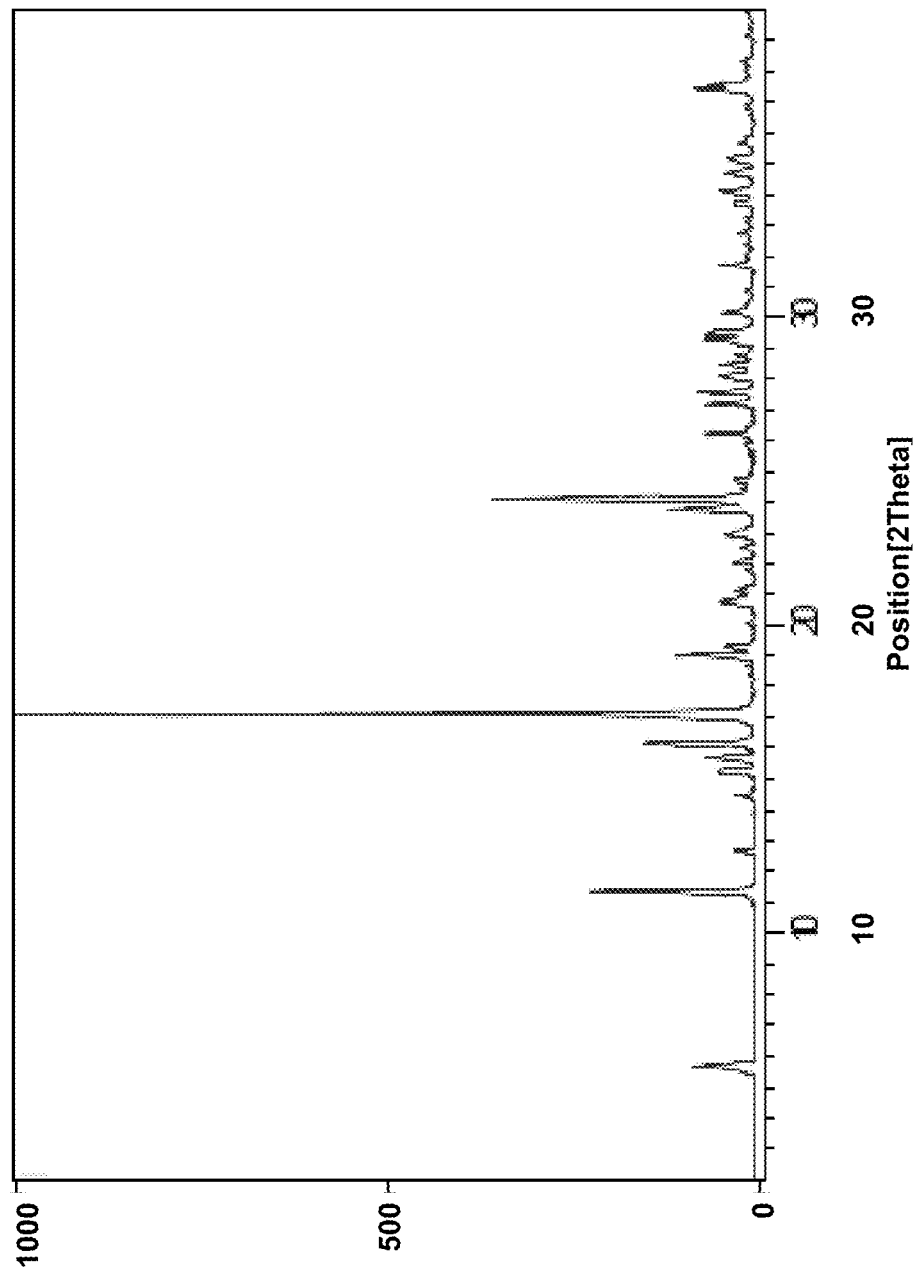
FIG. 5: PXRD diffractogram of 8-(4-Methylpiperazin-1-yl)-5-(thiophen-2-yl)tetrazolo[1,5-a]pyrazine Tartrate Monohydrate Form 2, also known as Compound 1 Tartrate Salt Form 2.
Figure 6:
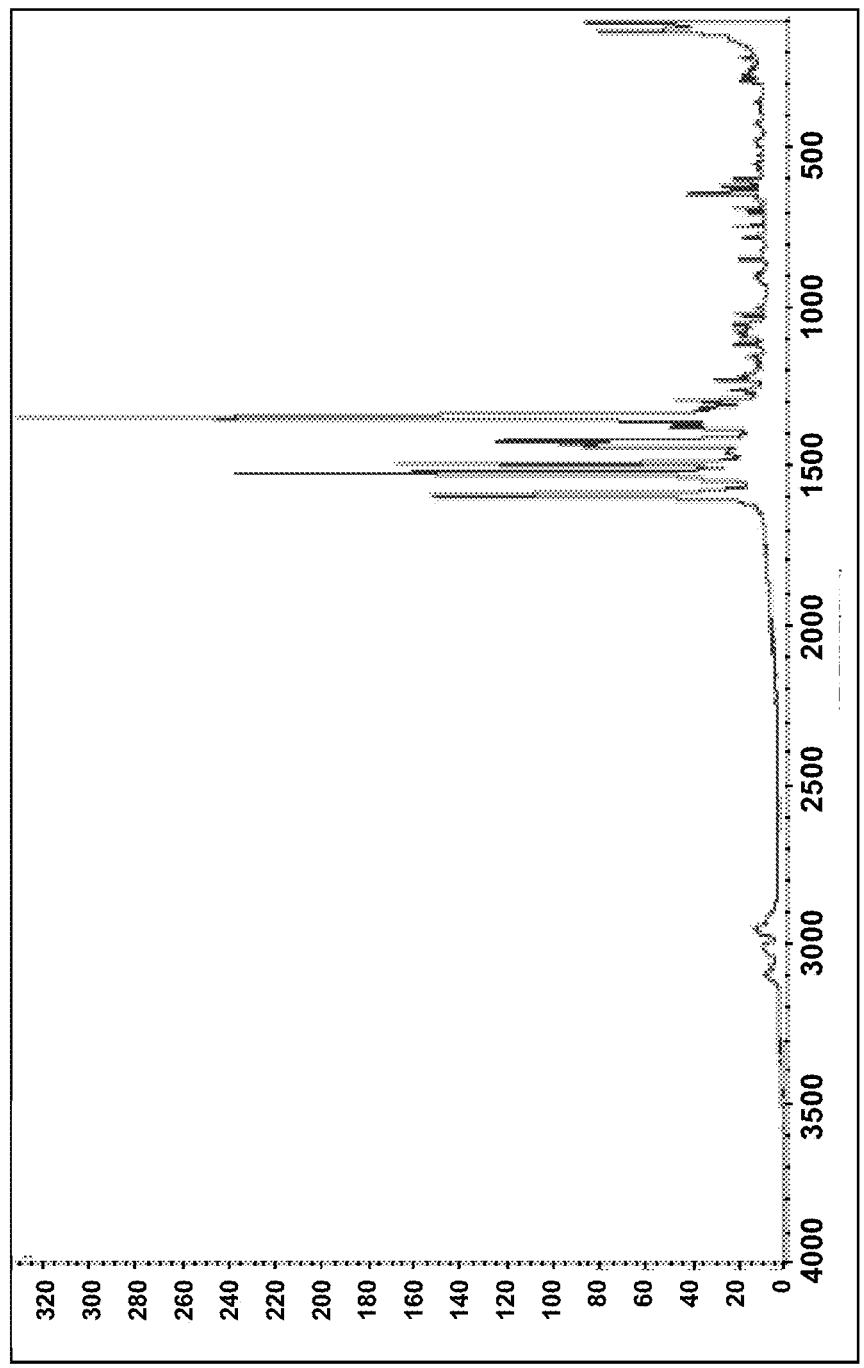
FIG. 6: FT-Raman Spectrum of 8-(4-Methylpiperazin-1-yl)-5-(thiophen-2-yl)tetrazolo[1,5-a]pyrazine Tartrate Monohydrate Form 2, also known as Compound 1, Tartrate Salt, Form 2. In the figure, the horizontal axis is the Raman shift in units of $cm^{-1}$.

In certain embodiments, the crystalline form of 8-(4-Methylpiperazin-1-yl)-5-(thiophen-2-yl)tetrazolo[1,5-a]pyrazine Tartrate Monohydrate is characterized in that said form has at least one of the following characteristics:

an X-ray powder diffraction pattern with peaks at 11.4, 16.2, 17.1 19.0, 23.8 and 24.1 degrees two theta (±0.2 degree) (CuKα λ=1.54059 A), or an X-ray powder diffraction pattern substantially in accordance with that shown in FIG. 5; and an FT-Raman spectrum with the bands at 1350, 1422, 1494, 1522 and 1593 cm$^{-1}$ or an FT-Raman spectrum substantially in accordance with that shown in FIG. 6.

In certain embodiments, provided herein is 8-(4-Methylpiperazin-1-yl)-5-(thiophen-2-yl)tetrazolo[1,5-a]pyrazine Mesylate Monohydrate, having the structural formula (XVII)

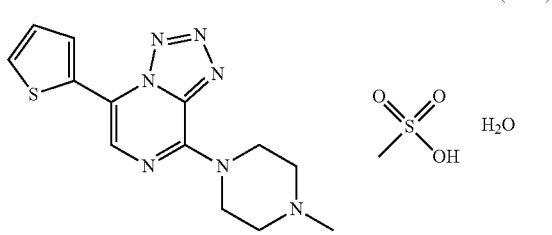

(XVII)

in crystalline form.

Figure 9:
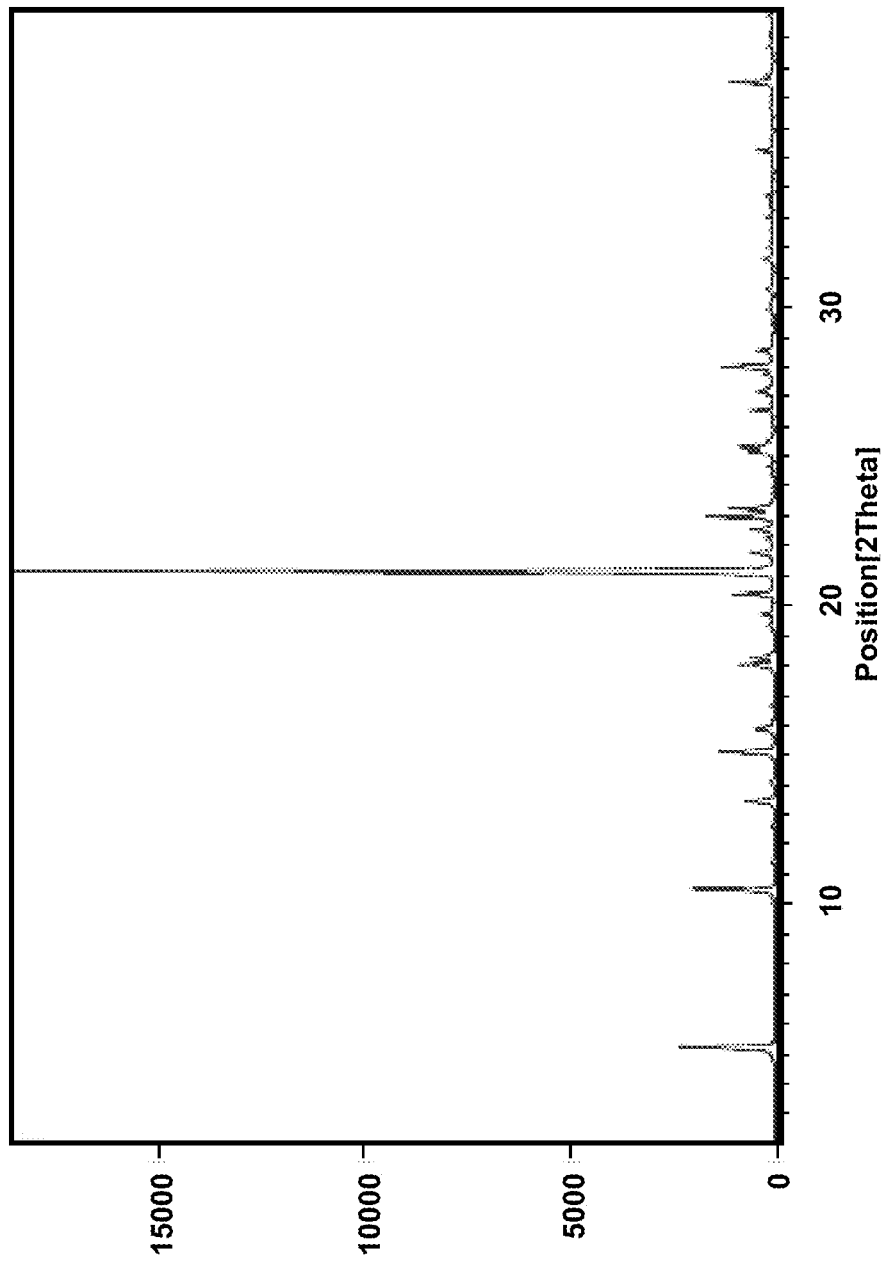
FIG. 9: PXRD diffractogram of 8-(4-Methylpiperazin-1-yl)-5-(thiophen-2-yl)tetrazolo[1,5-a]pyrazine Mesylate Monohydrate Form 1, also known as Compound 1, Mesylate Salt, Form 1.
Figure 10:
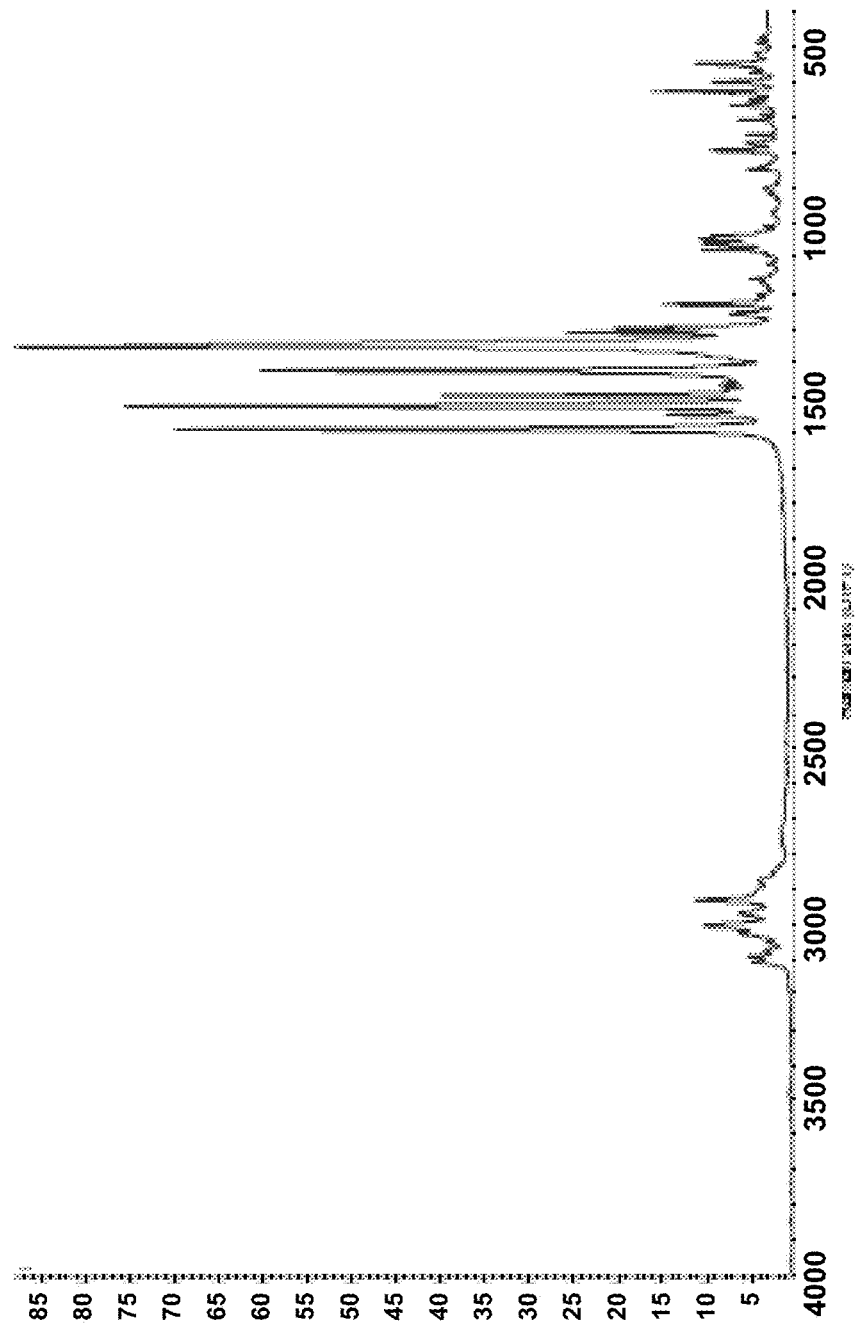
FIG. 10: FT-Raman Spectrum of 8-(4-Methylpiperazin-1-yl)-5-(thiophen-2-yl)tetrazolo[1,5-a]pyrazine Mesylate Monohydrate Form 1, also known as Compound 1, Mesylate Salt, Form 1. In the figure, the horizontal axis is the Raman shift in units of $cm^{-1}$.

In certain embodiments, the crystalline form of 8-(4-Methylpiperazin-1-yl)-5-(thiophen-2-yl)tetrazolo[1,5-a]pyrazine Mesylate Monohydrate is characterized in that said form has at least one of the following characteristics:

an X-ray powder diffraction pattern with peaks at 5.3, 10.5, 15.1, 20.4, 21.2, 21.8 and 23.0 degrees two theta (±0.2 degree) (CuKα λ=1.54059 A), or an X-ray powder diffraction pattern substantially in accordance with that shown in FIG. 9; and an FT-Raman spectrum with the bands at 1299, 1313, 1354, 1422, 1494, 1523 and 1590 cm$^{-1}$ or an FT-Raman spectrum substantially in accordance with that shown in FIG. 10

In certain embodiments, provided herein is 8-(4-Methylpiperazin-1-yl)-5-(thiophen-2-yl)tetrazolo[1,5-a]pyrazine Mesylate, having the structural formula (XVIII)

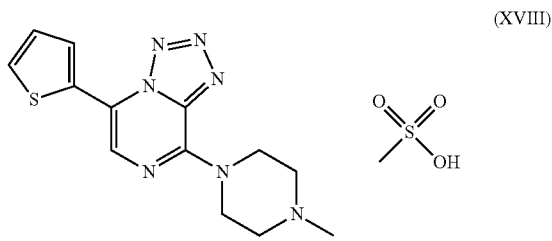

(XVIII)

in a crystalline form.

Figure 17:
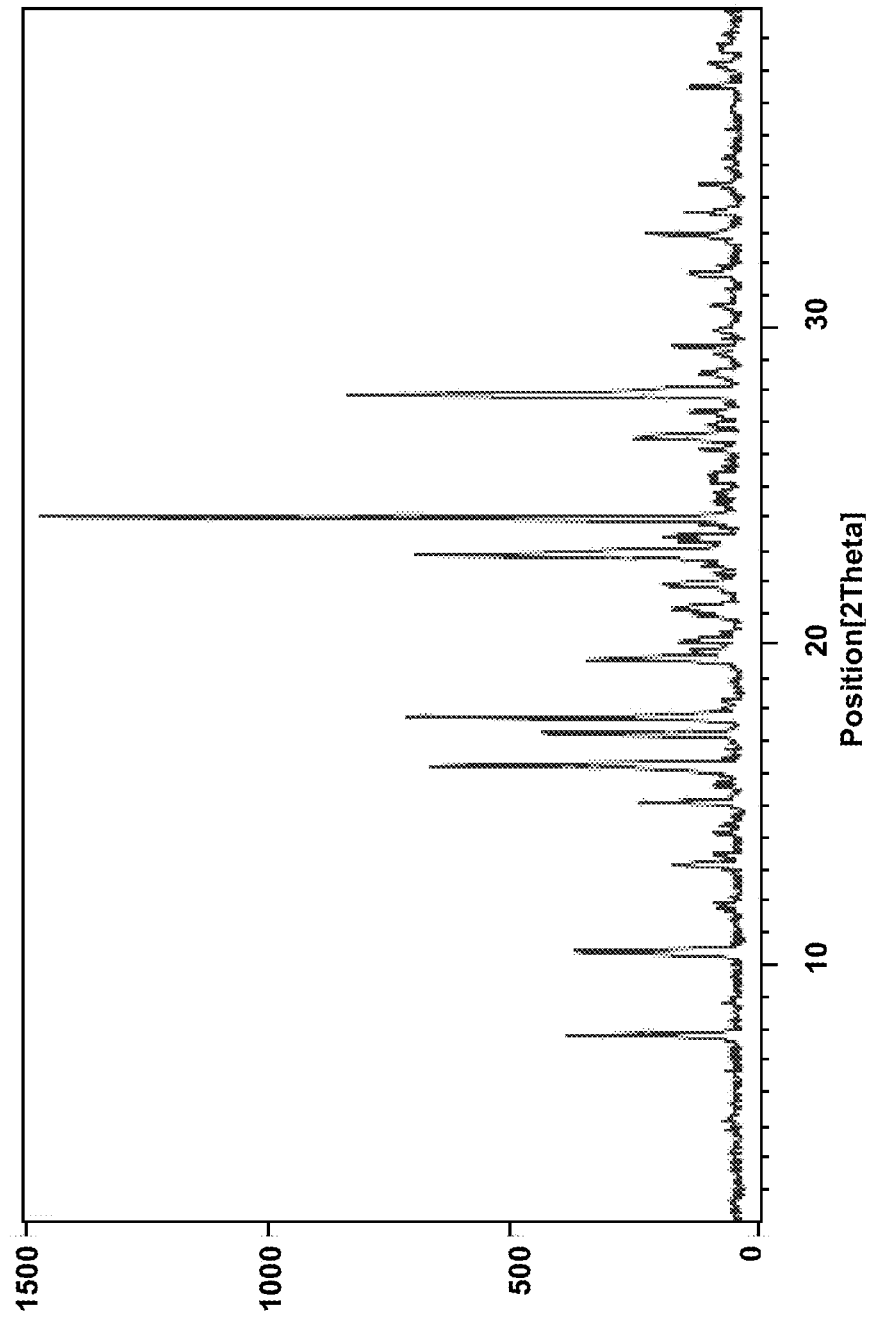
FIG. 17: PXRD diffractogram of 8-(4-Methylpiperazin-1-yl)-5-(thiophen-2-yl)tetrazolo[1,5-a]pyrazine Mesylate Form 3, also known as Compound 1 Mesylate Form 3.
Figure 18:
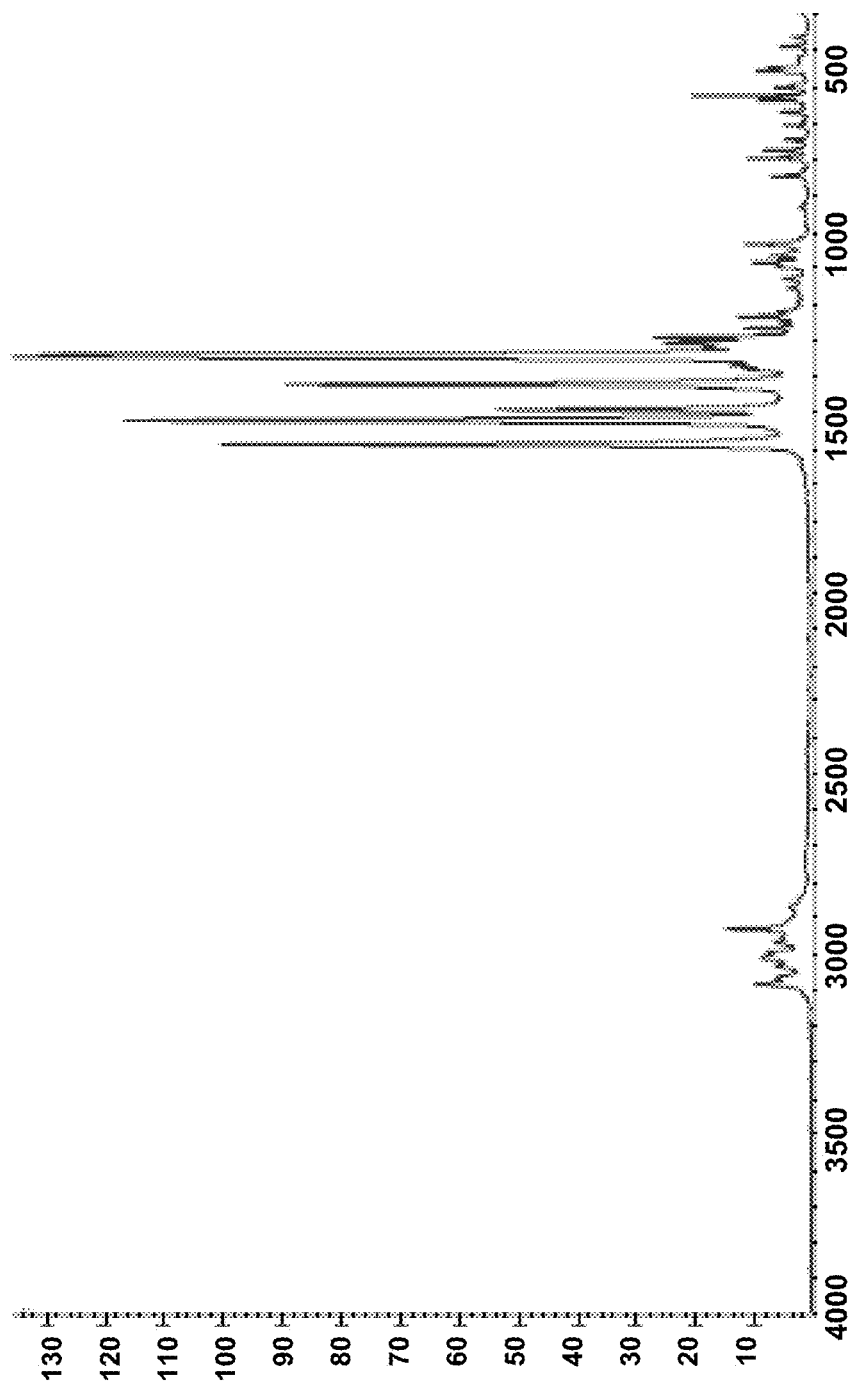
FIG. 18: FT-Raman Spectrum of 8-(4-Methylpiperazin-1-yl)-5-(thiophen-2-yl)tetrazolo[1,5-a]pyrazine Mesylate Form 3, also known as Compound 1 Mesylate Form 3. In the figure, the horizontal axis is the Raman shift in units of $cm^{-1}$.

In certain embodiments, the crystalline form of 8-(4-Methylpiperazin-1-yl)-5-(thiophen-2-yl)tetrazolo[1,5-a]pyrazine Mesylate is characterized in that said form has at least one of the following characteristics:

an X-ray powder diffraction pattern with peaks at 10.4, 16.3, 17.2, 17.8, 22.8, 24.0 and 27.8 degrees two theta (±0.2 degree) (CuKα λ=1.54059 A), or an X-ray powder diffraction pattern substantially in accordance with that shown in FIG. 17; and an FT-Raman spectrum with the bands at 1346, 1423, 1493, 1524 and 1589 cm$^{-1}$ or an FT-Raman spectrum substantially in accordance with that shown in FIG. 18.

In certain embodiments, provided herein is N-methyl-1-(5-(thiophen-2-yl)tetrazolo[1,5-a]pyrazin-8-yl)azetidin-3-amine Citrate, having the structural formula (XIX)

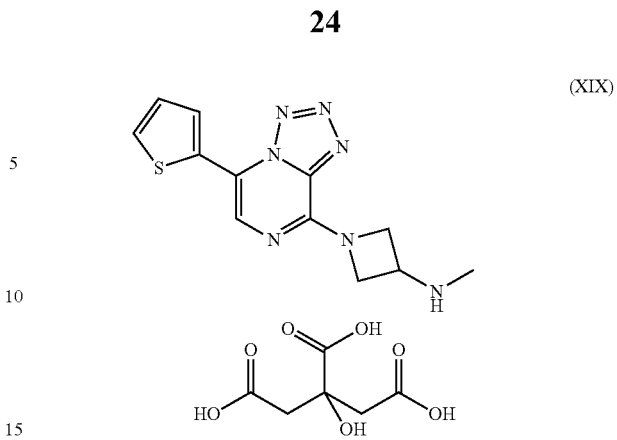

(XIX)

in a crystalline form.

Figure 20:
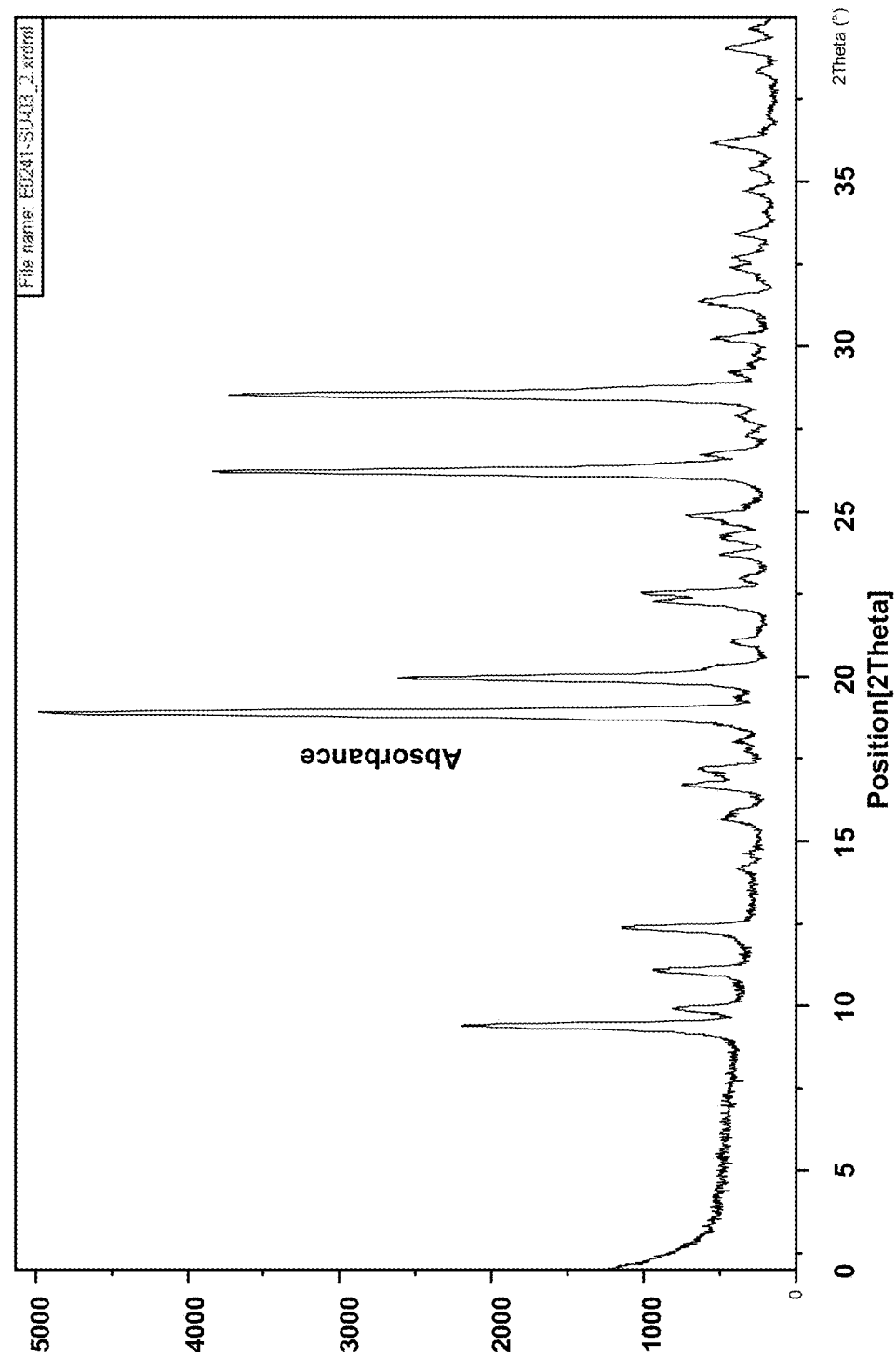
FIG. 20: PXRD diffractogram of N-methyl-1-(5-(thiophen-2-yl)tetrazolo[1,5-a]pyrazin-8-yl)azetidin-3-amine Citrate Form 1, also known as Compound 2 Citrate Salt Form 1.
Figure 21:
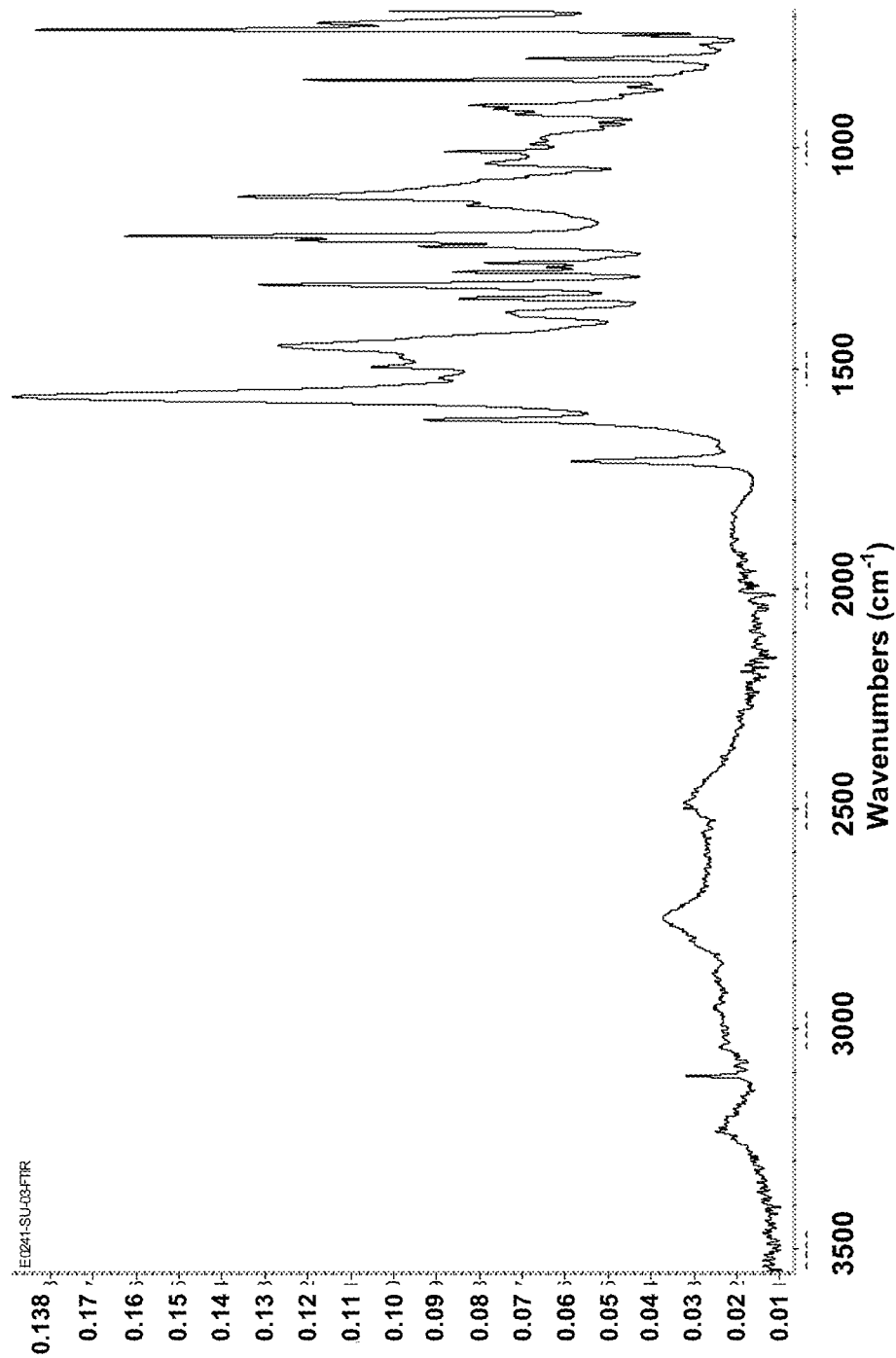
FIG. 21: FTIR Spectrum of N-methyl-1-(5-(thiophen-2-yl)tetrazolo[1,5-a]pyrazin-8-yl)azetidin-3-amine Citrate Form 1, also known as Compound 2 Citrate Salt Form 1.

In certain embodiments, the crystalline form of N-methyl-1-(5-(thiophen-2-yl)tetrazolo[1,5-a]pyrazin-8-yl)azetidin-3-amine Citrate is characterized in that said form has at least one of the following characteristics:

an X-ray powder diffraction pattern with peaks at 9.4, 12.4, 18.9, 19.9, 26.2 and 28.6 degrees two theta (±0.2 degree) (CuKα λ=1.54059 A), or an X-ray powder diffraction pattern substantially in accordance with that shown in FIG. 20; and an FTIR spectrum with the bands at 731, 844, 1110, 1199, 1209, 1310, 1448 and 1564 cm$^{-1}$ or an FTIR spectrum substantially in accordance with that shown in FIG. 21.

In certain embodiments, provided herein is N-methyl-1-(5-(thiophen-2-yl)tetrazolo[1,5-a]pyrazin-8-yl)azetidin-3-amine Hydrochloride, having the structural formula (XX)

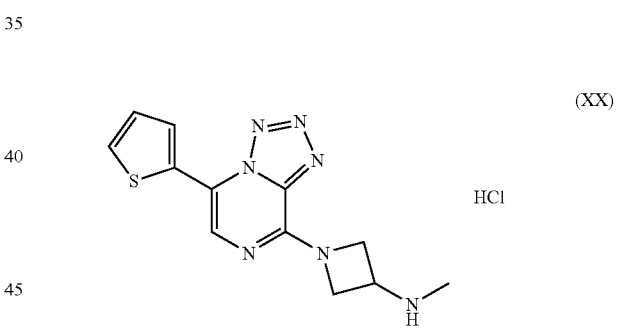

Figure 24:
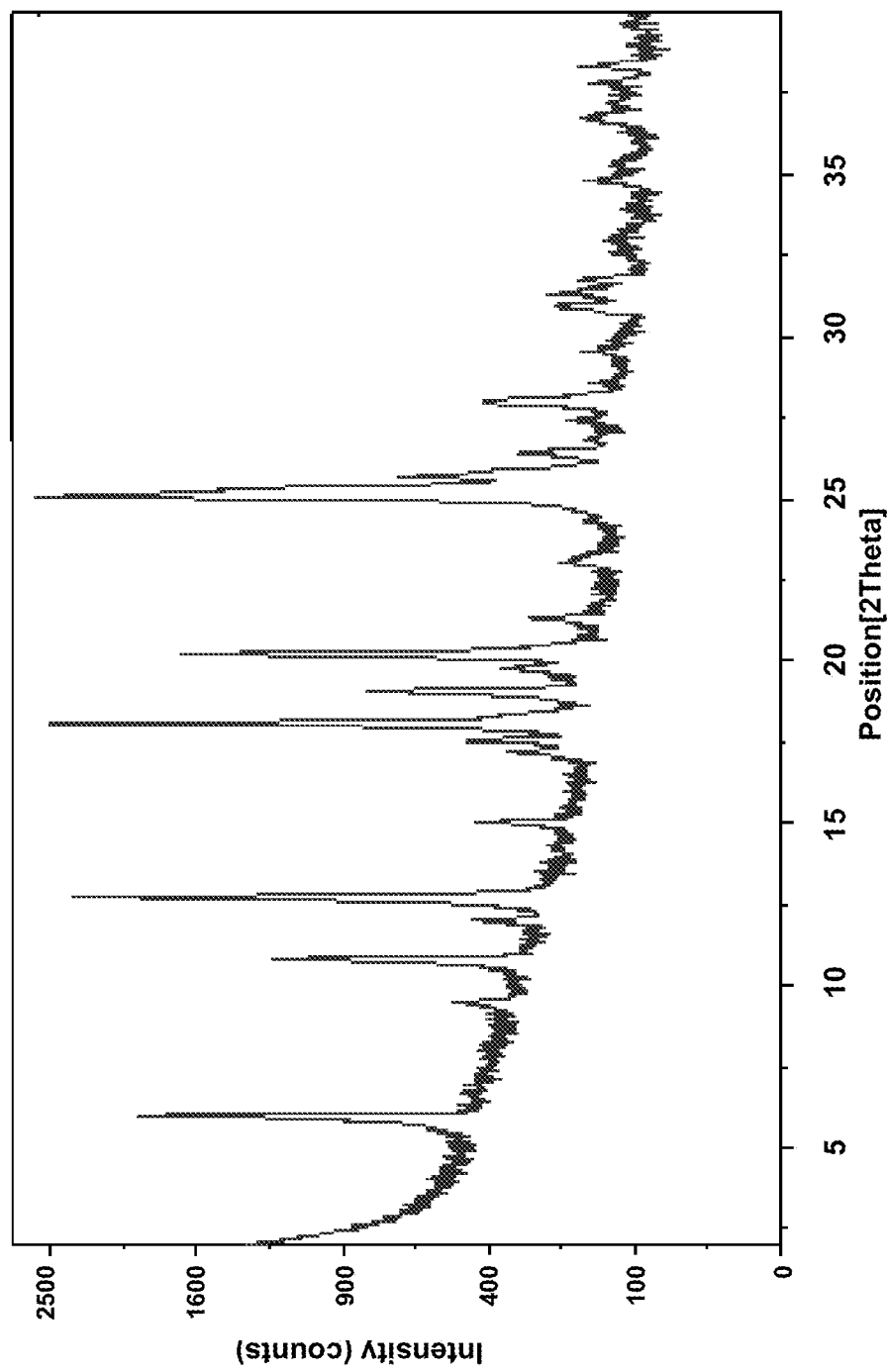
FIG. 24: PXRD diffractogram of N-methyl-1-(5-(thiophen-2-yl)tetrazolo[1,5-a]pyrazin-8-yl)azetidin-3-amine Hydrochloride Form 1, also known as Compound 2 Hydrochloric Salt Form 1.
Figure 25:
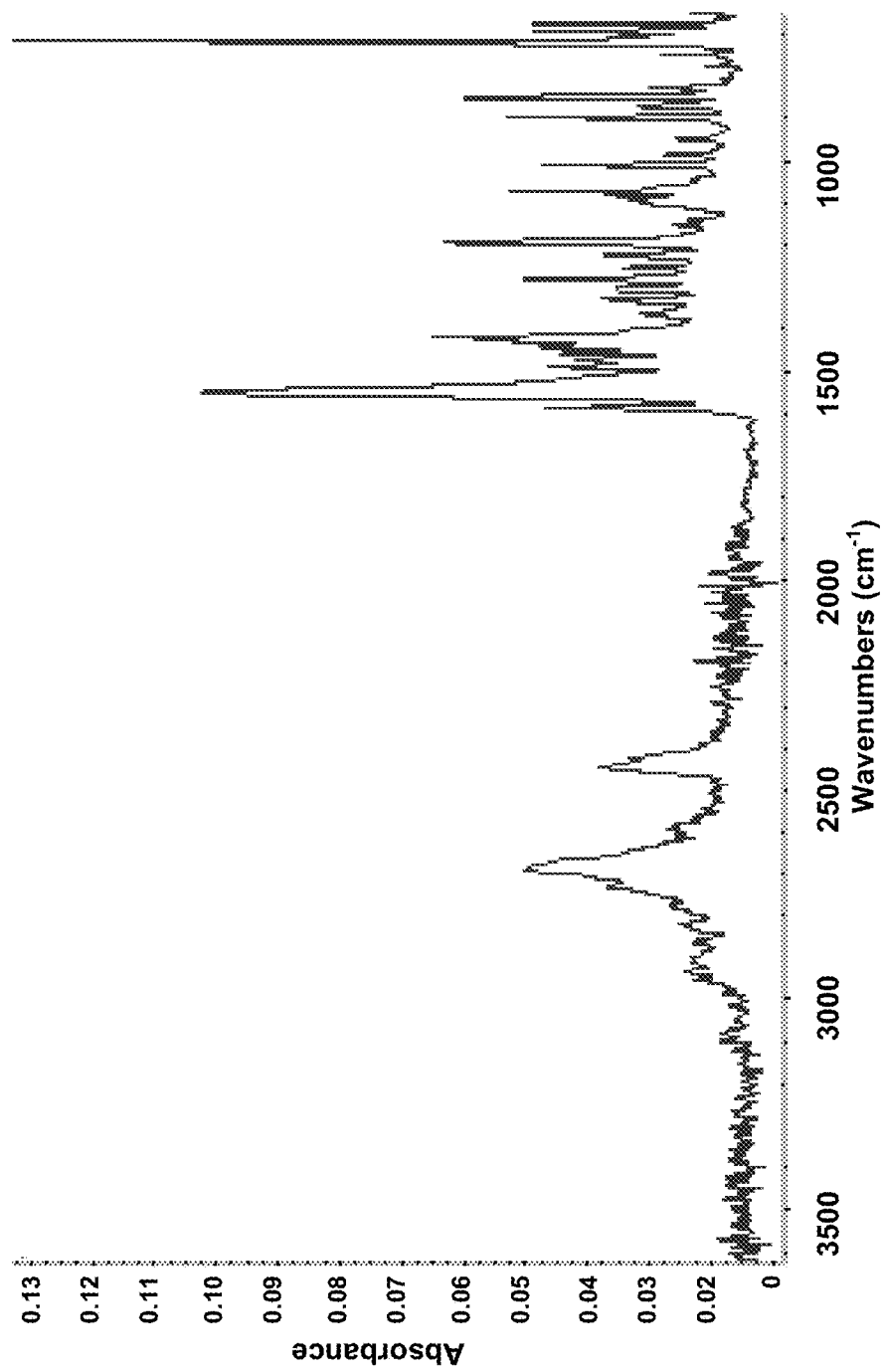
FIG. 25: FTIR Spectrum of N-methyl-1-(5-(thiophen-2-yl)tetrazolo[1,5-a]pyrazin-8-yl)azetidin-3-amine Hydrochloride Form 1, also known as Compound 2 Hydrochloride Salt Form 1.

(XX)

in a crystalline form;

In certain embodiments, the crystalline form of N-methyl-1-(5-(thiophen-2-yl)tetrazolo[1,5-a]pyrazin-8-yl)azetidin-3-amine Hydrochloride is characterized in that said form has at least one of the following characteristics:

an X-ray powder diffraction pattern with peaks at 6.0, 10.8, 12.7, 18.1, 20.2, 25.1 and 25.4 degrees two theta (±0.2 degree) (CuKα λ=1.54059 A), or an X-ray powder diffraction pattern substantially in accordance with that shown in FIG. 24; and an FTIR spectrum with the bands at 632, 715, 850, 1196, 1421, 1551 and 2689 cm$^{-1}$ or an FTIR spectrum substantially in accordance with that shown in FIG. 25.

In certain embodiments, provided herein is N-methyl-1-(5-(thiophen-2-yl)tetrazolo[1,5-a]pyrazin-8-yl)azetidin-3-amine Mesylate, having the structural formula (XXI)

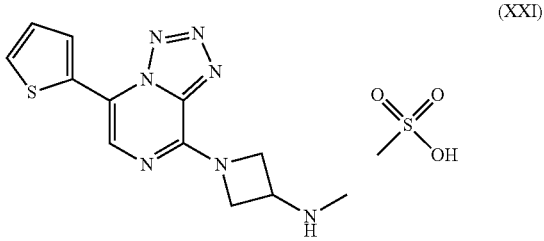

(XXI)

in a crystalline form.

Figure 29:
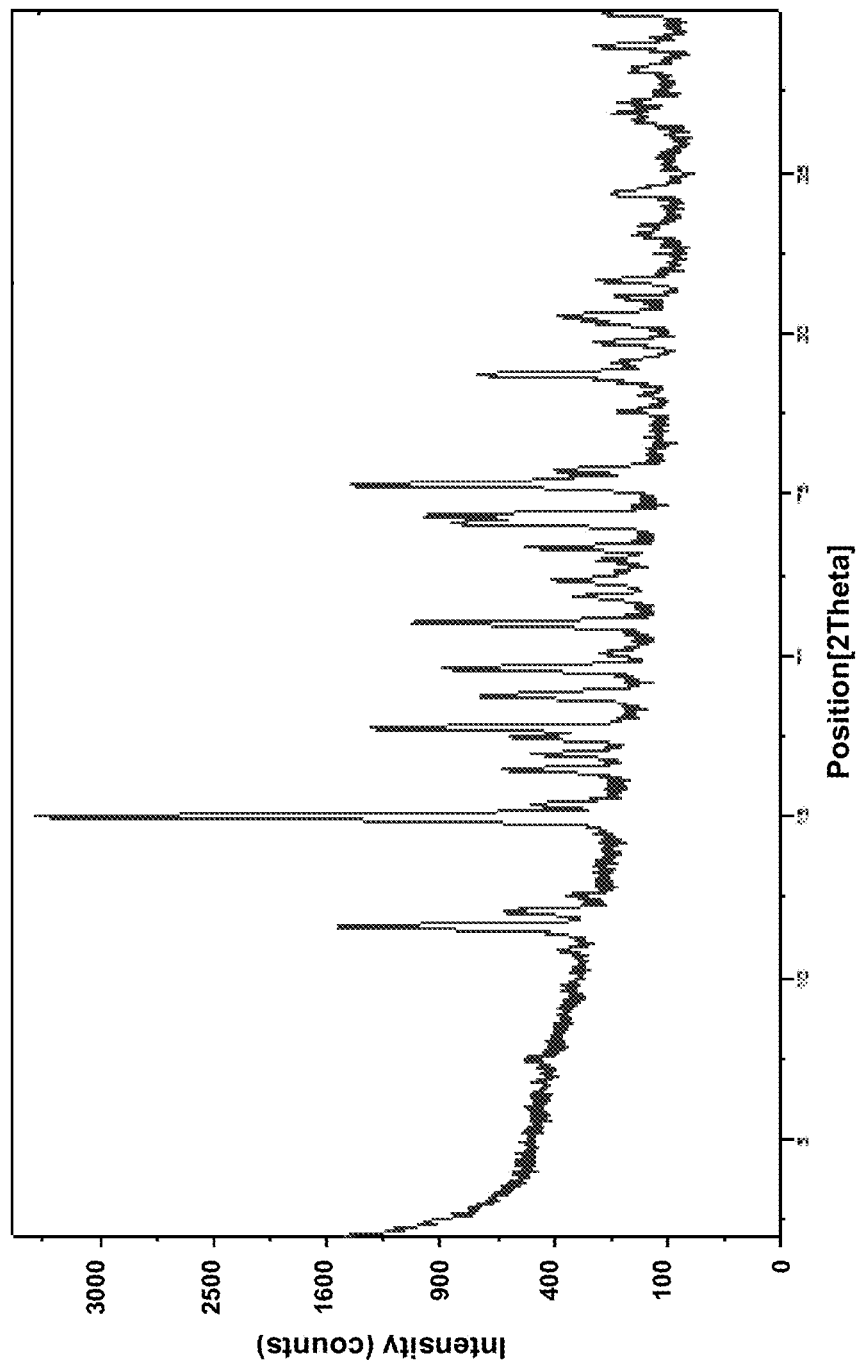
FIG. 29: PXRD diffractogram of N-methyl-1-(5-(thiophen-2-yl)tetrazolo[1,5-a]pyrazin-8-yl)azetidin-3-amine Mesylate Form 1, also known as Compound 2 Mesylate Salt Form 1.
Figure 30:
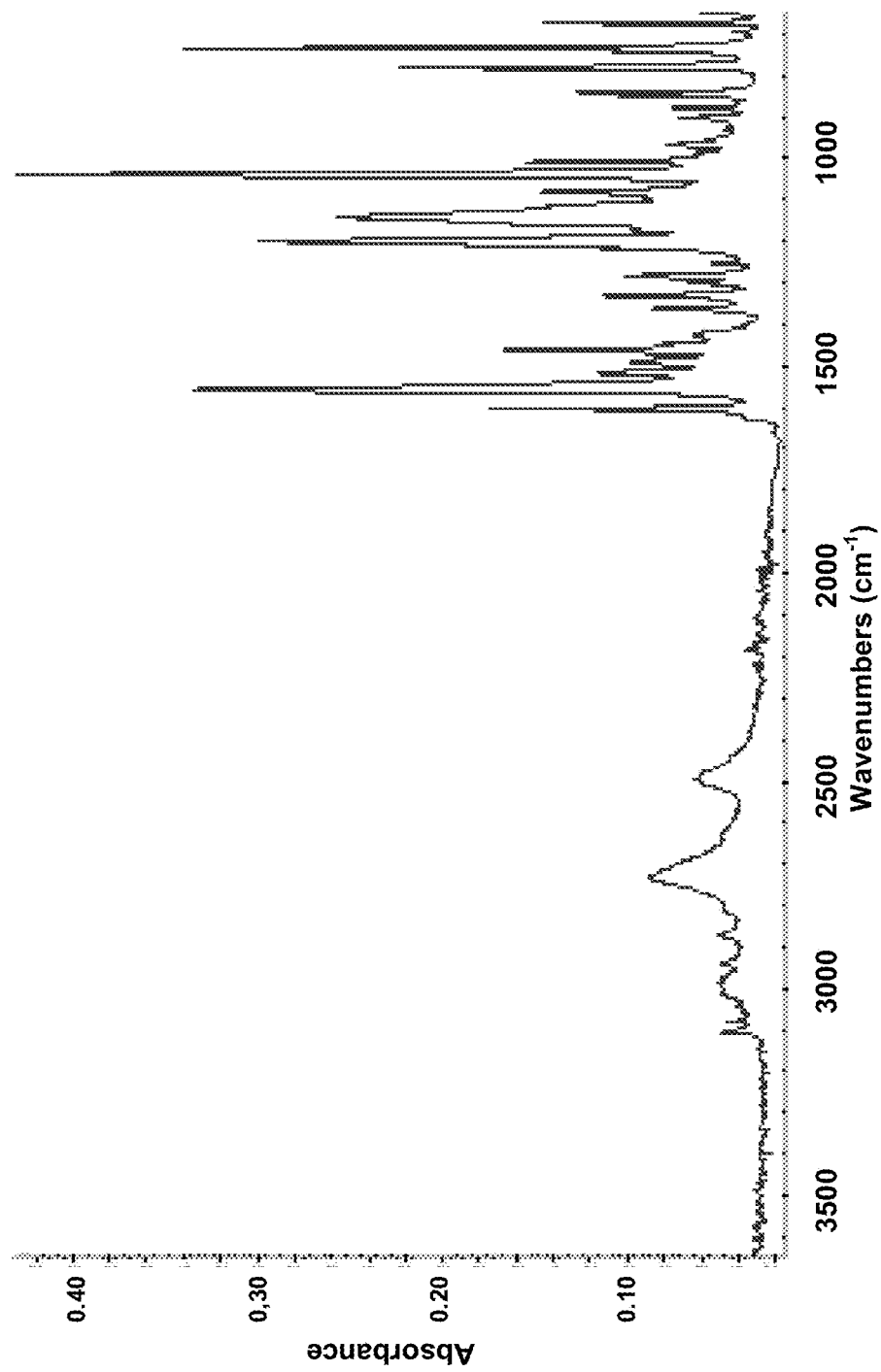
FIG. 30: FTIR Spectrum of N-methyl-1-(5-(thiophen-2-yl)tetrazolo[1,5-a]pyrazin-8-yl)azetidin-3-amine Mesylate Form 1, also known as Compound 2 Mesylate Salt Form 1.

In certain embodiments, the crystalline form of N-methyl-1-(5-(thiophen-2-yl)tetrazolo[1,5-a]pyrazin-8-yl)azetidin-3-amine Mesylate is characterized in that said form has at least one of the following characteristics:

an X-ray powder diffraction pattern with peaks at 11.6, 15.0, 17.7, 21.0, 24.3 and 25.2 degrees two theta (±0.2 degree) (CuKα λ=1.54059A), or an X-ray powder diffraction pattern substantially in accordance with that shown in FIG. 29; and an FTIR spectrum with the bands at 733, 781, 1038, 1140, 1199 and 1557 cm$^{-1}$ or an FTIR spectrum substantially in accordance with that shown in FIG. 30.

In certain embodiments, provided herein is a pharmaceutical composition comprising a compound, or a salt, polymorph or hydrate thereof, as disclosed herein, together with a pharmaceutically acceptable carrier.

In certain embodiments, the compound has structural Formula XII, disclosed above, together with a pharmaceutically acceptable carrier.

Also provided herein is a pharmaceutical composition comprising a compound chosen from 8-(4-methylpiperazin-1-yl)-5-(thiophen-2-yl)tetrazolo[1,5-a]pyrazine and N-methyl-1-(5-(thiophen-2-yl)tetrazolo[1,5-a]pyrazin-8-yl)azetidin-3-amine, or a salt, polymorph or hydrate thereof.

In certain embodiments, the compound is a salt and Y is chosen from tartrate, mesylate, citrate, and hydrochloride.

Also provided herein is a pharmaceutical composition comprising a salt, or a polymorph thereof, chosen from
8-(4-methylpiperazin-1-yl)-5-(thiophen-2-yl)tetrazolo[1,5-a]pyrazine tartrate hemihydrate;
8-(4-methylpiperazin-1-yl)-5-(thiophen-2-yl)tetrazolo[1,5-a]pyrazine tartrate monohydrate;
8-(4-methylpiperazin-1-yl)-5-(thiophen-2-yl)tetrazolo[1,5-a]pyrazine mesylate monohydrate;
N-methyl-1-(5-(thiophen-2-yl)tetrazolo[1,5-a]pyrazin-8-yl)azetidin-3-amine citrate;
N-methyl-1-(5-(thiophen-2-yl)tetrazolo[1,5-a]pyrazin-8-yl)azetidin-3-amine hydrochloride; and
N-methyl-1-(5-(thiophen-2-yl)tetrazolo[1,5-a]pyrazin-8-yl)azetidin-3-amine mesylate;
together with a pharmaceutically acceptable carrier.

In certain embodiments, the pharmaceutical composition comprises 8-(4-methylpiperazin-1-yl)-5-(thiophen-2-yl)tetrazolo[1,5-a]pyrazine mesylate monohydrate or a polymorph thereof, together with a pharmaceutically acceptable carrier.

In further embodiments, the pharmaceutical composition comprises 8-(4-methylpiperazin-1-yl)-5-(thiophen-2-yl)tetrazolo[1,5-a]pyrazine mesylate monohydrate Form 1, together with a pharmaceutically acceptable carrier.

In certain embodiments, the pharmaceutical composition comprises N-methyl-1-(5-(thiophen-2-yl)tetrazolo[1,5-a]pyrazin-8-yl)azetidin-3-amine hydrochloride, together with a pharmaceutically acceptable carrier.

In further embodiments, the pharmaceutical composition comprises N-methyl-1-(5-(thiophen-2-yl)tetrazolo[1,5-a]pyrazin-8-yl)azetidin-3-amine hydrochloride Form 1, together with a pharmaceutically acceptable carrier.

In certain embodiments, the pharmaceutical composition comprises N-methyl-1-(5-(thiophen-2-yl)tetrazolo[1,5-a]pyrazin-8-yl)azetidin-3-amine mesylate or a polymorph thereof, together with a pharmaceutically acceptable carrier.

In further embodiments, the pharmaceutical composition comprises N-methyl-1-(5-(thiophen-2-yl)tetrazolo[1,5-a]pyrazin-8-yl)azetidin-3-amine mesylate Form 1, together with a pharmaceutically acceptable carrier.

Also provided herein is a method of treatment of an H$_4$R-mediated disease comprising the administration, to a patient in need thereof, of a therapeutically effective amount of a compound as disclosed herein. In further embodiments, the method comprises the administration, to a patient in need thereof, of a therapeutically effective amount of a compound of Formula XII, disclosed above. All methods disclosed below also encompass the equivalent medical use of the compounds, including the compounds for use in the manufacture of medicaments for the treatment of disease.

In certain embodiments provided herein, said treatment is systemic.

In certain embodiments, said administration is topical.

In certain embodiments, said disease is chosen from an inflammatory disease, an autoimmune disease, an allergic disorder, and an ocular disorder.

In certain embodiments, disease is chosen from pruritus, eczema, atopic dermatitis, asthma, chronic obstructive pulmonary disease (COPD), allergic rhinitis, non-allergic rhinitis, rhinosinusitis, nasal inflammation, nasal congestion, sinus congestion, otic inflammation dry eye, ocular inflammation, allergic conjunctivitis, vernal conjunctivitis, vernal keratoconjunctivitis, and giant papillary conjunctivitis.

In further embodiments, the disease is chosen from pruritis, allergic rhinitis, non-allergic rhinitis, rhinosinusitis, nasal inflammation, nasal congestion, sinus congestion, nasal polyposis, asthma, COPD, allergic conjunctivitis, dry eye, and otic inflammation.

In certain embodiments, the compound of Formula XII is a salt and Y is chosen from tartrate, mesylate, citrate, and hydrochloride.

In certain embodiments, the compound of Formula XII is a salt, or a polymorph thereof, chosen from
8-(4-methylpiperazin-1-yl)-5-(thiophen-2-yl)tetrazolo[1,5-a]pyrazine tartrate hemihydrate;
8-(4-methylpiperazin-1-yl)-5-(thiophen-2-yl)tetrazolo[1,5-a]pyrazine tartrate monohydrate;
8-(4-methylpiperazin-1-yl)-5-(thiophen-2-yl)tetrazolo[1,5-a]pyrazine mesylate monohydrate;
N-methyl-1-(5-(thiophen-2-yl)tetrazolo[1,5-a]pyrazin-8-yl)azetidin-3-amine citrate;
N-methyl-1-(5-(thiophen-2-yl)tetrazolo[1,5-a]pyrazin-8-yl)azetidin-3-amine hydrochloride; and
N-methyl-1-(5-(thiophen-2-yl)tetrazolo[1,5-a]pyrazin-8-yl)azetidin-3-amine mesylate.

In certain embodiments, the method comprises the administration of a compound of Formula XII is chosen from 8-(4-methylpiperazin-1-yl)-5-(thiophen-2-yl)tetrazolo[1,5-a]pyrazine mesylate monohydrate Form 1, N-methyl-1-(5-(thiophen-2-yl)tetrazolo[1,5-a]pyrazin-8-yl)azetidin-3-amine hydrochloride Form 1, and N-methyl-1-(5-(thiophen-2-yl)tetrazolo[1,5-a]pyrazin-8-yl)azetidin-3-amine mesylate Form 1.

In certain embodiments, the administration is oral.
In certain embodiments, the administration is intravenous.

In certain embodiments, the administration is topical.

In certain embodiments, the topical administration is intranasal, otic, dermal, ophthalmic, or by inhalation.

In certain embodiments, said topical administration is to the skin.

In certain embodiments, said topical administration is to the eye.

In certain embodiments, the topical administration is intranasal.

In certain embodiments, the topical administration is intranasal and the compound is chosen from 8-(4-methylpiperazin-1-yl)-5-(thiophen-2-yl)tetrazolo[1,5-a]pyrazine mesylate monohydrate Form 1, N-methyl-1-(5-(thiophen-2-yl)tetrazolo[1,5-a]pyrazin-8-yl)azetidin-3-amine hydrochloride Form 1, and N-methyl-1-(5-(thiophen-2-yl)tetrazolo[1,5-a]pyrazin-8-yl)azetidin-3-amine mesylate Form 1.

Further provided herein is a method of treatment of allergic rhinitis comprising the topical, intranasal administration, to a patient in need thereof, of a therapeutically effective amount of 8-(4-methylpiperazin-1-yl)-5-(thiophen-2-yl)tetrazolo[1,5-a]pyrazine mesylate monohydrate, or a polymorph thereof.

In further embodiments, the 8-(4-methylpiperazin-1-yl)-5-(thiophen-2-yl)tetrazolo[1,5-a]pyrazine mesylate monohydrate is the Form 1 polymorph.

Also provided herein is a method of treatment of allergic rhinitis comprising the topical, intranasal administration, to a patient in need thereof, of a therapeutically effective amount of N-methyl-1-(5-(thiophen-2-yl)tetrazolo[1,5-a]pyrazin-8-yl)azetidin-3-amine hydrochloride, or a polymorph thereof.

In further embodiments, the N-methyl-1-(5-(thiophen-2-yl)tetrazolo[1,5-a]pyrazin-8-yl)azetidin-3-amine hydrochloride is the Form 1 polymorph.

Also provided herein is a method of treatment of the pain or inflammation resulting from eye surgery, comprising delivering to a patient in need of such treatment with a therapeutically effective amount of a salt or polymorph as disclosed herein. In certain embodiments, the eye surgery is chosen from cataract surgery and refractive surgery (including, e.g., Laser Assisted In-Situ Keratomileusis (LASIK), Laser Assisted Sub-Epithelium Keratomileusis (LASEK), photorefractive keratectomy, and various types of keratotomy and keratoplasty). In further embodiments, the disease is an allergic disorder. In further embodiments, the method comprises the administration, to a patient in need thereof, of a therapeutically effective amount of a compound of Formula XII, disclosed above.

Also provided herein is a method of inhibition of $H_4R$ signaling comprising contacting $H_4R$ with a compound, or a salt, hydrate, or polymorph thereof, as disclosed herein.

Also provided herein is a compound, or a salt, hydrate, or polymorph thereof, as recited in Claim 1 for use as a medicament. In certain embodiments, the compound has structural Formula XII, disclosed above.

Also provided herein is the use of a compound, or a salt, hydrate, or polymorph thereof, as disclosed herein in the manufacture of a medicament for the prevention or treatment of a disease or condition ameliorated by the inhibition of $H_4R$. In certain embodiments, the compound has structural Formula XII, disclosed above.

Also provided herein is a pharmaceutical composition comprising:
  a. a compound, or a salt, hydrate, or polymorph thereof, as recited herein;
  b. another therapeutic agent; and
  c. one or more pharmaceutically acceptable carriers or adjuvants.

In certain embodiments, the other therapeutic agent is an $H_1R$ antagonist.

In certain embodiments, the $H_1R$ antagonist is chosen from acrivastine, alcaftadine, antazoline, azelastine, bromazine, brompheniramine, cetirizine, chlorpheniramine, clemastine, desloratidine, diphenhydramine, diphenylpyraline, ebastine, emedastine, epinastine, fexofenadine, hydroxyzine, ketotifen, levocabastine, levocetirizine, loratidine, methdilazine, mizolastine, promethazine, olopatadine, and triprolidine.

In certain embodiments, the other therapeutic agent is an $H_3R$ antagonist.

In certain embodiments, the other therapeutic agents are an $H_3R$ antagonist and an $H_1R$ antagonist.

In certain embodiments, the other therapeutic agent is an intranasal corticosteroid.

In certain embodiments, the intranasal corticosteroid is chosen from fluticasone, budesonide, beclomethasone, mometasone and ciclesonide.

Also provided herein is a method of treatment of an $H_4R$-mediated disease comprising the administration, to a patient in need thereof, of a therapeutically effective amount of a compound, or a salt, hydrate, or polymorph thereof, as recited herein.

Also provided herein is a method of treatment of an $H_4R$-mediated disease comprising the administration of:
  a) a therapeutically effective amount of a salt or polymorph as recited herein; and
  b) another therapeutic agent.

Examples of other therapeutic agents and combinations are disclosed herein.

Also provided herein is a method for achieving an effect in a patient comprising the administration of a therapeutically effective amount of a salt or polymorph as recited herein to a patient, wherein the effect is chosen from reduction in the number of mast cells, inhibition of inflammatory cell (e.g., granulocytes including eosinophils, basophils, and neutrophils, mast cells, lymphocytes, and dendritic cells) migration optionally to the nasal mucosa, the ear, the eye, or the wound site, reduction in inflammatory markers, reduction in inflammatory cytokines, reduction in scratching, relief of symptoms and/or signs of nasal congestion from allergic and non-allergic causes, decreased watering or redness of the eyes, and reduction in ocular pain.

As used herein, the terms below have the meanings indicated.

The compound 8-(4-Methylpiperazin-1-yl)-5-(thiophen-2-yl)tetrazolo[1,5-a]pyrazine Monomethanesulfonate

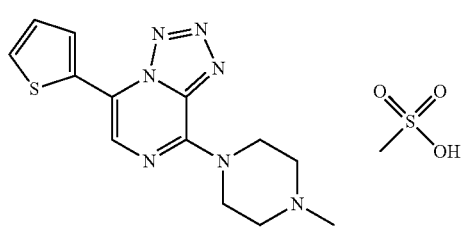

is also referred to as Compound 1 Monomethanesulfonate and Compound 1 Mesylate.

The compound 8-(4-Methylpiperazin-1-yl)-5-(thiophen-2-yl)tetrazolo[1,5-a]pyrazine Monomethanesulfonate monohydrate

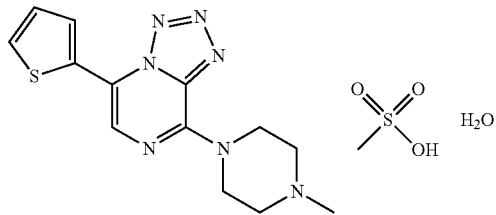

is also referred to as Compound 1 Monomethanesulfonate Monohydrate and Compound 1 Mesylate Monohydrate.

The compound 8-(4-Methylpiperazin-1-yl)-5-(thiophen-2-yl)tetrazolo[1,5-a]pyrazine Tartrate

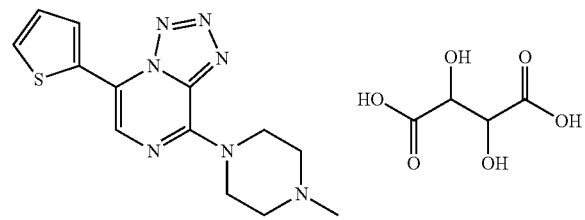 [SMILES: CN1CCN(c2ncc(-c3cccs3)n3nnnc23)CC1 ; O=C(O)C(O)C(O)C(=O)O]

is also referred to as Compound 1 Tartrate.

The compound 8-(4-Methylpiperazin-1-yl)-5-(thiophen-2-yl)tetrazolo[1,5-a]pyrazine Tartrate Monohydrate

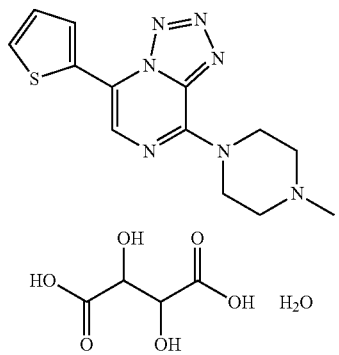

is also referred to as Compound 1 Tartrate Monohydrate.

The compound 8-(4-Methylpiperazin-1-yl)-5-(thiophen-2-yl)tetrazolo[1,5-a]pyrazine Tartrate Hemihydrate

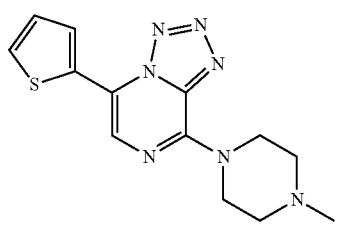

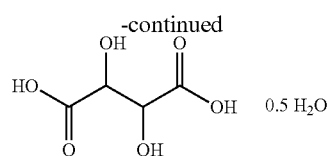

is also referred to as Compound 1 Tartrate Hemihydrate.

The compound N-methyl-1-(5-(thiophen-2-yl)tetrazolo[1,5-a]pyrazin-8-yl)azetidin-3-amine Hydrochloride

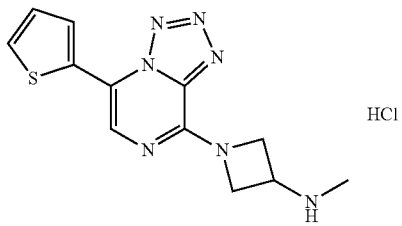 [SMILES: CNC1CN(c2ncc(-c3cccs3)n3nnnc23)C1 ; Cl]

is also referred to as Compound 2 Hydrochloride.

The compound N-methyl-1-(5-(thiophen-2-yl)tetrazolo[1,5-a]pyrazin-8-yl)azetidin-3-amine Monomethanesulfonate

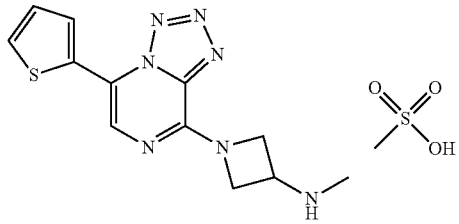

is also referred to as Compound 2 Monomethanesulfonate and Compound 2 Mesylate.

The compound N-methyl-1-(5-(thiophen-2-yl)tetrazolo[1,5-a]pyrazin-8-yl)azetidin-3-amine Citrate

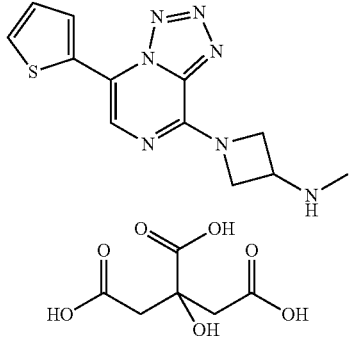

is also referred to as Compound 2 Citrate.

Compounds Disclosed

When ranges of values are disclosed, and the notation "from $n_1$ ... to $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety where the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon group having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH=CH—),(—C::C—)]. Examples of suitable alkenyl groups include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether group, wherein the term alkyl is as defined below. Examples of suitable alkyl ether groups include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl group containing from 1 to 20 carbon atoms. In certain embodiments, said alkyl group will comprise from 1 to 10 carbon atoms. In further embodiments, said alkyl group will comprise from 1 to 6 carbon atoms. Alkyl groups may be optionally substituted as defined herein. Examples of alkyl groups include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) group wherein the term alkyl is as defined above and wherein the sulfur may be singly or doubly oxidized. Examples of suitable alkyl thioether groups include methylthio, ethylthio, n-propylthio, iso-propylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon group having one or more triple bonds and containing from 2 to 20 carbon atoms. In certain embodiments, said alkynyl group comprises from 2 to 6 carbon atoms. In further embodiments, said alkynyl group comprises from 2 to 4 carbon atoms. The term "alkynylene" refers to a carbon-carbon triple bond attached at two positions such as ethynylene (—C:::C—, —C≡C—). Examples of alkynyl groups include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(=O)—NR$_2$ group with R as defined herein. The term "N-amido" as used herein, alone or in combination, refers to a RC(=O)NH— group, with R as defined herein. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR', wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl group derived from an aryl-substituted alkanecarboxylic acid such as benzoyl, naphthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent group C$_6$H$_4$= derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR' group, with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronaphthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl group having the meaning as defined above wherein one or more hydrogens are replaced with a halogen. Specifically embraced are monohaloalkyl, dihaloalkyl and polyhaloalkyl groups. A monohaloalkyl group, for one example, may have an iodo, bromo, chloro or fluoro atom within the group. Dihalo and polyhaloalkyl groups may have two or more of the same halo atoms or a combination of different halo groups. Examples of haloalkyl groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or cyclic hydrocarbon group, or combinations thereof, fully saturated or containing from 1 to 3 degrees of unsaturation, consisting of the stated number of carbon atoms and from one to three heteroatoms chosen from O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 7 membered unsaturated heteromonocyclic ring, or a fused monocyclic, bicyclic, or tricyclic ring system in which at least one of the fused rings is aromatic, which contains at least one atom chosen from O, S, and N. In certain embodiments, said heteroaryl will comprise from 5 to 7 carbon atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic group containing at least one heteroatom as a ring member, wherein each said heteroatom may be independently chosen from nitrogen, oxygen, and sulfur. In certain embodiments, said heterocycloalkyl will comprise from 1 to 4 heteroatoms as ring members. In further embodiments, said heterocycloalkyl will comprise from 1 to 2 heteroatoms as ring members. In certain embodiments, said heterocycloalkyl will comprise from 3 to 8 ring members in each ring. In further embodiments, said heterocycloalkyl will comprise from 3 to 7 ring members in each ring. In yet further embodiments, said heterocycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The term "isocyanato" refers to a —NCO group.

The term "isothiocyanato" refers to a —NCS group.

The term "lower," as used herein, alone or in a combination, where not otherwise specifically defined, means containing from 1 to and including 6 carbon atoms.

The term "lower aryl," as used herein, alone or in combination, means phenyl or naphthyl, which may be optionally substituted as provided.

The term "lower heteroalkyl," as used herein, alone or in combination, refers to a stable straight or branched chain, or cyclic hydrocarbon group, or combinations thereof, fully saturated or containing from 1 to 3 degrees of unsaturation, consisting of one to six atoms in which one to three may be heteroatoms chosen from O, N, and S, and the remaining atoms are carbon. The nitrogen and sulfur atoms may optionally be oxidized and the nitrogen heteroatom may optionally be quaternized. The heteroatom(s) O, N and S may be placed at any interior or terminal position of the heteroalkyl group. Up to two heteroatoms may be consecutive, such as, for example, —CH$_2$—NH—OCH$_3$.

The term "lower heteroaryl," as used herein, alone or in combination, means either 1) monocyclic heteroaryl comprising five or six ring members, of which between one and four said members may be heteroatoms chosen from O, S, and N, or 2) bicyclic heteroaryl, wherein each of the fused rings comprises five or six ring members, comprising between them one to four heteroatoms chosen from O, S, and N.

The term "lower cycloalkyl," as used herein, alone or in combination, means a monocyclic cycloalkyl having between three and six ring members. Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms chosen from O, S, and N. Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently chosen from hydrogen, lower alkyl, and lower heteroalkyl, any of which may be optionally substituted. Additionally, the R and R' of a lower amino group may combine to form a five- or six-membered heterocycloalkyl, either of which may be optionally substituted.

The term "mercaptyl" as used herein, alone or in combination, refers to an RS— group, where R is as defined herein.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer to the —SO$_3$H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)$_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR' group with R and R' as defined herein.

The term "thiocyanato" refers to a —CNS group.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, N$_3$, SH, SCH$_3$, C(O)CH$_3$, CO$_2$CH$_3$, CO$_2$H, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R'' where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The term "inhibition" (and by extension, "inhibitor") as used herein encompasses all forms of functional protein (enzyme, kinase, receptor, channel, etc., for example) inhibition, including neutral antagonism, inverse agonism, competitive inhibition, and non-competitive inhibition (such as allosteric inhibition). Inhibition may be phrased in terms of an IC$_{50}$, defined below. Compounds disclosed herein may be H$_4$R allosteric antagonists that are non competitive with histamine. Additionally, compounds disclosed herein may be agonists in one species and antagonists in another. Methods are known in the art, and are disclosed herein and can be adapted by those of skill in the art, to ascertain whether a compound is, for example, a suitable H$_4$R antagonist in a species of interest.

In certain embodiments, "H$_1$R inhibitor" is used herein to refer to a compound that exhibits an IC$_{50}$ with respect to the histamine type-1 receptor of no more than about 100 µM and more typically not more than about 50 µM, as measured in the in vitro histamine receptor cell-based assays described generally hereinbelow.

Similarly, "H$_3$R inhibitor" is used herein to refer to a compound that exhibits an IC$_{50}$ with respect to the histamine type-3 receptor of no more than about 100 µM and more typically not more than about 50 µM, as measured in the in vitro histamine receptor cell-based assays described generally hereinbelow.

Also similarly, "H$_4$R inhibitor" is used herein to refer to a compound that exhibits an IC$_{50}$ with respect to the histamine type-4 receptor of no more than about 100 µM and more typically not more than about 50 µM, as measured in the in vitro histamine receptor cell-based assays described generally hereinbelow.

A "H$_1$/H$_4$ inhibitor" is used herein to refer to a compound that exhibits an IC$_{50}$ with respect to both the histamine type-1 receptor and the histamine type-4 receptor of no more than about 100 µM and more typically not more than about 50 µM, as measured in the in vitro histamine receptor cell-based assays described generally hereinbelow; the amount of inhibition need not be equivalent at each receptor, but should not be negligible.

In certain embodiments, such as, for example, in the case of an in vitro ligand-binding assay protocol, "IC$_{50}$" is that concentration of compound which is required to displace a natural ligand or reference standard to a half-maximal level. In other embodiments, such as, for example, in the case of certain cellular or in vivo protocols which have a functional readout, "IC$_{50}$" is that concentration of compound which reduces the activity of a functional protein (e.g., H$_1$R and/or H$_4$R) to a half-maximal level. In either of these scenarios, the term "EC$_{50}$" may also be used. In vitro or in vivo, "EC$_{50}$"

refers to the concentration of a compound required to achieve half of the maximal effect in an assay or protocol, typically as compared to a reference standard.

Certain compounds disclosed herein have been discovered to exhibit inhibitory activity against $H_4R$. In certain embodiments, compounds will exhibit an $IC_{50}$ with respect to $H_4R$ of no more than about 10 µM; in further embodiments, compounds will exhibit an $IC_{50}$ with respect to $H_4R$ of no more than about 5 µM; in yet further embodiments, compounds will exhibit an $IC_{50}$ with respect to $H_4R$ of not more than about 1 µM; in yet further embodiments, compounds will exhibit an $IC_{50}$ with respect to $H_4R$ of not more than about 200 nM, as measured in an $H_4R$ assay such as that described herein.

The phrase "therapeutically effective" is intended to qualify the amount of active ingredients used in the treatment of a disease or disorder. This amount will achieve the goal of reducing or eliminating the said disease or disorder.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. The term "patient" means all mammals including humans. Examples of patients include humans, cows, dogs, cats, goats, sheep, pigs, and rabbits. Preferably, the patient is a human.

The term "compound," as used herein, includes salts, solvates and polymorphs of the compound, as well as the free base. In certain embodiments, the solvate is a hydrate. A solvate is a stable, solid or semi-solid form of a compound that comprises either a non-stoichiometric or a stoichimetric equivalent of solvent. If the solvent is water, the solvate is a hydrate. In certain embodiments, the hydrate has a stoichimetric equivalent of water chosen from about 0, about 0.5, and about 1 $H_2O$; that is, the hydrate is anhydrous, a hemihydrate, or a monohydrate. Non-stoichiometric hydrates and stoichiometric hydrates are both contemplated. As further discussed below, a polymorph is a distinct crystalline form of a compound. A compound may be, for example, a polymorph of a free base, a polymorph of a salt, a polymorph of a hydrate, or a polymorph of a hydrate of a salt of a compound, and so forth.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

Suitable salts include pharmaceutically acceptable salts formed with counterions deriving from both organic and inorganic acids as well as metals. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate (including monomethanesulfonate, or mesylate), naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Salts disclosed herein may combine in 1:1 molar ratios, and in fact this is often how they are initially synthesized. However, it will be recognized by one of skill in the art that the stoichiometry of one ion in a salt to the other may be otherwise. Salts shown herein may be, for the sake of convenience in notation, shown in a 1:1 ratio; all possible stoichiometric arrangements are encompassed by the scope of the present invention.

When the phrase "Y is a counterion" is used in structural formulas herein, and neither the compound nor the counterion is drawn showing explicit ionic character, such ionic character may be inferred and a corresponding charges on each moiety be assumed to be present or absent. For example, if X is a monovalent cation such as $Mg(OH)^+$, it may be inferred that the coupled compound has lost a proton to form an ionic bond with X, despite Formula I being drawn to explicitly show all protons in place. Similarly, when X is an anion, the coupled compound takes on cationic character. The notation is left intentionally ambiguous as to placement and ratios of charges since without extensive physical characterization, such as X-ray crystal diffraction, it is often difficult to know with certainty where on a compound a counterion has bound. Additionally, counterions and compounds may combine in uneven molar ratios to form solid salts.

The terms, "polymorphs" and "polymorphic forms" and related terms herein refer to crystal forms of the same molecule. Polymorphs may be formed from both the free bases or free acids of compounds, or of salts of compounds, or of hydrates of compounds or their salts. Different polymorphs may have different physical properties such as, for example, melting temperatures, heats of fusion, solubilities, dissolution rates and/or vibrational spectra as a result of the arrangement or conformation of the molecules in the crystal lattice. The differences in physical properties exhibited by polymorphs affect pharmaceutical parameters such as storage stability, compressibility and density (important in formulation and product manufacturing), and dissolution rates (an important factor in bioavailability). Differences in stability can result from changes in chemical reactivity (e.g. differential oxidation, such that a dosage form discolors more rapidly when comprised of one polymorph than when comprised of another polymorph) or mechanical changes (e.g. tablets crumble on storage as a kinetically favored polymorph converts to thermodynamically more stable polymorph) or both (e.g., tablets of one polymorph are more susceptible to breakdown at high humidity). As a result of solubility/dissolution differences, in the extreme case, some polymorphic transitions may result in lack of potency or, at the other extreme, toxicity. In addition, the physical properties of the crystal may be important in processing, for example, one polymorph might be more likely to form solvates or might be difficult to filter and wash free of impurities (i.e., particle shape and size distribution might be different between polymorphs).

Polymorphic forms described herein may include forms such as Form 1, Form 2, form 3, amorphous, and the like. These terms encompass polymorphs that are substantially similar to those described herein. In this context, "substantially similar" means that one of skill in the art would recognize the polymorphs differing insignificantly from those polymorphs as physically characterized herein, or those polymorphs having one or more properties described herein. By way of example, a polymorph encompassed by the term Form 1 could have an X-ray powder diffraction (PXRD) spectrum which is at least 70%, at least 80%, at least 90%, or at least 95% identical to that shown in the PXRD for Form 1. For example, the encompassed polymorph might have at least 80% of the peaks in common with the disclosed Form 1. Alternatively, if the PXRD spectrum is identified by only a few major peaks, the encompassed polymorph might have major peaks at least 80% identical to those shown in a PXRD spectrum. Alternatively, the encompassed polymorph might have an aqueous solubility which is within 80 to 120% that shown herein.

Polymorphs of a molecule can be obtained by a number of methods, as known in the art. Such methods include, but are not limited to, melt recrystallization, melt cooling, solvent recrystallization, desolvation, rapid evaporation, rapid cooling, slow cooling, vapor diffusion and sublimation.

Techniques for characterizing polymorphs include, but are not limited to, differential scanning calorimetry (DSC), X-ray powder diffractometry (PXRD), thermal gravimetric analysis (TGA), dynamic vapor sorption/desorption (DVS), single crystal X-ray diffractometry, vibrational spectroscopy, e.g. IR and Raman spectroscopy, solid state NMR, hot stage optical microscopy, scanning electron microscopy (SEM), electron crystallography and quantitative analysis, particle size analysis (PSA), surface area analysis, solubility studies and dissolution studies.

The term, "solvate," as used herein, refers to a crystal form of a substance which contains solvent. The term "hydrate" refers to a solvate wherein the solvent is water.

The term, "desolvated solvate," as used herein, refers to a crystal form of a substance which can only be made by removing the solvent from a solvate.

The term "amorphous form," as used herein, refers to a noncrystalline form of a substance.

The term "solubility" is generally intended to be synonymous with the term "aqueous solubility," and refers to the ability, and the degree of the ability, of a compound to dissolve in water or an aqueous solvent or buffer, as might be found under physiological conditions. Aqueous solubility is, in and of itself, a useful quantitative measure, but it has additional utility as a correlate and predictor, with some limitations which will be clear to those of skill in the art, of oral bioavailability. In practice, a soluble compound is generally desirable, and the more soluble, the better. There are notable exceptions; for example, certain compounds intended to be administered as depot injections, if stable over time, may actually benefit from low solubility, as this may assist in slow release from the injection site into the plasma. Solubility is typically reported in mg/mL, but other measures, such as g/g, may be used. Solubilities typically deemed acceptable may range from 1 mg/mL into the hundreds or thousands of mg/mL.

Solubility may be measured under varying conditions. For example, it may be measured under conditions similar to those found in the body, such as at gastric pH, physiologic or near-physiologic pH, or nasal mucosa pH. "Gastric pH" as used herein means about pH 1. "Near-physiologic pH," as used herein refers to the typical pH of bodily tissues and fluids, such as blood and plasma, or cytoplasm, generally about 7.4. "Nasal mucosa pH" as used herein means from about pH 3.5 to about pH 7.6.

As used herein, "solid" when referring to a salt form means relatively solid, at room temperature, and/or containing a substantial amount of solids. A solid may be amorphous in form and/or be a solvated solid with some quantity of residual or coordinated of solvent molecules. A crystalline salt is an example of a solid. By way of example, a wax could be considered a solid, whereas an oil would not be.

A "solid composition" as used herein includes a salt of a compound, or a polymorph or amorphous solid form thereof.

While it may be possible for the salts or polymorphs disclosed hereinto be administered as the raw chemical, it is also possible to present them as a pharmaceutical formulation. Accordingly, provided herein are pharmaceutical formulations which comprise one or more of certain salts or polymorphs disclosed herein, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual, ocular, intranasal, and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a salt or polymorph as disclosed herein ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the salts or polymorphs disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Examples of fillers or diluents for use in oral pharmaceutical formulations such as capsules and tablets include, without limitation, lactose, mannitol, xylitol, dextrose, sucrose, sorbitol, compressible sugar, microcrystalline cellulose (MCC), powdered cellulose, cornstarch, pregelatinized starch, dextrates, dextran, dextrin, dextrose, maltodextrin, calcium carbonate, dibasic calcium phosphate, tribasic calcium phosphate, calcium sulfate, magnesium carbonate, magnesium oxide, poloxamers such as polyethylene oxide, and hydroxypropyl methyl cellulose. Fillers may have complexed solvent molecules, such as in the case where the lactose used is lactose monohydrate. Fillers may also be proprietary, such in the case of the filler PROSOLV® (available from JRS Pharma). PROSOLV is a proprietary, optionally high-density, silicified microcrystalline cellulose composed of 98% microcrystalline cellulose and 2% colloidal silicon dioxide. Silicification of the microcrystalline cellulose is achieved by a patented process, resulting in an intimate association between the colloidal silicon dioxide and microcrystalline cellulose. ProSolv comes in different grades based on particle size, and is a white or almost white, fine or granular powder, practically insoluble in water, acetone, ethanol, toluene and dilute acids and in a 50 g/l solution of sodium hydroxide.

Examples of disintegrants for use in oral pharmaceutical formulations such as capsules and tablets include, without limitation, sodium starch glycolate, sodium carboxymethyl cellulose, calcium carboxymethyl cellulose, croscarmellose sodium, povidone, crospovidone (polyvinylpolypyrrolidone), methyl cellulose, microcrystalline cellulose, powdered cellulose, low-substituted hydroxy propyl cellulose, starch, pregelatinized starch, and sodium alginate.

Additionally, glidants and lubricants may be used in oral pharmaceutical formulations to ensure an even blend of excipients upon mixing. Examples of lubricants include, without limitation, calcium stearate, glyceryl monostearate, glyceryl palmitostearate, hydrogenated vegetable oil, light mineral oil, magnesium stearate, mineral oil, polyethylene glycol, sodium benzoate, sodium lauryl sulfate, sodium stearyl fumarate, stearic acid, talc, and zinc stearate. Examples of glidants include, without limitation, silicon dioxide ($SiO_2$), talc cornstarch, and poloxamers. Poloxamers (or LUTROL®, available from the BASF Corporation) are A-B-A block copolymers in which the A segment is a hydrophilic polyethylene glycol homopolymer and the B segment is hydrophobic polypropylene glycol homopolymer.

Examples of tablet binders include, without limitation, acacia, alginic acid, carbomer, carboxymethyl cellulose sodium, dextrin, ethylcellulose, gelatin, guar gum, hydrogenated vegetable oil, hydroxyethyl cellulose, hydroxypropyl cellulose, hydroxypropylmethyl cellulose, copolyvidone, methyl cellulose, liquid glucose, maltodextrin, polymethacrylates, povidone, pregelatinized starch, sodium alginate, starch, sucrose, tragacanth, and zein.

The salts or polymorphs may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the salts or polymorphs which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the salts or polymorphs to allow for the preparation of highly concentrated solutions.

In addition to the formulations described previously, the salts or polymorphs may also be formulated as depot preparations. Such long acting formulations may be administered by implantation (for example subcutaneously or intramuscularly) or by intramuscular injection. Thus, for example, the salts or polymorphs may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The salts or polymorphs may also be formulated in rectal compositions such as suppositories or retention enemas, e.g., containing conventional suppository bases such as cocoa butter, polyethylene glycol, or other glycerides.

Salts or polymorphs disclosed herein may be administered topically, that is by non-systemic administration. This includes the application of a salt or polymorph disclosed herein externally to the epidermis or the buccal cavity and the instillation of such a salt or polymorph into the ear, eye and nose, such that the salt or polymorph does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 2% w/w of the formulation.

Topical ophthalmic, otic, and nasal formulations may comprise excipients in addition to the active ingredient. Excipients commonly used in such formulations include, but are not limited to, tonicity agents, preservatives, chelating agents, buffering agents, and surfactants. Other excipients comprise solubilizing agents, stabilizing agents, comfort-enhancing agents, polymers, emollients, pH-adjusting agents and/or lubricants. Any of a variety of excipients may be used in formulations disclosed herein including water, mixtures of water and water-miscible solvents, such as C1-C7-alkanols, vegetable oils or mineral oils comprising from 0.5 to 5% non-toxic water-soluble polymers, natural products, such as alginates, pectins, tragacanth, karaya gum, guar gum, xanthan gum, carrageenin, agar and acacia, starch derivatives, such as starch acetate and hydroxypropyl starch, and also other synthetic products such as polyvinyl alcohol, polyvinylpyrrolidone, polyvinyl methyl ether, polyethylene oxide, preferably cross-linked polyacrylic acid and mixtures of those products. The concentration of the excipient is, typically, from 1 to 100,000 times the concentration of the active ingredient. In preferred embodiments, the excipients to be included in the formulations are typically selected on the basis of their inertness towards the active ingredient component of the formulations.

Relative to ophthalmic, otic, and nasal formulations, suitable tonicity-adjusting agents include, but are not limited to, mannitol, dextrose, sodium chloride, glycerin, sorbitol and the like. Suitable buffering agents include, but are not limited to, phosphates, citrates, borates, acetates and the like. Suitable surfactants include, but are not limited to, ionic and nonionic surfactants (though nonionic surfactants are preferred), polysorbate 80, RLM 100, POE 20 cetylstearyl ethers such as Procol® CS20 and poloxamers such as Pluronic® F68. Formulations may contain substances which increase the viscosity of the solution or suspension, such as sodium carboxymethyl cellulose, hypromellose, micro crystalline cellulose, sorbitol, or dextran. Optionally, the formulation may also contain suitable stabilizers or agents which increase the solubility of the salts or polymorphs to allow for the preparation of highly concentrated solutions, including but not limited to ethanol, benzyl alcohol, polyethylene glycol, phenylethyl alcohol and glycerin.

The formulations set forth herein may comprise one or more preservatives. Examples of such preservatives include benzalkonium chloride, p-hydroxybenzoic acid ester, sodium perborate, sodium chlorite, alcohols such as chlorobutanol, benzyl alcohol or phenyl ethanol, guanidine derivatives such as polyhexamethylene biguanide, sodium perborate, polyquaternium-1, amino alcohols such as AMP-95, or sorbic acid. In certain embodiments, the formulation may be self-preserved so that no preservation agent is required.

For ophthalmic, otic, or nasal administration, the formulation may be a solution, a suspension, or a gel. In preferred aspects, the formulations are for topical application to the eye, or ear are in aqueous solution or suspension in the form of drops. Formulations for topical application to the nose in aqueous solution or suspension are in the form of drops, spray or aerosol. The term "aqueous" typically denotes an aqueous formulation wherein the formulation is >50%, more preferably >75% and in particular >90% by weight water. The drops, spray or aerosol may be delivered from a single dose ampoule which may preferably be sterile and thus render bacteriostatic components of the formulation unnecessary. Alternatively, the drops, spray or aerosol may be delivered from a multi-dose bottle which may preferably comprise a device which extracts any preservative from the formulation as it is delivered, such devices being known in the art. Solution and suspension formulations may be nasally administered using a nebulizer. Intranasal delivery as a solution, suspension or dry powder may also facilitated by propellant-based aerosol systems, which include but are not limited to hydrofluoroalkane-based propellants. Alternatively the active pharmaceutical ingredient may be delivered in the form of a dry powder.

For ophthalmic disorders, components may be delivered to the eye as a concentrated gel or a similar vehicle, or as dissolvable inserts that are placed beneath the eyelids.

The formulations disclosed herein that are adapted for topical administration to the eye are preferably isotonic, or slightly hypotonic in order to combat any hypertonicity of tears caused by evaporation and/or disease. This may require a tonicity agent to bring the osmolality of the formulation to a level at or near 210-320 milliosmoles per kilogram (mOsm/kg). These formulations generally have an osmolality in the range of 220-320 mOsm/kg, and preferably have an osmolality in the range of 235-300 mOsm/kg. The ophthalmic formulations will generally be formulated as sterile aqueous solutions.

In certain ophthalmic embodiments, the compositions disclosed herein are formulated with one or more tear substitutes. A variety of tear substitutes are known in the art and include, but are not limited to: monomeric polyols, such as, glycerol, propylene glycol, and ethylene glycol; polymeric polyols such as polyethylene glycol; cellulose esters such hydroxypropylmethyl cellulose, carboxy methylcellulose sodium and hydroxy propylcellulose; dextrans such as dextran 70; vinyl polymers, such as polyvinyl alcohol; and carbomers, such as carbomer 934P, carbomer 941, carbomer 940 and carbomer 974P. Certain formulations disclosed herein may be used with contact lenses or other ophthalmic products.

Preferred formulations are prepared using a buffering system that maintains the formulation at a pH of about 4.5 to a pH of about 8. A most preferred formulation pH is from 5.5 to 7.5.

In certain embodiments, a formulation disclosed herein is administered once a day. However, the formulations may also be formulated for administration at any frequency of administration, including once a week, once every 5 days, once every 3 days, once every 2 days, twice a day, three times a day, four times a day, five times a day, six times a day, eight times a day, every hour, or any greater frequency. Such dosing frequency is also maintained for a varying duration of time depending on the therapeutic regimen. The duration of a particular therapeutic regimen may vary from one-time dosing to a regimen that extends for months or years. The formulations are administered at varying dosages, but typical dosages are one to two drops at each administration, or a comparable amount of a gel or other formulation. One of ordinary skill in the art would be familiar with determining a therapeutic regimen for a specific indication.

Gels for topical or transdermal administration may comprise, generally, a mixture of volatile solvents, nonvolatile solvents, and water. In certain embodiments, the volatile solvent component of the buffered solvent system may include lower (C1-C6) alkyl alcohols, lower alkyl glycols and lower glycol polymers. In further embodiments, the volatile solvent is ethanol. The volatile solvent component is thought to act as a penetration enhancer, while also producing a cooling effect on the skin as it evaporates. The nonvolatile solvent portion of the buffered solvent system is selected from lower alkylene glycols and lower glycol polymers. In certain embodiments, propylene glycol is used. The nonvolatile solvent slows the evaporation of the volatile solvent and reduces the vapor pressure of the buffered solvent system. The amount of this nonvolatile solvent component, as with the volatile solvent, is determined by the active ingredient or drug being used. When too little of the nonvolatile solvent is in the system, the drug may crystallize due to evaporation of volatile solvent, while an excess may result in a lack of bioavailability due to poor release of drug from solvent mixture. The buffer component of the buffered solvent system may be selected from any buffer commonly used in the art; in certain embodiments, water is used. A common ratio of ingredients is about 20% of the nonvolatile solvent, about 40% of the volatile solvent, and about 40% water. There are several optional ingredients which can be added to the topical composition. These include, but are not limited to, chelators and gelling agents. Appropriate gelling agents can include, but are not limited to, semi-synthetic cellulose derivatives (such as hydroxypropylmethylcellulose) and synthetic polymers, galactomannan polymers (such as guar and derivatives thereof) and cosmetic agents.

Lotions include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as stearic or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops or sprays may comprise sterile aqueous or oily solutions or suspensions and may be prepared by dissolving the active ingredient in a suitable aqueous solution of a bactericidal and/or fungicidal agent and/or any other suitable preservative, and, in certain embodiments, including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

For administration by inhalation, salts or polymorphs may be conveniently delivered from an insufflator, nebulizer pressurized packs or other convenient means of delivering an aerosol spray. Pressurized packs may comprise a suitable propellant such as hydrofluoroalkane, dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the formulation may take the form of a dry powder composition, for example a powder mix of the salt or polymorph and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral or intranasal administration may include flavoring agents.

Salts or polymorphs may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more salts or polymorphs which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The salts or polymorphs can be administered in various modes, e.g. orally, topically, or by injection. The precise amount of compound administered to a patient will be the responsibility of the attendant physician. The specific dose level for any particular patient will depend upon a variety of factors including the activity of the specific salt or polymorph employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the salts or polymorphs described herein in combination with another therapeutic agent. By way of example only, if one of the side effects experienced by a patient upon receiving one of the salts or polymorphs herein is inflammation, then it may be appropriate to administer an anti-inflammatory agent in combination with the initial therapeutic agent. Or, by way of example only, the therapeutic effectiveness of one of the salts or polymorphs described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the salts or polymorphs described herein with another therapeutic agent (which also includes a therapeutic regimen) that also has therapeutic benefit. By way of example only, in a treatment for allergic rhinitis involving administration of one of the salts or polymorphs described herein, increased therapeutic benefit may result by also providing the patient with another therapeutic agent for allergic rhinitis. In any case, regardless of the disease, disorder or condition being treated, the overall benefit experienced by the patient may simply be additive of the two therapeutic agents or the patient may experience a synergistic benefit.

Non-limiting examples of possible combination therapies include use of certain compounds disclosed herein with histamine receptor antagonists, including $H_1R$ antagonists, $H_3R$ antagonists, and $H_1R/H_3R$ antagonists; leukotriene inhibitors; alpha-2 agonists; PDE4 inhibitors; intranasal corticosteroids; CRTh2 antagonists; prostaglandin D2 (PGD2) receptor antagonists, including PGD2-1 antagonists; toll-like receptor agonists, including TLR7 agonists and TLR8 agonists; FLAP inhibitors; tissue kallikreins; PI3 kinase inhibitors; secretory phospholipase A2 (sPLA2) inhibitors; glucocorticoid receptor agonists; immunomodulators; leukotriene D4 antagonists; LT/TX dual inhibitors; mast cell inhibitors; tyrosine kinase inhibitor; and inverse agonists of inflammation-related GPCRs.

In certain embodiments, a compound disclosed herein is combined with an $H_1R$ antagonist, an $H_3R$ antagonist, an $H_1R/H_3R$ antagonist, a leukotriene inhibitor, an alpha-2 agonist, a PDE4 inhibitor, or an intranasal corticosteroid. In further embodiments, a compound disclosed herein is combined with an $H_1R$ antagonist, a leukotriene inhibitor, an alpha-2 agonist, a PDE4 inhibitor, or an intranasal corticosteroid. In further embodiments, a compound disclosed herein is combined with an $H_1R$ antagonist or an intranasal corticosteroid. In further embodiments, a compound disclosed herein is combined with an $H_1R$ antagonist. In other embodiments, a compound disclosed herein is combined with an intranasal corticosteroid.

Specific, non-limiting examples of possible combination therapies include use of compounds disclosed herein with:

$H_1R$ antagonists such as acrivastine, alcaftadine, andolast, antazoline, azelastine, bepotastine, bilastine, bromazine, brompheniramine, cetirizine, chlorpheniramine, clemastine, desloratidine, diphenhydramine, diphenylpyraline, ebastine, emedastine, epinastine, fexofenadine, hydroxyzine, ketotifen, levocabastine, levocetirizine, loratidine, methdilazine, mizolastine, promethazine, olopatadine, and triprolidine;

Intranasal corticosteroids such as fluticasone, budesonide, beclomethasone, mometasone, ciclesonide, and triamcinolone;

$H_1R/H_3R$ antagonists such as GSK835726 and GSK1004723;

CRTh2 antagonists such as septipiprant;

Leukotriene inhibitors such as monteleukast (Singulair);

alpha-2 agonists such as oxymetazoline (Afrin);

PDE4 inhibitors such as GSK256066 (6-[[3-[(Dimethylamino)carbonyl]phenyl]sulfonyl]-4-[(3-methoxyphenyl)amino]-8-methyl-3-quinolinecarboxamide);

Monoclonal antibodies such as anti-CCR4 monoclonal antibodies (e.g., mogamulizumab), interleukin-13 (IL-13) monoclonal antibodies, and anti-eotaxin-1 monoclonal antibodies (e.g., bertilimumab);

Inhibitors of PI3K such as wortmannin (irreversible inhibitor), demethoxyviridin, and LY294002 (reversible inhibitor); and Other therapies, such as iodinated contrast agents (e.g. ASP-1001), IG-RD-001 (Leucet, Indigene Pharmaceuticals), and EWO1.

In certain embodiments, compounds disclosed herein are used in combination with an immunomodulator. The immunomodulator may be a liquid mixture of allergen extracts (e.g. Sublivac), a sublingual allergen tablet (e.g., Actair, Oralair, MK-7243 (SCH 697243), MK-3641 (SCH 039641), and MK-8237 (SCH 900237)), or an aluminium hydroxide-adsorbed allergoid preparation of pollen allergens. The immunomodulator may be a mix of allergen extracts or a single agent such as rBet v1 (birch pollen).

In certain embodiments, compounds disclosed herein are used in combination with a preparation of *Lactobacillus acidophilus*, such as En-Lac (encapsulated *Lactobacillus acidophilus* L-92).

The present compounds may also be used in co-therapies, partially or completely, in place of other conventional anti-inflammatory therapies, such as together with steroids, NSAIDs, decongestants, COX-2 selective inhibitors, 5-lipoxygenase inhibitors, LTB₄ antagonists and LTA₄ hydrolase inhibitors. The compounds disclosed herein may also be used to prevent tissue damage when therapeutically combined with antibacterial or antiviral agents.

In certain embodiments, Compound 1 Mesylate Monohydrate Form 1 is used in combination with an orally-administered H1 antagonist chosen from cetirizine (Zyrtec), levocetirizine (Xyzal), loratadine (Claritin), desloratidine (Clarinex), fexofenadine (Allegra), chlorpheniramine, bepotastine (Talion), and bilastine (2-[4-(2-{4-[1-(2-Ethoxyethyl)-1H-benzimidazol-2-yl]-1-piperidinyl}ethyl)phenyl]-2-methylpropanoic acid). Provided herein is a combination therapy comprising Compound 1 Mesylate Monohydrate Form 1 and cetirizine. Also provided herein is a combination therapy comprising Compound 1 Mesylate Monohydrate Form 1 and levocetirizine. Also provided herein is a combination therapy comprising Compound 1 Mesylate Monohydrate Form 1 and loratadine. Also provided herein is a combination therapy comprising Compound 1 Mesylate Monohydrate Form 1 and desloratidine. Also provided herein is a combination therapy comprising Compound 1 Mesylate Monohydrate Form 1 and fexofenadine. Also provided herein is a combination therapy comprising Compound 1 Mesylate Monohydrate Form 1 and chlorpheniramine. Also provided herein is a combination therapy comprising Compound 1 Mesylate Monohydrate Form 1 and bepotastine. Also provided herein is a combination therapy comprising Compound 1 Mesylate Monohydrate Form 1 and bilastine.

In certain embodiments, Compound 2 Hydrochloride Form 1 is used in combination with an orally-administered H1 antagonist chosen from cetirizine (Zyrtec), levocetirizine (Xyzal), loratadine (Claritin), desloratidine (Clarinex), fexofenadine (Allegra), chlorpheniramine, bepotastine (Talion), and bilastine (2-[4-(2-{4-[1-(2-Ethoxyethyl)-1H-benzimidazol-2-yl]-1-piperidinyl}ethyl)phenyl]-2-methylpropanoic acid). Provided herein is a combination therapy comprising Compound 2 Hydrochloride Form 1 and cetirizine. Also provided herein is a combination therapy comprising Compound 2 Hydrochloride Form 1 and levocetirizine. Also provided herein is a combination therapy comprising Compound 2 Hydrochloride Form 1 and loratadine. Also provided herein is a combination therapy comprising Compound 2 Hydrochloride Form 1 and desloratidine. Also provided herein is a combination therapy comprising Compound 2 Hydrochloride Form 1 and fexofenadine. Also provided herein is a combination therapy comprising Compound 2 Hydrochloride Form 1 and chlorpheniramine. Also provided herein is a combination therapy comprising Compound 2 Hydrochloride Form 1 and bepotastine. Also provided herein is a combination therapy comprising Compound 2 Hydrochloride Form 1 and bilastine.

In certain embodiments, Compound 2 Mesylate Form 1 is used in combination with an orally-administered H1 antagonist chosen from cetirizine (Zyrtec), levocetirizine (Xyzal), loratadine (Claritin), desloratidine (Clarinex), fexofenadine (Allegra), chlorpheniramine, bepotastine (Talion), and bilastine (2-[4-(2-{4-[1-(2-Ethoxyethyl)-1H-benzimidazol-2-yl]-1-piperidinyl}ethyl)phenyl]-2-methylpropanoic acid). Provided herein is a combination therapy comprising Compound 2 Mesylate Form 1 and cetirizine. Also provided herein is a combination therapy comprising Compound 2 Mesylate Form 1 and levocetirizine. Also provided herein is a combination therapy comprising Compound 2 Mesylate Form 1 and loratadine. Also provided herein is a combination therapy comprising Compound 2 Mesylate Form 1 and desloratidine. Also provided herein is a combination therapy comprising Compound 2 Mesylate Form 1 and fexofenadine. Also provided herein is a combination therapy comprising Compound 2 Mesylate Form 1 and chlorpheniramine. Also provided herein is a combination therapy comprising Compound 2 Mesylate Form 1 and bepotastine. Also provided herein is a combination therapy comprising Compound 2 Mesylate Form 1 and bilastine.

In certain embodiments, Compound 1 Mesylate Monohydrate Form 1 is used in combination with a nasally-administered H1 antagonist chosen from bepotastine (Bepomax or Beposone), loratadine, olopatadine (Patanase), azelastine (Astelin), and Andolast (CR-2039, 4-(1H-tetrazol-5-yl)-N-(4-[1H-tetrazol-5-yl]phenylbenzamide)). Provided herein is a nasal spray formulation comprising Compound 1 Mesylate Monohydrate Form 1 and bepotastine. Also provided herein is a nasal spray formulation comprising Compound 1 Mesylate Monohydrate Form 1 and loratadine. Also provided herein is a nasal spray formulation comprising Compound 1 Mesylate Monohydrate Form 1 and olopatadine. Also provided herein is a nasal spray formulation comprising Compound 1 Mesylate Monohydrate Form 1 and azelastine. Also provided herein is a nasal spray formulation comprising Compound 1 Mesylate Monohydrate Form 1 and andolast.

In certain embodiments, Compound 2 Hydrochloride Form 1 is used in combination with a nasally-administered H1 antagonist chosen from bepotastine (Bepomax or Beposone), loratadine, olopatadine (Patanase), azelastine (Astelin), and Andolast (CR-2039, 4-(1H-tetrazol-5-yl)-N-(4-[1H-tetrazol-5-yl]phenylbenzamide)). Provided herein is a nasal spray formulation comprising Compound 2 Hydrochloride Form 1 and bepotastine. Also provided herein is a nasal spray formulation comprising Compound 2 Hydrochloride Form 1 and loratadine. Also provided herein is a nasal spray formulation comprising Compound 2 Hydrochloride Form 1 and olopatadine. Also provided herein is a nasal spray formulation comprising Compound 2 Hydrochloride Form 1 and azelastine. Also provided herein is a nasal spray formulation comprising Compound 2 Hydrochloride Form 1 and andolast.

In certain embodiments, Compound 2 Mesylate Form 1 is used in combination with a nasally-administered H1 antagonist chosen from bepotastine (Bepomax or Beposone), loratadine, olopatadine (Patanase), azelastine (Astelin), and Andolast (CR-2039, 4-(1H-tetrazol-5-yl)-N-(4-[1H-tetrazol-5-yl]phenylbenzamide)). Provided herein is a nasal spray formulation comprising Compound 2 Mesylate Form 1 and bepotastine. Also provided herein is a nasal spray formulation comprising Compound 2 Mesylate Form 1 and loratadine. Also provided herein is a nasal spray formulation comprising Compound 2 Mesylate Form 1 and olopatadine. Also provided herein is a nasal spray formulation comprising Compound 2 Mesylate Form 1 and azelastine. Also provided herein is a nasal spray formulation comprising Compound 2 Mesylate Form 1 and andolast.

In certain embodiments, Compound 1 Mesylate Monohydrate Form 1 is used in combination with a nasally-administered corticosteroid chosen from fluticasone proprionate (Flonase), fluticasone furoate (Veramyst, GSK685698), mometasone furoate monohydrate (Nasonex), ciclesonide (Omnaris), budesonide (Rhinocort), triamcinolone acetonide acetonide (Nasacort), and beclomethasone dipropionate dipropionate (Beconase, Clenil). Provided herein is a nasal spray formulation comprising Compound 1 Mesylate Monohydrate Form 1 and fluticasone proprionate. Also provided herein is a nasal spray formulation comprising Compound 1 Mesylate Monohydrate Form 1 and fluticasone furoate. Also provided herein is a nasal spray formulation comprising Compound 1 Mesylate Monohydrate Form 1 and mometasone furoate monohydrate. Also provided herein is a nasal spray formulation comprising Compound 1 Mesylate Monohydrate Form 1 and ciclesonide. Also provided herein is a nasal spray formulation comprising Compound 1 Mesylate Monohydrate Form 1 and budesonide. Also provided herein is a nasal spray formulation comprising Compound 1 Mesylate Monohydrate Form 1 and triamcinolone acetonide. Also provided herein is a nasal spray formulation comprising Compound 1 Mesylate Monohydrate Form 1 and beclomethasone dipropionate.

In certain embodiments, Compound 2 Hydrochloride Form 1 is used in combination with a nasally-administered corticosteroid chosen from fluticasone propriontate (Flonase), fluticasone furoate (Veramyst, GSK685698), mometasone furoate monohydrate (Nasonex), ciclesonide (Omnaris), budesonide (Rhinocort), triamcinolone acetonide (Nasacort), and beclomethasone dipropionate (Beconase, Clenil). Provided herein is a nasal spray formulation comprising Compound 2 Hydrochloride Form 1 and fluticasone propriontate. Also provided herein is a nasal spray formulation comprising Compound 2 Hydrochloride Form 1 and fluticasone furoate. Also provided herein is a nasal spray formulation comprising Compound 2 Hydrochloride Form 1 and mometasone furoate monohydrate. Also provided herein is a nasal spray formulation comprising Compound 2 Hydrochloride Form 1 and ciclesonide. Also provided herein is a nasal spray formulation comprising Compound 2 Hydrochloride Form 1 and budesonide. Also provided herein is a nasal spray formulation comprising Compound 2 Hydrochloride Form 1 and triamcinolone acetonide. Also provided herein is a nasal spray formulation comprising Compound 2 Hydrochloride Form 1 and beclomethasone dipropionate.

In certain embodiments, Compound 2 Mesylate Form 1 is used in combination with a nasally-administered corticosteroid chosen from fluticasone propriontate (Flonase), fluticasone furoate (Veramyst, GSK685698), mometasone furoate monohydrate (Nasonex), ciclesonide (Omnaris), budesonide (Rhinocort), triamcinolone acetonide (Nasacort), and beclomethasone dipropionate (Beconase, Clenil). Provided herein is a nasal spray formulation comprising Compound 2 Mesylate Form 1 and fluticasone propriontate. Also provided herein is a nasal spray formulation comprising Compound 2 Mesylate Form 1 and fluticasone furoate. Also provided herein is a nasal spray formulation comprising Compound 2 Mesylate Form 1 and mometasone furoate monohydrate. Also provided herein is a nasal spray formulation comprising Compound 2 Mesylate Form 1 and ciclesonide. Also provided herein is a nasal spray formulation comprising Compound 2 Mesylate Form 1 and budesonide. Also provided herein is a nasal spray formulation comprising Compound 2 Mesylate Form 1 and triamcinolone acetonide. Also provided herein is a nasal spray formulation comprising Compound 2 Mesylate Form 1 and beclomethasone dipropionate.

In certain embodiments, compounds disclosed herein are used in combination with a leukotriene inhibitor such as monteleukast (Singulair). Provided herein is a combination therapy comprising Compound 1 Mesylate Monohydrate Form 1 and monteleukast. Also provided herein is a combination therapy comprising Compound 2 Hydrochloride Form 1 and monteleukast. Also provided herein is a combination therapy comprising Compound 2 Mesylate Form 1 and monteleukast.

In certain embodiments, Compound 1 Mesylate Monohydrate Form 1 is used in combination with an alpha-2 agonist such as oxymetazoline (Afrin). Provided herein is a combination therapy comprising Compound 1 Mesylate Monohydrate Form 1 and oxymetazoline. Also provided herein is a combination therapy comprising Compound 1 Mesylate Monohydrate Form 1 and oxymetazoline. Also provided herein is a nasal spray formulation comprising Compound 1 Mesylate Monohydrate Form 1 and oxymetazoline. Also provided herein is a nasal spray formulation comprising Compound 2 Hydrochloride Form 1 and oxymetazoline. Also provided herein is a nasal spray formulation comprising Compound 2 Mesylate Form 1 and oxymetazoline.

In certain embodiments, Compound 1 Mesylate Monohydrate Form 1 is used in combination with a PDE4 inhibitor, such as GSK256066 (6-[[3-[(Dimethylamino)carbonyl]phenyl]sulfonyl]-4-[(3-methoxyphenyl)amino]-8-methyl-3-quinolinecarboxamide). Provided herein is a combination therapy comprising Compound 1 Mesylate Monohydrate Form 1 and GSK256066. Provided herein is a combination therapy comprising Compound 1 Mesylate Monohydrate Form 1 and GSK256066. Also provided herein is a nasal spray formulation comprising Compound 2 Hydrochloride Form 1 and GSK256066. Also provided herein is a nasal spray formulation comprising Compound 2 Mesylate Form 1 and GSK256066.

In certain embodiments, Compound 1 Mesylate Monohydrate Form 1 is used in combination with a CRTh2 antagonists such as septipiprant. Provided herein is a combination therapy comprising Compound 1 Mesylate Monohydrate Form 1 and septipiprant. Also provided herein is a nasal spray formulation comprising Compound 2 Hydrochloride Form 1 and septipiprant. Also provided herein is a nasal spray formulation comprising Compound 2 Mesylate Form 1 and septipiprant.

In any case, the multiple therapeutic agents (at least one of which is a salt or polymorph disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating $H_4R$-mediated disorders in a human or animal subject in need of such treatment comprising administering to said subject an amount of a salt or polymorph disclosed herein effective to reduce or prevent said disorder in the subject, optionally in combination with at least one additional agent for the treatment of said disorder that is known in the art.

In a related aspect, certain embodiments provide therapeutic compositions comprising at least one salt or polymorph disclosed herein, optionally in combination with one or more additional agents for the treatment of $H_4R$-mediated disorders. Specific diseases to be treated by the salts, polymorphs, compositions, and methods disclosed herein include inflammation and related diseases, including autoimmune diseases. The salts and polymorphs are useful to treat arthritis, including but not limited to rheumatoid arthritis, spondyloarthropathies, gouty arthritis, osteoarthritis, systemic lupus erythematosus, juvenile arthritis, acute rheumatic arthritis, enteropathic arthritis, neuropathic arthritis, psoriatic arthritis, and pyogenic arthritis. The salts and polymorphs are also useful in treating osteoporosis and other related bone disorders.

These salts and polymorphs can also be used to treat gastrointestinal conditions such as reflux esophagitis, diarrhea, inflammatory bowel disease, Crohn's disease, gastritis, irritable bowel syndrome and ulcerative colitis.

The salts and polymorphs may also be used in the treatment of allergic disorders and disorders related to nasal and upper respiratory inflammation, such as, but not limited to, seasonal allergic rhinitis, non-seasonal allergic rhinitis, acute non-allergic rhinitis, chronic non-allergic rhinitis, Sampter's triad, non-allergic rhinitis with eosinophilia syndrome, nasal inflammation, nasal congestion, sinus congestion, nasal polyposis, atrophic rhinitis, hypertrophic rhinitis, membranous rhinitis, vasomotor rhinitis, rhinosinusitis, chronic rhinopharyngitis, rhinorrhea, occupational rhinitis, hormonal rhinitis, drug-induced rhinitis, gustatory rhinitis, as well as pulmonary inflammation, such as that associated with viral infections and cystic fibrosis. In addition, compounds disclosed herein are also useful in organ transplant patients either alone or in combination with conventional immunomodulators.

Moreover, salts and polymorphs disclosed herein may be used in the treatment of tendonitis, bursitis, skin-related conditions such as psoriasis, allergic dermatitis, atopic dermatitis and other variants of eczema, allergic contact dermatitis, irritant contact dermatitis, seborrhoeic eczema, nummular eczematous dermatitis, autosensitization dermatitis, Lichen Simplex Chronicus, dyshidrotic dermatitis, neurodermatitis, stasis dermatitis, generalized ordinary urticaria, acute allergic urticaria, chronic allergic urticaria, autoimmune urticaria, chronic idiopathic urticaria, drug-induced urticaria, cholinergic urticaria, chronic cold urticaria, dermatographic urticaria, solar urticaria, urticaria pigmentosa, mastocytosis, acute or chronic pruritis, including pruritis associated with skin-localized or systemic diseases and disorders such as pancreatitis, hepatitis, burns, sunburn, and vitiligo.

Further, the salts and polymorphs disclosed herein can be used to treat respiratory diseases, including therapeutic methods of use in medicine for preventing and treating a respiratory disease or condition including: asthmatic conditions including allergen-induced asthma, exercise-induced asthma, pollution-induced asthma, cold-induced asthma, and viral-induced-asthma; chronic obstructive pulmonary disease (COPD) including chronic bronchitis with normal airflow, chronic bronchitis with airway obstruction (chronic obstructive bronchitis), emphysema, asthmatic bronchitis, and bullous disease; and other pulmonary diseases involving inflammation including bronchioectasis cystic fibrosis, pigeon fancier's disease, farmer's lung, acute respiratory distress syndrome, pneumonia, aspiration or inhalation injury, fat embolism in the lung, acidosis inflammation of the lung, acute pulmonary edema, acute mountain sickness, acute pulmonary hypertension, persistent pulmonary hypertension of the newborn, perinatal aspiration syndrome, hyaline membrane disease, acute pulmonary thromboembolism, heparin-protamine reactions, sepsis, status asthamticus and hypoxia.

The salts and polymorphs disclosed herein are also useful in treating tissue damage in such diseases as vascular diseases, periarteritis nodosa, thyroiditis, sclerodoma, rheumatic fever, type I diabetes, neuromuscular junction disease including myasthenia gravis, white matter disease including multiple sclerosis, sarcoidosis, nephritis, nephrotic syndrome, Behcet's syndrome, polymyositis, gingivitis, periodontis, hypersensitivity, and swelling occurring after injury.

The compounds disclosed herein can be used in the treatment of otic diseases and otic allergic disorders, including otic inflammation and eustachian tube itching.

The compounds disclosed herein can be used in the treatment of ophthalmic diseases, such as ophthalmic allergic disorders, including allergic conjunctivitis, vernal conjunctivitis, vernal keratoconjunctivitis, and giant papillary conjunctivitis, dry eye, glaucoma, glaucomatous retinopathy, diabetic retinopathy, retinal ganglion degeneration, ocular ischemia, retinitis, retinopathies, uveitis, ocular photophobia, and of inflammation and pain associated with acute injury to the eye tissue. The salts and polymorphs can also be used to treat post-operative inflammation or pain as from ophthalmic surgery such as cataract surgery and refractive surgery. In certain embodiments, the salts and polymorphs disclosed herein are used to treat an allergic eye disease chosen from allergic conjunctivitis; vernal conjunctivitis; vernal keratoconjunctivitis; and giant papillary conjunctivitis.

Salts and polymorphs disclosed herein are useful in treating patients with inflammatory pain such as reflex sympathetic dystrophy/causalgia (nerve injury), peripheral neuropathy (including diabetic neuropathy), and entrapment neuropathy (carpel tunnel syndrome). The salts and polymorphs are also useful in the treatment of pain associated with acute herpes zoster (shingles), postherpetic neuralgia (PHN), and associated pain syndromes such as ocular pain. Pain indications include, but are not limited to, pain resulting from dermal injuries and pain-related disorders such as tactile allodynia and hyperalgesia. The pain may be somatogenic (either nociceptive or neuropathic), acute and/or chronic.

Besides being useful for human treatment, certain salts and polymorphs and formulations disclosed herein may also be useful for veterinary treatment of companion animals, exotic animals and farm animals, including mammals, rodents, and the like. More preferred animals include horses, dogs, and cats.

All references, patents or applications, U.S. or foreign, cited in the application are hereby incorporated by reference as if written herein in their entireties. Where any inconsistencies arise, material literally disclosed herein controls.

METHODS FOR PREPARING COMPOUNDS AND EXAMPLES

The following schemes can be used to practice the present invention. A person skilled in the art may adapt the schemes to synthesis of compounds other than those they may specifically depict. The invention is further illustrated by the following compound examples, which may be made my methods known in the art and/or as shown below.

SCHEME 1

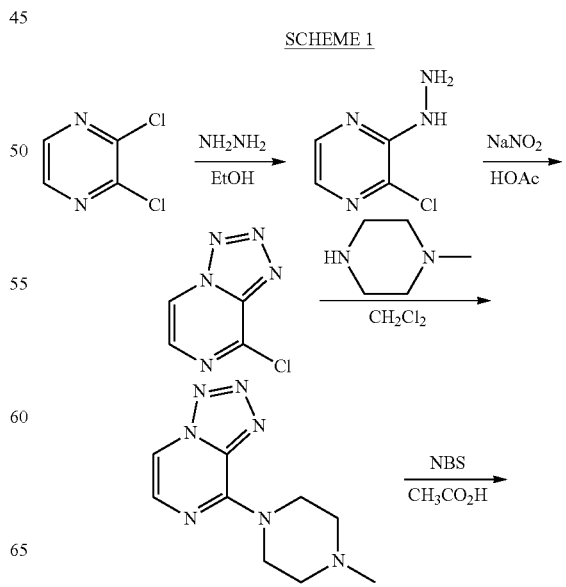

-continued

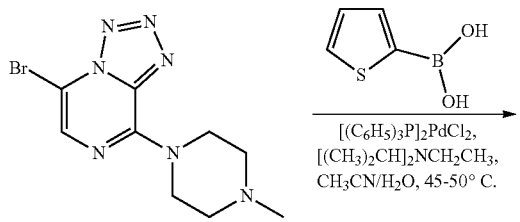 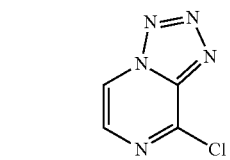

[(C₆H₅)₃P]₂PdCl₂,
[(CH₃)₂CH]₂NCH₂CH₃,
CH₃CN/H₂O, 45-50° C.

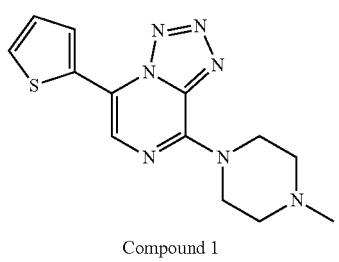

Compound 1

Example 1

8-(4-Methylpiperazin-1-yl)-5-(thiophen-2-yl)tetrazolo[1,5-a]pyrazine

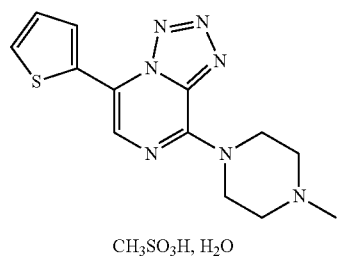

CH₃SO₃H, H₂O

Step 1

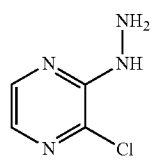

2-Chloro-3-hydrazinylpyrazine 2,3-dichloropyrazine (1000 g, 6.7 mol) and hydrazine monohydrate (700 g, 14 mol) were dissolved in absolute ethanol (2 L) and refluxed under N₂ overnight. A crystalline precipitate formed, which was collected by filtration, washed with ethanol (1 L), and dried to afford the desired produced as a yellow solid (880 g, 90% yield).

Step 2

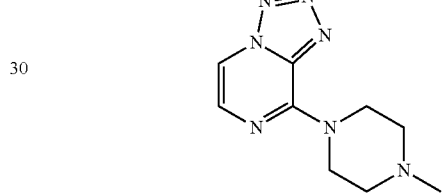

8-Chlorotetrazolo[1,5-a]pyrazine

2-Chloro-3-hydrazinylpyrazine (440 g, 3.0 mol) was suspended in acetic acid (500 mL) and cooled to 10° C. A solution of sodium nitrite (220 g, 3.2 mol) in water (200 mL) at 10° C. was added. The resulting mixture was stirred at 10° C. for 1 h, during which time a crystalline solid precipitated. The precipitate was collected by filtration, washed with ethanol (200 mL) and dried to afford the desired product as a red solid (350 g, 73% yield).

Step 3

8-(4-Methylpiperazin-1-yl)tetrazolo[1,5-a]pyrazine

8-Chlorotetrazolo[1,5-a]pyrazine (100 g, 0.643 mol, 1 eq.) was suspended in methylene chloride (650 ml) and cooled to 3-7° C. under nitrogen. 1-Methylpiperazine (156 g, 1.56 mol, 2.42 eq) was added at such a rate that the temperature of the reaction mixture was maintained at 3-7° C. The mixture is stirred at approximately 10° C. for 15 minutes after which time conversion to product was ≥99%. Celite 545 (40 g) and water (260 g) were added and the pH of the suspension adjusted to 9.5-9.8 by the addition of 27% sodium hydroxide, with the temperature maintained range at 3-7° C. The suspension was filtered on a pad of Celite 545, and the filter cake washed with methylene chloride. The filtrate was separated into an organic and aqueous phase. The aqueous phase was washed with methylene chloride. The organic phases are washed twice with aqueous sodium hydroxide. The organic phases were combined, and dried over magnesium sulfate prior to addition of activated carbon (pH 8-10). The mixture was filtered on a pad of Celite 545 and the filtered cake washed with methylene chloride. The filtrate was concentrated at reduced pressure and crystallization induced by slow addition of heptane, with further concentration and seeding as necessary. The resulting crystal suspension is cooled to 10-15° C., filtered, washed with n-heptane and dried under vacuum at 27-33° C. to afford the product as a buff coloured solid (114.6 g, 81% yield).

Step 4

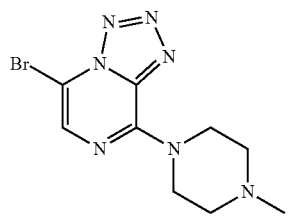 [SMILES: CN1CCN(c2ncc(Br)n3nnnc23)CC1]

5-Bromo-8-(4-methylpiperazin-1-yl)tetrazolo[1,5-a]pyrazine 8-(4-Methylpiperazin-1-yl)tetrazolo[1,5-a]pyrazine (100 g, 0.456 mol, 1.0 eq.) was suspended in acetic acid (110 ml) under nitrogen and stirred at 35° C. until a solution was obtained. The solution was cooled to 16° C. and N-Bromosuccinimide (82.14 g, 0.461 mol, 1.01 eq.) is added at such a rate that the temperature of the reaction was maintained at 14-18° C. The reaction was monitored and additional aliquots of N-bromosuccinimide added as necessary to ensure conversion was ≥99.5% after 2-3 hours stirring at 20° C. stirring. Water was added, and the solution is cooled to 13° C. The pH of the suspension is adjusted to 8.3-8.5 by addition of triethylamine. The resulting suspension was filtered, washed with water, and dried to afford the desired product (136.02 g, 100% yield).

Step 5

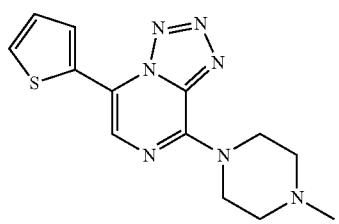 [SMILES: CN1CCN(c2ncc(-c3cccs3)n3nnnc23)CC1]

8-(4-Methylpiperazin-1-yl)-5-(thiophen-2-yl)tetrazolo[1,5-a]pyrazine

5-Bromotetrazolo[1,5-a]pyrazin-8-yl)piperazine (120 g, 0.402 mol, 1.00 eq.) was suspended in acetonitrile (1275 ml) then 2-thiophene boronic acid (72.10 g, 0.564 mol, 1.40 eq.), purified water (110 ml), and N,N-diisopropylethylamine 181.8 g, 1.407 mol, 3.50 eq.) added. The resulting suspension is heated to 35-38° C. to form a clear solution, the pressure was lowered to the point that reflux was established (approx. 250 mbar) and then maintained under refluz at 35-38° C. for an additional 15 minutes. The pressure is released with nitrogen, and the reaction mixture maintained under nitrogen throughout the rest of the procedure. Bis(triphenylphosphine) palladium (II) dichloride (14.1 g, 0.020 mol, 0.05 eq.) was added, and the reaction mixture stirred at 45-50° C. overnight. The product precipitates during the reaction. When conversion achieved a minimum 99.0% (HPLC), the reaction mixture was cooled to 10-12° C. and stirred at 10-12° C. for 2-4 hours. The precipitate was isolated, washed with purified water (10-12° C.), and dried in vacuum at 25-35° C. to afford the title compound as a solid (100.27 g, 83% yield). $^1$H NMR (300 MHz, CDCl$_3$) δ: 8.00 (m, 2H), 7.45 (dd, J=5.1, 1.2 Hz, 1H), 7.20 (dd, J=5.1, 3.6 Hz, 1H), 4.39 (br, 4H), 2.60 (t, J=5.1 Hz, 4H), 2.37 (s, 3H). MS m/z: 302 (M+H$^+$).

SCHEME 2

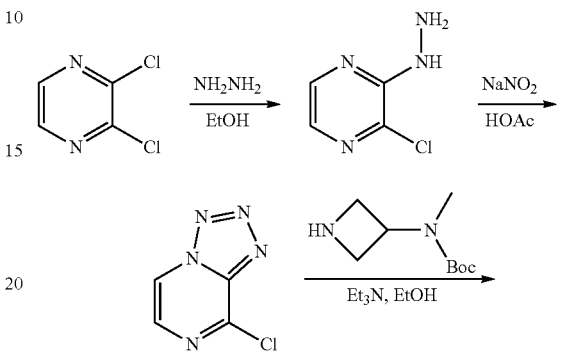

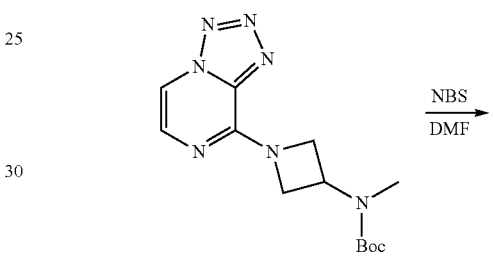

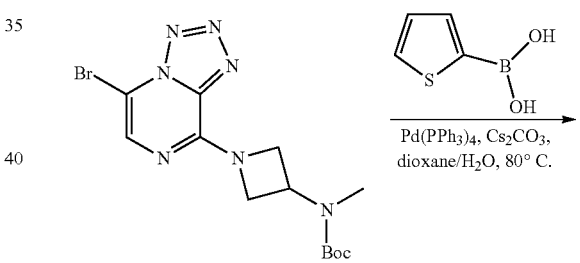

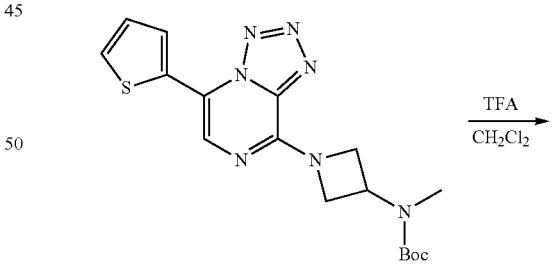

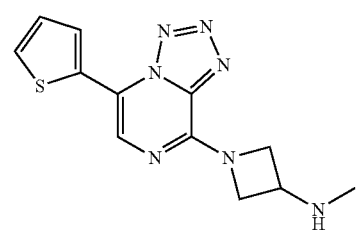 [SMILES: CNC1CN(c2ncc(-c3cccs3)n3nnnc23)C1]

Compound 2

Example 2

N-methyl-1-(5-(thiophen-2-yl)tetrazolo[1,5-a]pyrazin-8-yl)azetidin-3-amine

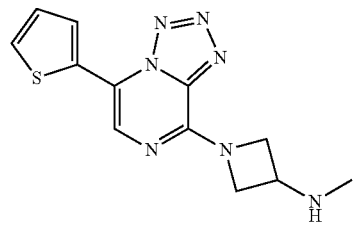

Step 1-2

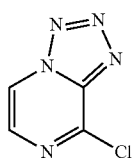

8-Chlorotetrazolo[1,5-a]pyrazine

The title compound was prepared as described in Example 1 steps 1-2.

Step 3

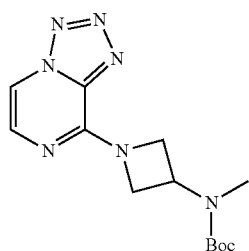 [SMILES: CN(C(=O)OC(C)(C)C)C1CN(c2nccn3nnnc23)C1]

tert-Butyl methyl(1-(tetrazolo[1,5-a]pyrazin-8-yl)azetidin-3-yl)carbamate

A 2 L round bottom flask was charged with 8-chlorotetrazolo[1,5-a]pyrazine (100 g, 0.64 mol), triethylamine (195 g, 1.93 mol) and ethanol (1 L). To the above was added tert-butyl azetidin-3-yl(methyl)carbamate hydrochloride (146 g, 0.66 mol) at 25° C. The resulting mixture was stirred at 25° C. for 1 h. Work-up: the resulting crystalline solid was collected by filtration, washed with ethanol (200 mL), and dried to afford 176 g (91%) of the product as a white solid. MS m/z: 306 (M+H$^+$).

Step 4

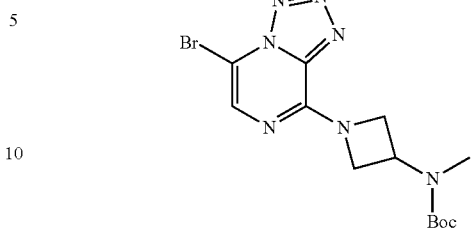

tert-Butyl (1-(5-bromotetrazolo[1,5-a]pyrazin-8-yl)azetidin-3-yl)(methyl)carbamate A 3 L round bottom flask was charged with tert-butyl methyl(1-(tetrazolo[1,5-a]pyrazin-8-yl)azetidin-3-yl)carbamate (200 g, 0.66 mol) and DMF (1 L). To the above was added N-bromosuccinimide (117 g, 0.66 mol) in portions at 10° C. The resulting mixture was stirred at 10° C. for 0.5 h. Work-up: the reaction mixture was poured into water (3 L). The resulting crystalline solid was collected by filtration, washed with water (500 mL), and dried to afford 200 g (79%) of the product as a white solid.

Step 5

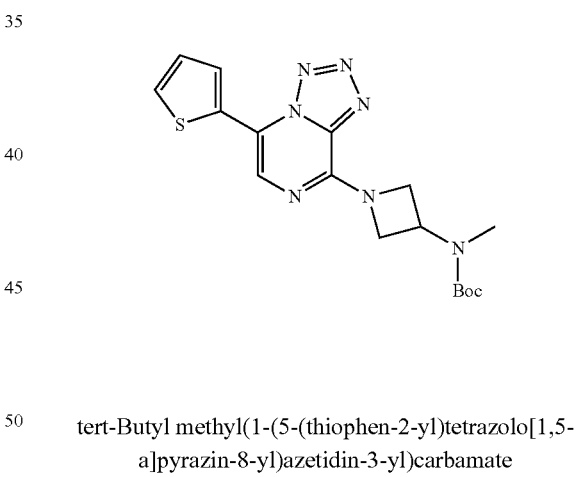

tert-Butyl methyl(1-(5-(thiophen-2-yl)tetrazolo[1,5-a]pyrazin-8-yl)azetidin-3-yl)carbamate A 3 L round bottom flask was charged with tert-butyl (1-(5-bromotetrazolo[1,5-a]pyrazin-8-yl)azetidin-3-yl)(methyl)carbamate (50 g, 0.13 mol), thiophene-2-boronic acid (22 g, 0.17 mol), tetrakis(triphenylphosphine)palladium(0) (5.0 g, 4.3 mmol), Cs$_2$CO$_3$ (50 g, 0.15 mol), 1,4-dioxane (1.5 L) and water (500 mL). After the air was purged by bubbling N$_2$ into the solution, the resulting solution was stirred at 80° C. under N$_2$ for 14 h. Work-up: the reaction mixture was concentrated in vacuo. The residue was purified by flash column chromatography on silica gel with 0-25% ethyl acetate in CH$_2$Cl$_2$, and then crystallized from methanol, to afford 35 g (70%) of the product as a yellow solid.

Step 6

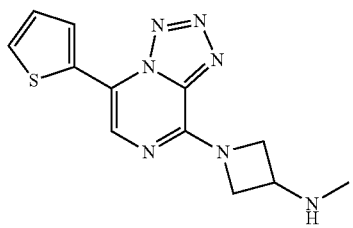 [SMILES: CNC1CN(c2ncc(-c3cccs3)n3nnnc23)C1]

N-methyl-1-(5-(thiophen-2-yl)tetrazolo[1,5-a]pyrazin-8-yl)azetidin-3-amine

A 2 L round bottom flask was charged with tert-butyl methyl(1-(5-(thiophen-2-yl)tetrazolo[1,5-a]pyrazin-8-yl)azetidin-3-yl)carbamate (50 g, 0.13 mol) and dichloromethane (500 mL). To the solution was added trifluoroacetic acid (100 mL). The resulting slurry was stirred at room temperature for 2.5 h. Work-up: the reaction mixture was concentrated in vacuo. The residue was suspended in water (500 L) and treated with solid $Na_2CO_3$ (pH 10~11, there was un-dissolved $Na_2CO_3$ remaining). The solid was collected by filtration, re-suspended in water (500 mL×2) with stirring to remove $Na_2CO_3$. It was further washed with EtOH (500 mL), and dried to afford 27 g (73%) of the product as a yellow solid. $^1$H NMR (400 MHz, DMSO-$d_6$) δ: 8.19 (s, 1H), 7.96 (dd, J=4.0, 0.8 Hz, 1H), 7.76 (dd, J=4.8, 0.8 Hz, 1H), 7.27 (dd, J=4.8, 4.0 Hz, 1H), 4.60 (br, 2H), 4.18 (br, 2H), 3.73 (m, 1H), 2.43 (br, 1H), 2.29 (s, 3H). MS m/z: 288 (M+H$^+$).

Example 3

Salt Formation and Solid State Form Selection

An in-situ salt screen was conducted to identify pharmaceutically acceptable salts with high aqueous solubility, e.g. 10 mg/ml. The in situ salt screen was performed by the method described by Tong & Whitesell (Tong W-Q and Whitesell G *Pharmaceutical Development and Technology*, 1998, 3:215-223. Acid counterions were selected partly on the basis of having pKa two pH units lower that the cognate base and aqueous formulation precedent as an FDA approved nasal spray. Preferred salts demonstrated solubility compatable with delivery as a solution formulation with a target concentration of ≥5 mg/mL at pH ≥4, are crystalline and are easily and reproducibly prepared.

Crystal form screens were performed on preferred salts identified on the basis of in-situ salt screening. The crystal form screen was specifically designed to explore diverse crystallization conditions. Solvents and aqueous mixtures were initially selected based on a diverse range of properties, including dielectric constant, boiling points and H-bonding, which are important to crystallization and crystal-form discovery. The initial list was then modified to include water and aqueous mixtures of high water activity to ensure the discovery of potential hydrates, which are particularly important in the context of a nasal spray solution or suspension in water formulation. The solvent mixture list was then further modified to assess compatibility with API manufacturing process chemistry. Crystallization experiments were conducted in preferred solvents and aqueous mixtures employing known methods such as temperature-cycled ripening of API slurries between 5-40° C. for 48 hours, cooling of saturated solutions prepared at room temperature (15-25° C.) to 4° C. over 24 hours, followed by cooling to −15° C., and slow evaporation of saturated solutions at room temperature. Vapor diffusion experiments were also conducted, typically at room temperature, with solvent systems selected based on API solubility, and the miscibility and boiling points of solvents and antisolvents. Typically a crystal form screen employed 48 solvent systems and in excess of 150 experimental conditions.

Salt and Solid State Form Characterization

Salt and solid state forms were characterized by one or more standard techniques including, but not limited to Differential Scanning calorimetry (DSC), Fourier Transform Infrared (FTIR) spectroscopy, Fourier Transform Raman (FT-Raman) spectroscopy, Gravimetric Vapor Sorption (GVS), High Performance Liquid Chromatography (HPLC), Nuclear Magnetic Resonance (NMR), Polarized Light Microscopy (PLM), Powder X-Ray Diffraction (PXRD), Single Crystal X-Ray Diffraction (SCXRD), ThermoGravimetric Analysis (TGA) and ThermoGravimetric-InfraRed Analysis (TGA-IR).

DSC: DSC was conducted with a TA Instruments Q100 differential scanning calorimeter equipped with an autosampler and a refrigerated cooling system under 40 mL/min $N_2$ purge. DSC thermograms were obtained at 15° C./min in crimped Al pans.

FTIR: IR spectra were collected with a Nicolet 6700 spectrometer (Thermo Electron) equipped with a DTGS detector and a DuraScope. All spectra were acquired at 4 cm$^{-1}$ resolution, 64 scans, using Happ-Cenzel apodization function and 2-level zero-filling.

FT-Raman: Raman spectra were collected with a Nicolet NXR9650 or NXR 960 spectrometer (Thermo Electron) equipped with 1064 nm Nd:YVO4 excitation laser, aliquid-$N_2$ cooled Ge detector, and a MicroStage. All spectra were acquired at 4 cm$^{-1}$ resolution, 64-128 scans, using Happ-Genzel apodization function and 2-level zero-filling.

GVS: GVS experiments were conducted on a SurfaceMeasurement Systems DVS-HT at 25° C. The instrument was operated in step mode and the relative humidity (RH) was increased in 10% RH increments from 40% RH to 90% RH, then decreased from 90% RH to 0% RH, then increased a second time from 0% RH to 90% RH, then decreased from 90% RH to 0% RH. An extra step at 75% RH was included in each cycle. The mass equilibrium criterion was set at 0.005% change in mass over time (dm/dt). A minimum step time of 10 minutes and a maximum step time of 240 minutes were specified.

HPLC: HPLC was performed using a HP1100 HPLC system equipped with a G1131 Quad pump, G1367A autosampler, and G1315B diode array detector. The Column comprised Phenomenex Luna CN 100A (50×4.6 mm, 3 µm) at 40° C. and a mobile phase of A) 0.05% TFA in water and B) 0.05% TFA in acetonitrile. The gradient was 0% B to 95% B over 8 min (2 min re-equilibration), the flow rate: 1 mL/min, and the injection volume 1 µL. Detection was done at 214 and 345 nm.

NMR: NMR spectra were acquired using a Varian Unity Inova 500 MHz instrument, equipped with VNMR 6.1C software at 25° C., unless otherwise noted. Chemical shifts are reported in ppm relative to a TMS reference. Coupling constants are reported in Hz.

PLM: Residual solid filtrants isolated from salt screening experiments and salt candidates were assessed by PLM, with observations being recorded as "Crystalline" or "Not Crystalline". On occasion, the appearance of solid state forms was captured photographically.

PXRD: PXRD diffractograms were acquired using a PANalytical X'Pert Pro diffractometer on Si zero-background wafers. Diffractograms were collected using a monochromatic Cu Kα (45 kV/40 mA) radiation and a step size of 0.02° 2 θ unless noted otherwise.

SCXRD: X-ray measurements were made on a Bruker-Nonius Kappa Axis X8 Apex2 diffractometer at a temperature of 110K. Crystal were mounted on a Mitegen polyimide micromount with a small amount of Paratone N oil. Structure was solved by direct methods using the XS program (Bruker-AXS, XS version 2009.9). Structure refinement was effected using the XL program from SHELXTL. Graphic plots were produced using the NRCVAX crystallographic program suite.

TGA: TGA thermograms were obtained with a TA Instruments Q500 thermogravimetric analyzer under 40 mL/min $N_2$ purge at 15° C./min in Pt or Al pans.

TGA-IR: TGA-IS was conducted with a TA Instruments Q5000 thermogravimetric analyzer interfaced to a Nicolet 6700 FT-IR spectrometer (Thermo Electron) equipped with an external TGA-IR module with a gas flow cell and DTGS detector. TGA was conducted with 60 mL/min $N_2$ flow and heating rate of 15° C./min in Pt or Al pans. IR spectra were collected at 4 $cm^{-1}$ resolution and 32 scans at each time point.

Compound 1

Salt Formation and Solid State Forms

In situ salt formation screening was performed by the method of Tong & Whitesell (Tong W-Q and Whitesell G *Pharmaceutical Development and Technology*, 1998, 3:215-223. Compound 1 was combined with 0.1M aqueous solutions of twelve acids at ambient temperature, reaction mixtures monitored, recharged with Compound 1 where appropriate and slurries temperature cycled between 5-40° C. for 48 hours. Reaction mixtures were then filtered and filtrant residual solids and filtrates analyzed as shown in Table 1.

TABLE 1

Results of In-Situ Salt Formation Screen for Compound 1

| Compound 1 (mg) | Counterion | Filtrant PLM | Filtrant FTIR | Filtrate pH | Filtrate Solubility (mg/mL) |
|---|---|---|---|---|---|
| 25 | Acetic Acid | Crystalline | Free Base | 4.02 | 7.99 |
| 25 | Citric Acid | Crystalline | Salt | 3.11 | 1.75 |
| 25 | Sulfuric Acid | Crystalline | Salt | 1.39 | 0.56 |
| 25 | Phosphoric Acid | Crystalline | Salt | 1.76 | 0.87 |
| 25 | Hydrochloric Acid | Crystalline | Salt | 1.25 | 0.99 |
| 25 | L-Aspartic Acid | Crystalline | Free Base | 4.20 | 8.64 |
| 25 | L-Glutamic Acid | Crystalline | Free Base | 4.28 | 6.75 |
| 40 | L-Malic Acid | Crystalline | Salt | 4.15 | 13.4 |
| 25 | L-Tartaric Acid | Crystalline | Salt | 3.48 | 8.69 |
| 25 | Mesic Acid | No Solids Isolated | | 1.49 | 20.0 |
| 40 | Stearic Acid | Crystalline | Free Base | 8.00 | ND |
| 25 | Succinic Acid | Crystalline | Free Base | 4.13 | 10.4 |

ND: Note Detectable

The results indicate that Compound 1 citrate, sulfate, phosphate and hydrochloride salts have solubility of <5 mg/mL, whereas Compound 1 malate and tartrate salts have solubility of >5 mg/mL under these conditions.

In certain embodiments, initially promising compounds are those which formed crystalline salts having high solubility in or near the range of pH 4-5.

On the basis of the data presented in Table 1, Compound 1 Tartrate and Compound 1 Mesylate were selected for more detailed assessment.

Compound 1 Tartrate Salt

Crystallization experiments targeting the preparation of Compound 1 tartrate salt were conducted in which the effect of solvent (acetone, acetonitrile, tetrahydrofuran, methanol, isopropyl alcohol, water/1% DMSO, ethyl acetate, dichloroethane, MTBE, Toluene, MIBK and dioxane) was surveyed.

A single hemihydrate form designated Compound 1 Tartrate Form 1 was produced in nine of twelve crystallization experiments performed. A stable monohydrate form, designated Compound 1 Tartrate Form 2 was encountered during scale-up experiments. A competitive ripening experiment conducted between Compound 1 Tartrate salt Form 1 and Compound 1 Tartrate salt, Form 2 demonstrated that Compound 1 Tartrate Form 2 is more stable than Compound 1 Tartrate Form 1 in water at 23° C.

Evidence for possible additional forms and/or salts of different stoichiometry was discovered. Thus equilibrium solubility experiments of Compound 1 Tartrate in acetate buffer (pH5) resulted in a new solid state which NMR analysis revealed to possess Compound 1: Tartrate stoichiometry of 1:0.8. An attempt to scale up of the in situ Compound 1 Tartrate form failed, but ultimately yielded a pure sample of Compound 1 Tartrate Form 2.

Preparation of Compound 1 Tartrate Salt, Form 1

Compound 1 (101.5 mg) was added to 3.0 mL of methanol (30 vol). The slurry was stirred and heated to 60° C. L-tartaric acid (3M in water, 1.0 eq.) was added to the slurry at 60° C. The solids dissolved quickly. This solution was mixed for 15 minutes at 60° C. during which time crystallization occurred to produce a thick slurry. The slurry was mixed and temperature-cycled from 40 to 5° C. over 18 hours then equilibrated to 23° C. Crystalline solids were isolated by vacuum filtration to yield the tartrate salt (144 mg, 93%).

Compound 1 Tartrate Salt Form 1 was characterized as follows:

i) $^1$H NMR: (500 MHz, DMSO-$d_6$) δ: 8.27 (s, 1H), 7.99 (d, J=3.5 Hz, 1H), 7.79 (d, J=5 Hz, 1H), 7.28 (m, 1H), 4.27, 4.20 (s,s, 5.6H*), 2.58 (m, 6.7H), 2.504 (s, H), 2.29 (s, 2.85H) *** (where * indicates singlet coincident with water;  indicates aliphatic coincident with DMSO; * indicates unable to determine tartrate salt stoichiometry due to overlapping signals.)

ii) PXRD: The PXRD diffractogram of Compound 1, Tartrate Salt, Form 1 is depicted in FIG. 1; the associated PXRD Peaks are listed in Table 2 (where * indicates ±0.2° and ** indicates that the relative intensity for each peak is determined by normalizing its intensity to that of the strongest peak at 18.1° angle as 100).

TABLE 2

PXRD Peaks of Compound 1, Tartrate Salt, Form 1
PXRD Peaks of
Compound 1 Tartrate Form 1 (Hemihydrate)

| Two-Theta Angle* (degree) | Relative Intensity** (arbitrary) |
|---|---|
| 5.1 | 15.1 |
| 10.2 | 99.1 |
| 13.4 | 76.2 |
| 14.1 | 22.0 |
| 16.6 | 29.2 |
| 17.4 | 88.9 |
| 18.1 | 100.0 |
| 19.1 | 93.1 |
| 22.1 | 27.6 |
| 22.9 | 45.4 |
| 23.5 | 88.8 |
| 24.4 | 33.6 |
| 25.3 | 35.5 |
| 26.0 | 88.3 |
| 27.0 | 54.0 |
| 29.8 | 48.2 |
| 30.7 | 19.9 |
| 36.7 | 12.6 |
| 38.2 | 23.0 | iii) FT-Raman: The FT-Raman Spectrum of Compound 1, Tartrate Salt, Form 1 is depicted in FIG. 2; the associated FT-Raman Peaks are listed in Table 3.

TABLE 3

FT-Raman Peaks of Compound 1, Tartrate Salt, Form 1
FT-Raman Peaks of
Compound 1 Tartrate Form 1 (Hemihydrate)

Figure 3:
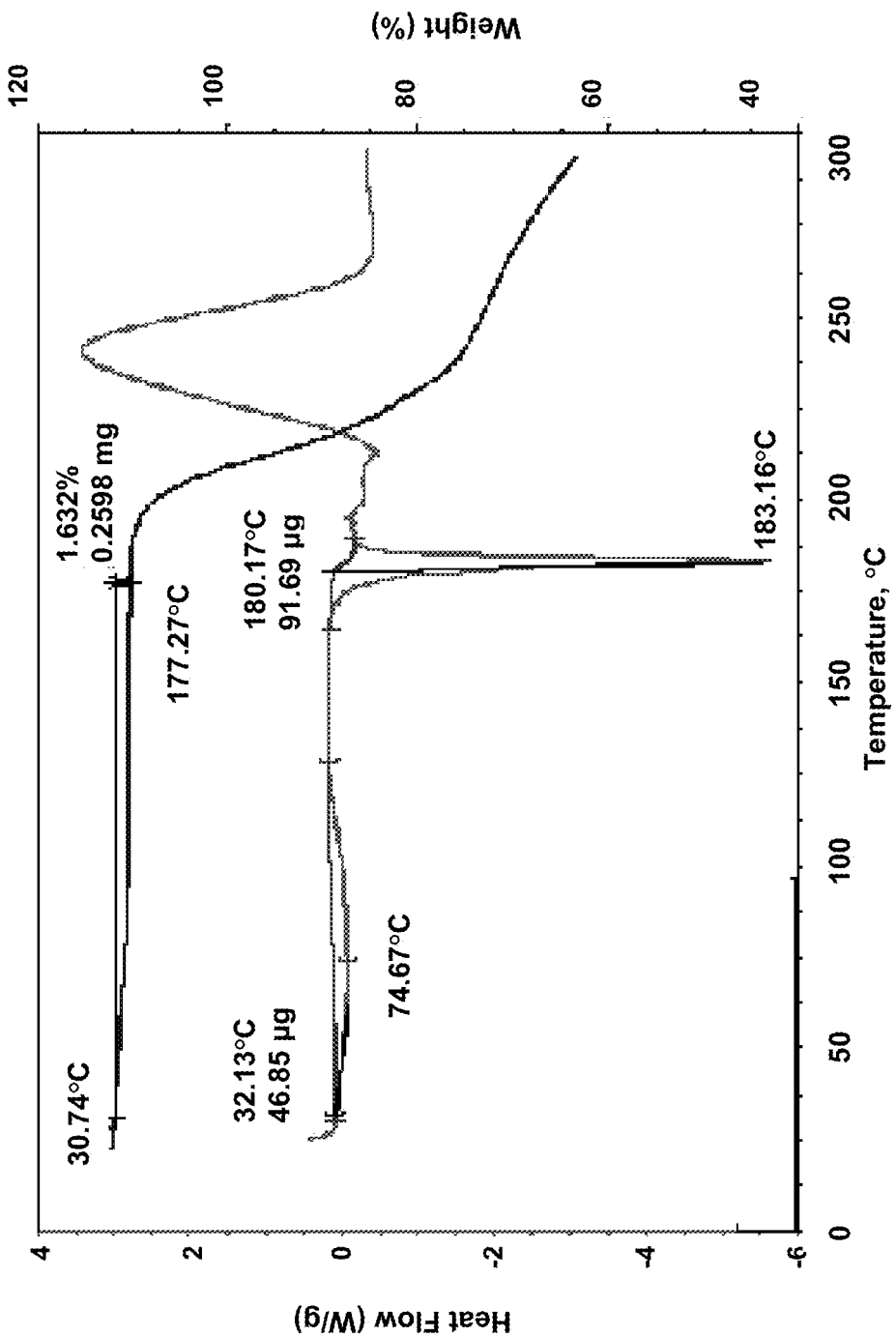
FIG. 3: DSC/TGA Analysis of 8-(4-Methylpiperazin-1-yl)-5-(thiophen-2-yl)tetrazolo[1,5-a]pyrazine Tartrate Hemihydrate Form 1, also known as Compound 1, Tartrate Salt, Form 1.
Figure 4:
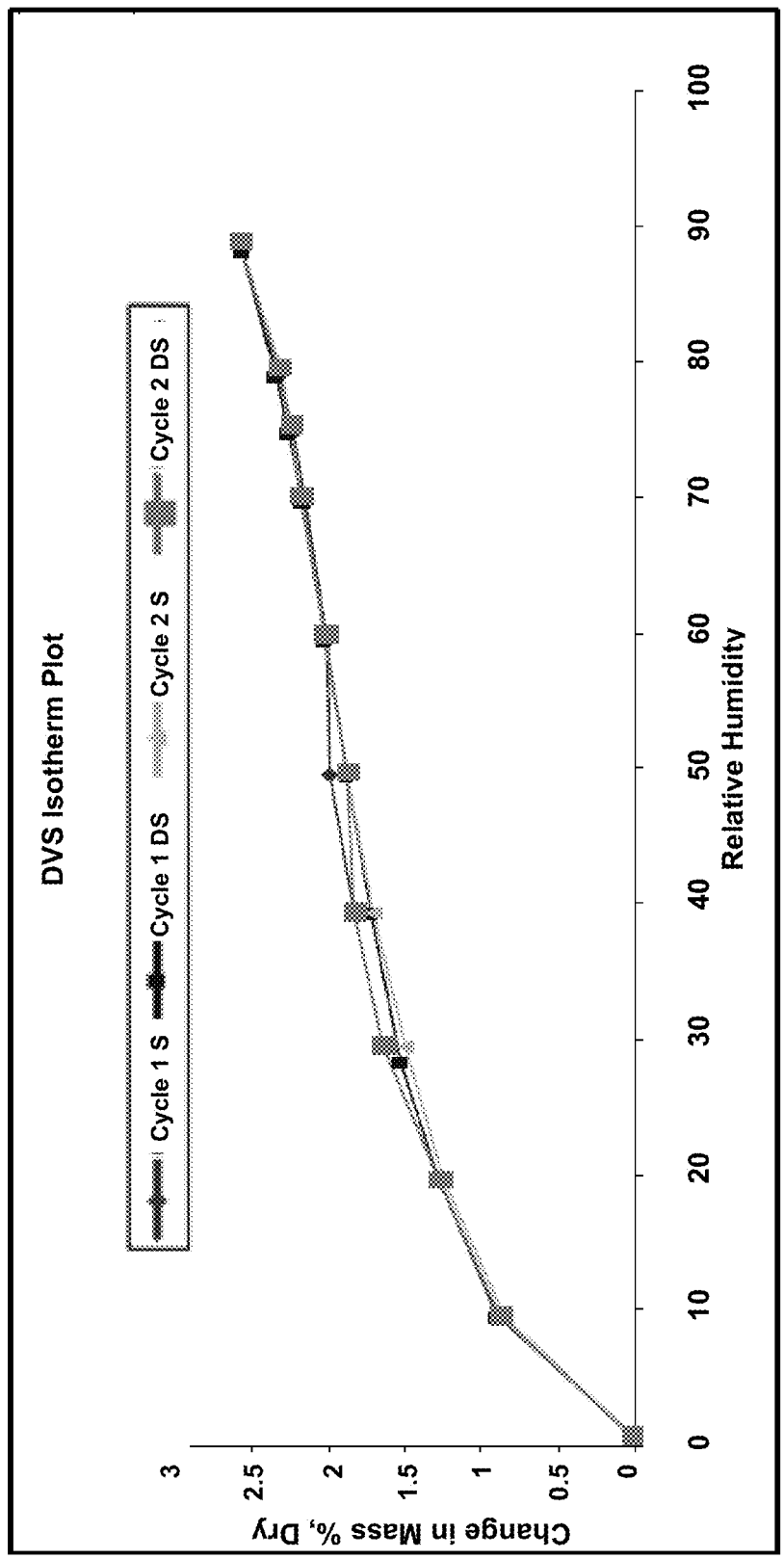

| Position (cm$^{-1}$) | Intensity |
|---|---|
| 624.3 | 31.4 |
| 649.8 | 15.3 |
| 1089.3 | 15.7 |
| 1229.0 | 31.8 |
| 1295.4 | 30.2 |
| 1339.3 | 119.9 |
| 1356.4 | 219.9 |
| 1419.7 | 84.2 |
| 1497.3 | 85.8 |
| 1524.4 | 177.6 |
| 1551.2 | 42.5 |
| 1589.4 | 105.0 | iv) DSC/TGA: The DSC/TGA scans Compound 1, Tartrate Salt, Form 1 is depicted in FIG. 3. The results of DSC abd TGA-IR suggest that Compound 1 Tartrate Form 1 is a hemihydrate (1.6% water).

v) GVS: The GVS isotherm plot for Compound 1, Tartrate Salt Form 1 is depicted in FIG. 4. The GVS curve indicates a weight change of 1.5% below 30% Relative Humidity (RH) and 1% between 30-90% RH. These results are consistent with the thermal analysis and Compound 1 Tartrate Form 1 being a hemihydrate.

Preparation of Compound 1 Tartrate Salt, Form 2

Compound 1 (49.8 mg) was added to 0.5 mL of methanol/water (1:1) (10 vol). The slurry was stirred and heated to 60° C. L-Tartaric acid (3M in water, 1.0 equiv.) was added to the slurry at 60° C. Most solids dissolved quickly, but a few large particles required 10 min to completely dissolve. The solution was seeded with ~2 mg of Compound 1 Tartrate Form 2 crystals at 60° C. and stirred for 105 minutes to produce a thick slurry. The slurry was cooled from 60° C. to 5° C. over 2 hours then stirred at 5° C. for 12 hours. Crystalline solids were isolated by vacuum filtration to yield 69.6 mg of Compound 1 Tartrate Form 2.

Compound 1 Tartrate Salt Form 2 was characterized as follows:

$^1$H NMR: (500 MHz, DMSO-d$_6$) δ: 8.28 (s, 1H), 8.00 (d, J=3.0 Hz, 1H), 7.80 (d, J=5 Hz, 1H), 7.29, 7.28 (ABq, J$_{AB}$=4 Hz, 1H), 4.29 (s, H2O), 4.25 (s, 2H*), 2.64 (m, 7.5H), 2.33 (s, 3H)* (where indicates * used for stoichiometric determination of tartrate,  indicates used for stoichiometric determination of Compound 1, and * indicates the $^1$H NMR spectrum confirms that the ratio of Compound 1:Tartrate is 1:1).

ii) PXRD: The PXRD diffractogram of Compound 1, Tartrate Salt, Form 2 is depicted in FIG. 5; the associated PXRD Peaks are listed in Table 4.

TABLE 4

PXRD Peaks of Compound 1, Tartrate Salt, Form 2
PXRD Peaks of Compound 1 Tartrate Form 2 (Monohydrate)

| Two-Theta Angle* (degree) | Relative Intensity** (arbitrary) |
|---|---|
| 5.7 | 8.3 |
| 11.4 | 22.0 |
| 12.7 | 2.3 |
| 14.5 | 2.4 |
| 15.3 | 5.2 |
| 15.7 | 6.6 |
| 16.2 | 14.3 |
| 17.1 | 100.0 |
| 19.0 | 10.5 |
| 19.3 | 3.5 |
| 23.8 | 11.8 |
| 24.1 | 35.7 |
| 26.2 | 6.9 |
| 27.2 | 6.1 |
| 27.6 | 7.1 |
| 28.1 | 4.5 |
| 29.2 | 6.6 |
| 31.7 | 4.8 |
| 34.7 | 3.4 |
| 35.1 | 3.3 |

*±0.2°
**The relative intensity for each peak is determined by normalizing its intensity to that of the strongest peak at 17.1° angle as 100 iii) FT-Raman: The FT-Raman Spectrum of Compound 1, Tartrate Salt, Form 2 is depicted in FIG. 6; the associated FT-Raman Peaks are listed in Table 5.

TABLE 5

FT-Raman Peaks of Compound 1, Tartrate Salt, Form 2
FT-Raman Peaks of Compound 1 Tartrate Form 2 (Monohydrate)

Figure 7:
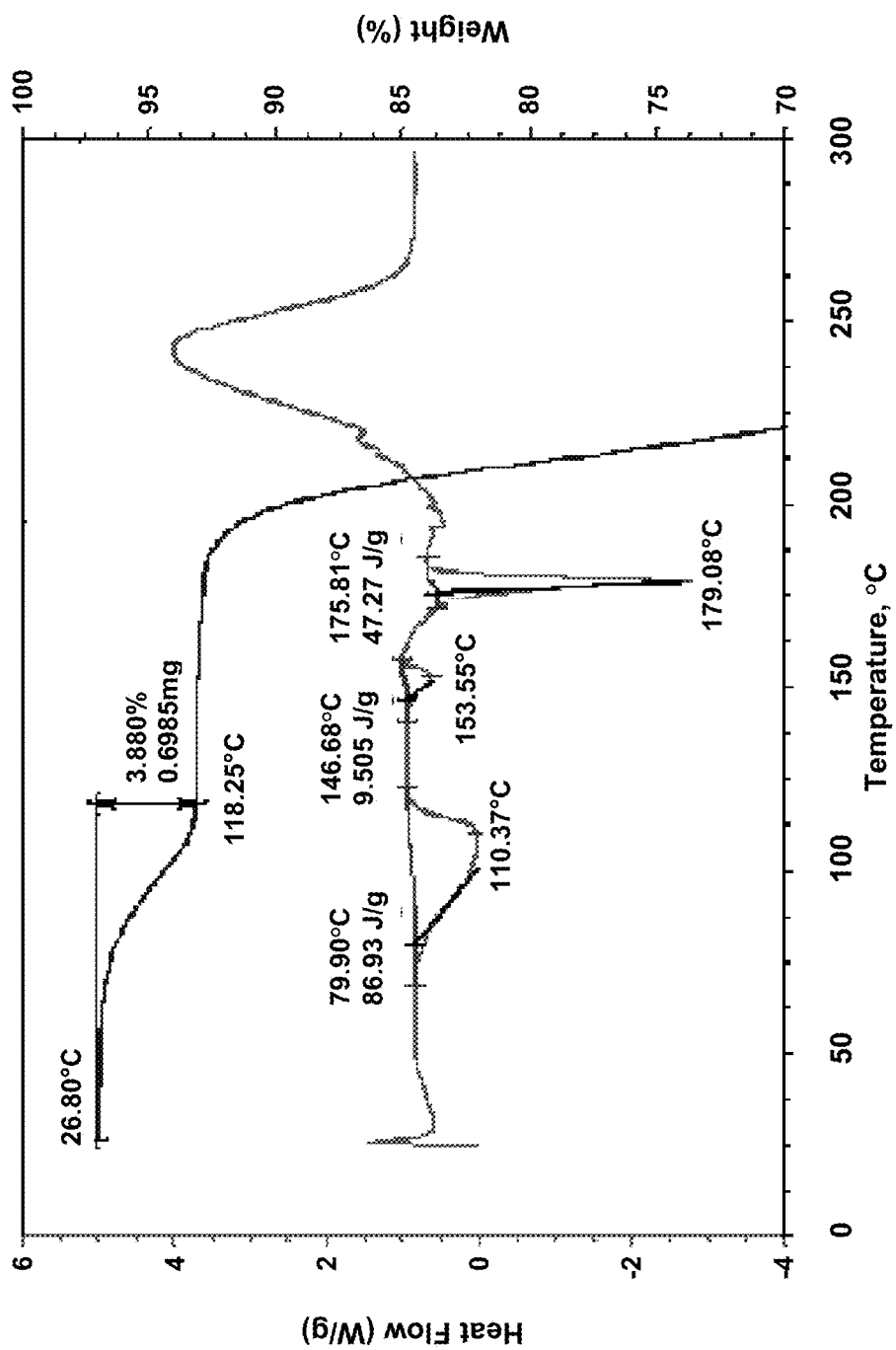
FIG. 7: DSC/TGA Analysis of 8-(4-Methylpiperazin-1-yl)-5-(thiophen-2-yl)tetrazolo[1,5-a]pyrazine Tartrate Monohydrate Form 2, also known as Compound 1, Tartrate Salt, Form 2.
Figure 8:
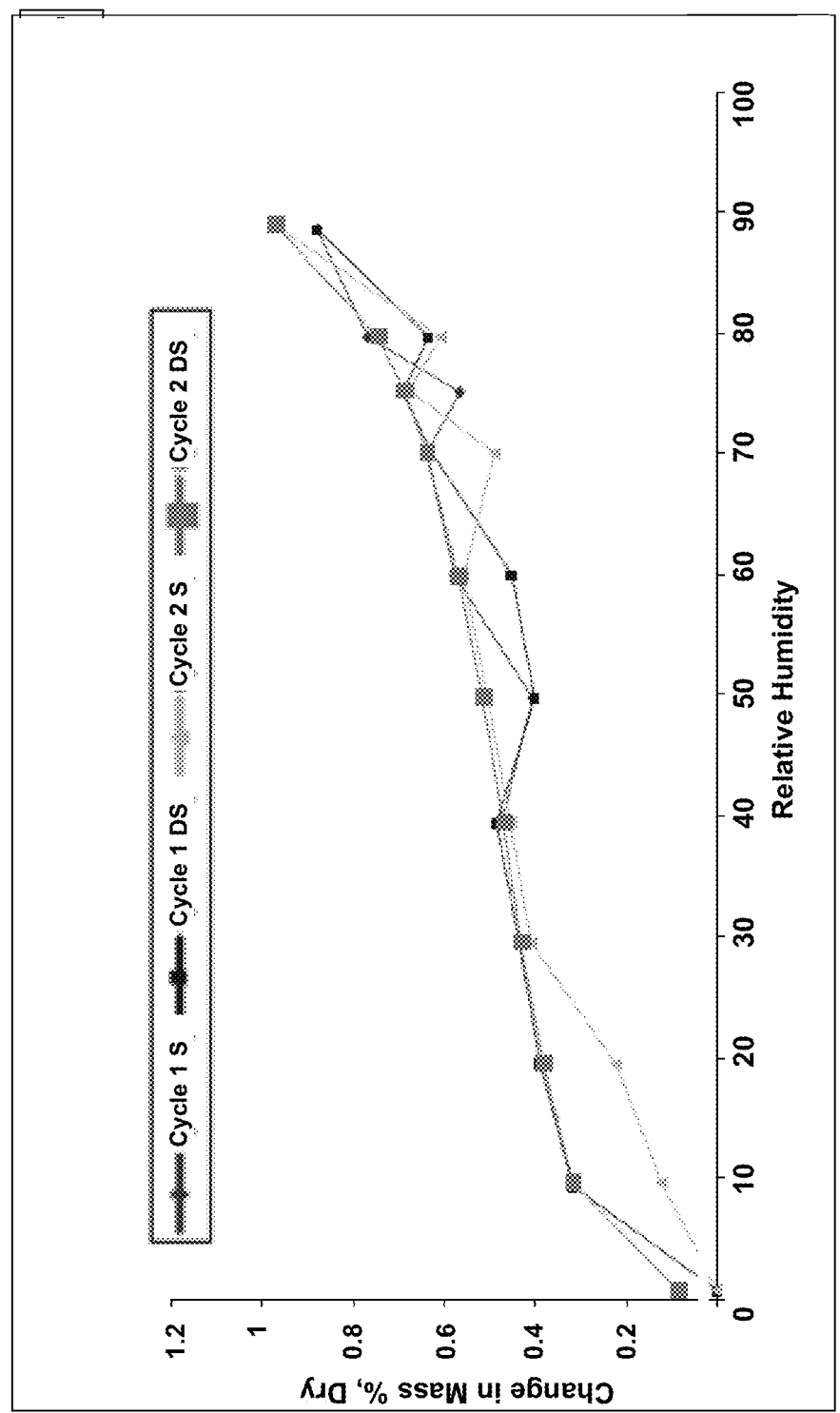
FIG. 8: GVS Isotherm Plot of 8-(4-Methylpiperazin-1-yl)-5-(thiophen-2-yl)tetrazolo[1,5-a]pyrazine Tartrate Monohydrate Form 2, also known as Compound 1, Tartrate Salt, Form 2.

| Position (cm$^{-1}$) | Intensity |
|---|---|
| 622.3 | 26.2 |
| 644.8 | 41.9 |
| 748.1 | 22.1 |
| 1229.3 | 30.1 |
| 1295.0 | 47.0 |
| 1350.4 | 331.8 |
| 1376.5 | 48.5 |
| 1421.8 | 123.9 |
| 1432.2 | 97.3 |
| 1494.4 | 167.5 |
| 1522.1 | 237.2 |
| 1592.6 | 152.6 | iv) DSC/TGA: The DSC/TGA scans of Compound 1, Tartrate Salt, Form 2 are depicted in FIG. 7. Compound 1, Tartrate Salt, Form 2 is a stable monohydrate. The dehydration event occurs between 80 and 130° C., with loss of 3.9% water.

v) GVS: The GVS isotherm plot for Compound 1, Tartrate Salt, Form 2 is depicted in FIG. 8. Compound 1, Tartrate Salt, Form 2 exhibits a ~1% weight change between 5% and 90% RH. FT-Raman analysis before and after GVS showed no Form change. The data are consistent with the thermal analysis and indicate that Compound 1, Tartrate Salt Form 2 is a stable, non-hydroscopic monohydrate.

Compound 1 Mesylate Salt

Crystallization experiments targeting the preparation of Compound 1 Mesylate Salt were conducted in which the effect of solvent (acetone, acetonitrile, tetrahydrofuran, methanol, isopropyl alcohol, water/1% DMSO, ethyl acetate, dichloroethane, MTBE, Toluene, MIBK and dioxane) and crystallization methods (temperature cycling, evaporation) were surveyed.

Two crystal forms of Compound 1 Mesylate Salt were obtained from these experiments. Compound 1 Mesylate Salt, Form 1 is a monomesylate reversible monohydrate solid state form that was obtained from ten of the twelve crystallization experiments conducted. Compound 1 Mesylate Salt Form 1 exhibits good physical properties and high aqueous solubility (>100 mg/ml). Compound 1 Mesylate Salt Form 2 was obtained by slow evaporation of gummy solids at ambient temperature in two of twelve screening experiments. Compound 1 Mesylate Salt Form 2 was obtained as a mixture of Form 1 and Form 2 in one of twelve crystallization experiments. Compound 1 Mesylate Salt Form 2 was subsequently isolated in pure form from a scale up experiment and was demonstrated to undergo significant conversion to Compound 1 Mesylate Salt Form 1 after three days in a closed vial at room temperature.

A Compound 1 Mesylate salt form screen was conducted involving about 160 crystallization experiments in 48 solvents and aqueous mixtures was performed conducted as previously described (vide supra). Compound 1 Mesylate Salt Form 1, the reversible monohydrate initially discovered in during the crystallization experiments cited above, was obtained from a variety of solvents and crystallization conditions, including 25 slurry-ripening, six cooling, 16 evaporative and four vapor diffusion experiments. Form 1 was determined to be the most, and the only, stable crystal form of the five discovered mesylate salts under ambient conditions as tested. Samples of Compound 1, Mesylate Salt Forms 2-5 converted to Compound 1 Mesylate Salt Form 1 in solid state within one week at ambient conditions.

Compound 1, Mesylate Salt Form 2, described above was not encountered in the Compound 1 Mesylate Salt form screen.

Compound 1 Mesylate Salt Form 3 is a non-solvated form that was obtained from 17 slurry ripening, one cooling and one evaporative crystallization experiments. FT-Raman analysis of 8 Compound 1 Mesylate Salt Form 3 screening samples showed complete conversion to Compound 1 Mesylate Salt Form 1 in four days on a well plate at ambient conditions.

Compound 1 Mesylate Salt Form 4 is a non-stoichiometric hydrate that was obtained from one slurry ripening (nitromethane), four cooling and one vapor diffusion experiments. The Compound 1 Mesylate Form 4 exhibits a broad dehydration event below 110° C. with loss of 0.9% water and converted to Compound 1 Mesylate Salt Form 1 in four days on a well plate at ambient conditions.

Compound 1 Mesylate Salt Form 5 is an ethanol solvate (DSC/TGA-IR: 4.1%, 0.4 eq. ethanol) that was obtained from cooling crystallization of an ethanol solution and as a mixture with Compound 1 Mesylate Salt Form 1 from evaporation of an ethanol solution. Compound 1 Mesylate Salt Form 5 converted to Compound 1 Mesylate Salt Form 1 in six days in a closed vial at ambient temperature.

Preparation Compound 1 Mesylate Salt, Form 1

Compound 1 (2.315 g, 7.68 mmol) was added to 11.58 mL of acetronitrile/5% water (5 vol). The slurry was stirred and heated to 60° C. Mesic acid (>99.5%, 0.523 mL, 1.05 eq.) was diluted in 1.16 mL of acetonitrile/5% water (0.5 vol) and added to the slurry at 60° C. This solution was seeded at 60° C. and stirred for 60 min to produce a thick slurry. The slurry was cooled from 60 to 5° C. over 2 hours and stirred at 5° C. for 2 hrs. Crystalline solids were isolated by vacuum filtration, rinsed and washed with ~2.3 mL (1 vol) of acetronitrile/5% water to yield a 2.585-g wet cake. It was dried at ambient temperature under vacuum for 16 hours then exposed to ambient conditions for 3 hours to afford Compound 1 Mesylate Salt Form 1 (2.55 g, 80%).

Compound 1 Mesylate Salt Form 1 was characterized as follows:

i) $^1$H NMR: (500 MHz, DMSO-$d_6$) δ: 10.11 (br s, 1H), 8.36 (s, 1H), 8.05 (d, J=3.0 Hz, 1H), 7.85 (d, J=5 Hz, 1H), 7.31 (at, J=3.5 Hz, 1H), 5.32 (br s, 2H), 3.66 (br s, 2H), 3.36 (br s, 2H), 3.27 (br s, 2H), 2.88 (s, 3H).

ii) PXRD: The PXRD diffractogram of Compound 1, Mesylate Salt, Form 1 is depicted in FIG. 9; the associated PXRD Peaks are listed in Table 6 (where * indicates ±0.2° and ** indicates the relative intensity for each peak is determined by normalizing its intensity to that of the strongest peak at 21.2° angle as 100).

TABLE 6

PXRD Peaks of Compound 1, Mesylate Salt, Form 1
PXRD Peaks of Compound 1 Mesylate Form 1 (Monohydrate)

| Two-Theta Angle* (degree) | Relative Intensity** (arbitrary) |
|---|---|
| 5.3 | 25.4 |
| 10.5 | 13.8 |
| 13.5 | 5.0 |
| 15.1 | 11.8 |
| 15.9 | 2.5 |
| 18.0 | 4.8 |
| 18.3 | 3.7 |
| 19.8 | 3.1 |
| 20.4 | 11.5 |
| 21.2 | 100.0 |
| 21.8 | 11.7 |
| 22.5 | 2.3 |
| 23.0 | 18.0 |
| 23.3 | 7.1 |
| 25.3 | 8.1 |
| 26.5 | 2.9 |
| 27.1 | 3.3 |
| 28.0 | 7.6 |
| 28.5 | 3.4 |
| 30.6 | 2.1 |
| 33.0 | 6.0 |
| 35.3 | 2.6 |
| 37.5 | 4.1 | iii) FT-Raman: The FT-Raman Spectrum of Compound 1, Mesylate Salt, Form 1 is depicted in FIG. 10; the associated FT-Raman Peaks are listed in Table 7.

TABLE 7

FT-Raman Peaks of Compound 1, Mesylate Salt, Form 1
FT-Raman Peaks of
Compound 1 Mesylate Form 1 (Monohydrate)

Figure 11:
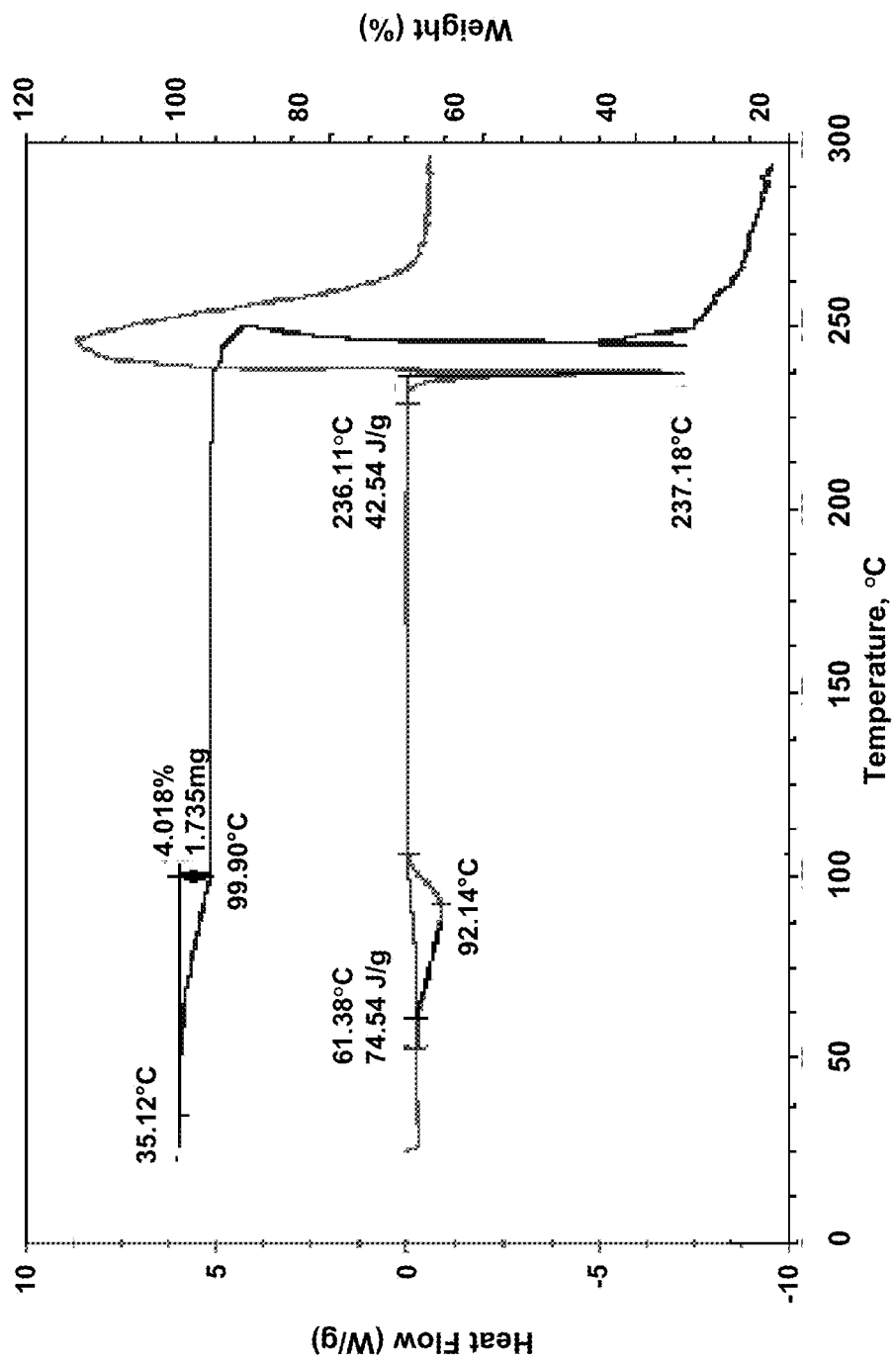
FIG. 11: DSC/TGA Analysis of 8-(4-Methylpiperazin-1-yl)-5-(thiophen-2-yl)tetrazolo[1,5-a]pyrazine Mesylate Monohydrate Form 1, also known as Compound 1, Mesylate Salt, Form 1.
Figure 12:
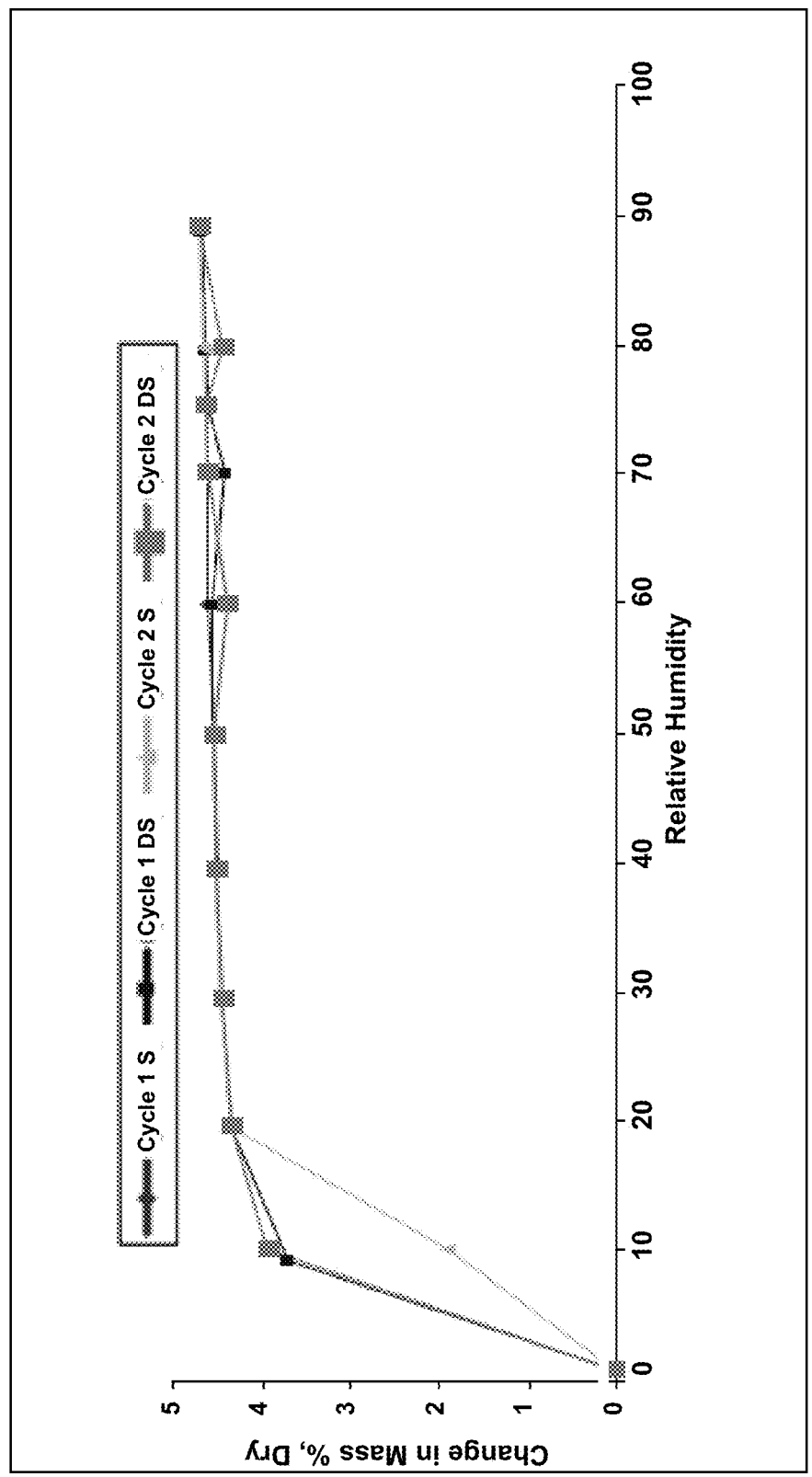
FIG. 12: GVS Isotherm Plot of 8-(4-Methylpiperazin-1-yl)-5-(thiophen-2-yl)tetrazolo[1,5-a]pyrazine Mesylate Monohydrate Form 1, also known as Compound 1, Mesylate Salt, Form 1.

| Position (cm$^{-1}$) | Intensity |
|---|---|
| 548.5 | 11.1 |
| 626.8 | 15.9 |
| 794.9 | 9.3 |
| 1044.9 | 10.7 |
| 1058.3 | 9.9 |
| 1076.3 | 10.3 |
| 1231.5 | 14.8 |
| 1299.2 | 20.1 |
| 1312.9 | 25.6 |
| 1353.6 | 88.0 |
| 1422.2 | 60.1 |
| 1494.3 | 39.7 |
| 1522.7 | 75.6 |
| 1546.7 | 14.3 |
| 1589.5 | 69.6 |
| 2931.8 | 11.1 |
| 3004.1 | 10.0 | iv) DSC/TGA: The DSC/TGA curves for Compound 1, Mesylate Salt, Form 1 is depicted in FIG. 11. The DSC curve exhibits a broad dehydration event between 50 to 110° C. followed by simultaneous melting and decomposition events at approximately 230° C. TGA-IR analysis showed a loss of 4% water below 100° C.

v) GVS: The GVS isotherm plot for Compound 1, Mesylate Salt Form 1 is depicted in FIG. 12. The water content (~4.3%) remained relatively constant between 20-90% RH. There was a loss of ~4.30% water below 20% RH. The results are consistent with the thermal analysis and indicate that Compound 1 Mesylate Salt Form 1 is not hydroscopic. FT-Raman analysis before and after GVS confirmed that there was no crystal form change.

vi) X-ray Crystal Structure Determination:

Data Collection and Processing.

A single crystal of 8-(4-Methylpiperazin-1-yl)-5-(thiophen-2-yl)tetrazolo[1,5-a]pyrazine mesylate, monohydrate, Form 1 was mounted on a Mitegen polyimide micromount with a small amount of Paratone N oil. All X-ray measurements were made on a Bruker-Nonius Kappa Axis X8 Apex2 diffractometer at a temperature of 110 K. The unit cell dimensions were determined from a symmetry constrained fit of 9906 reflections with 5.34°<2θ<77.18°. The data collection strategy was a number of ω and φ scans which collected data up to 86.42° (2θ). The frame integration was performed using SAINT (Bruker-Nonius, SAINT version 2009.9, 2009, Bruker-Nonius, Madison, Wis. 53711, USA). The resulting raw data was scaled and absorption corrected using a multi-scan averaging of symmetry equivalent data using SADABS (Bruker-Nonius, SADABS version 2009.9).

Structure Solution and Refinement.

The structure was solved by direct methods using the XS program (Bruker-AXS, XS version 2009.9). Most non-hydrogen atoms were obtained from the initial solution. The remaining positions were obtained from subsequent difference Fourier maps.

The structure exhibits two independent disorders, one in the cation and one on the anion. The cation disorder involves an approximate 180° rotation of the thiophene ring. This interchanges the position of atom S1 and C3. The disorder was model by introducing 2 sets of atoms, the major component consisting of S1, C1, C2, C3, C4, and minor component consisting of S1', C1', C2', C3', C4'. The position for S1' was distinct, while C1' was coincident with C2, C2' was coincident with C1, C3' was coincident with S1 and C4' was coincident with C4. Difference maps showed a peak of approximately 1.3e$^-$/Å$^3$ near the C2/C1' site. An attempt to fit this peak to a distinct C1' site did not yield a refinement with reasonable even constraints in the least-squares model. The final refinements assumed that sites for C2 and C1' were coincident. The normalized occupancy refined to a value of 0.7893(14) for the major orientation of the thiophene ring.

The anion was disordered over 2 orientations. The S2 site for both orientations was coincident while all other atoms in the anion occupied distinct sites. The angle between the orientation is indicated by the angle C14-S2-C14' which was approximately 23°. The normalized occupancy for the major orientation refined to a value of 0.892(4).

Figure 13:
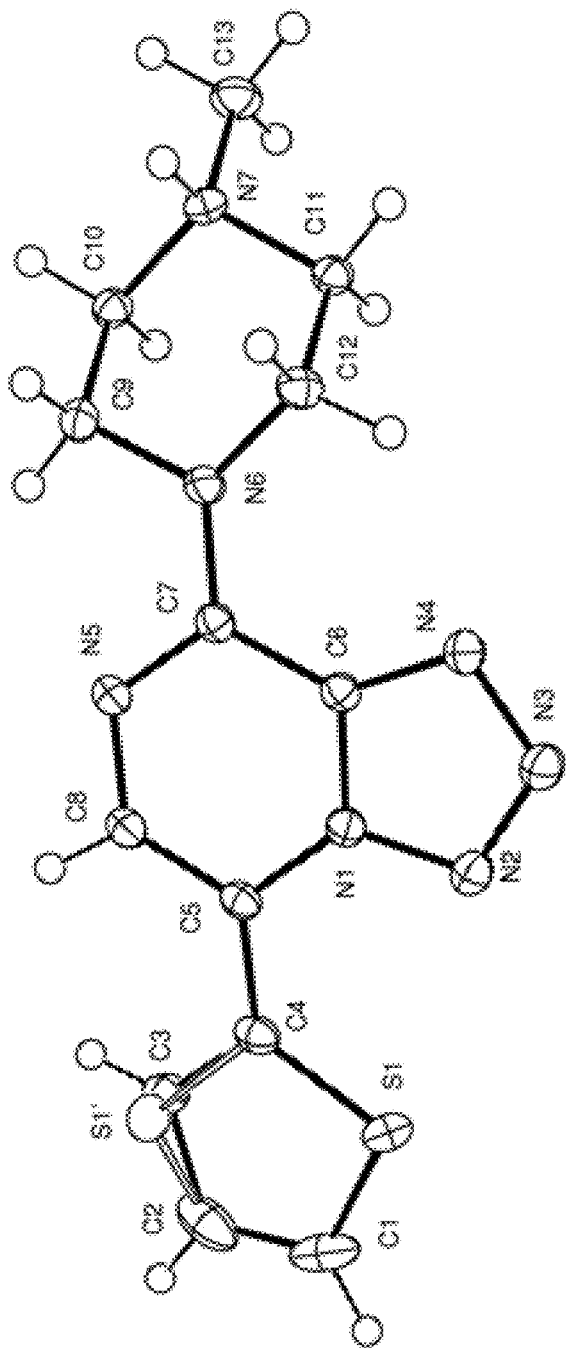
FIG. 13: ORTEP drawing of the 8-(4-methylpiperazin-1-yl)-5-(thiophen-2-yl)tetrazolo[1,5-a]pyrazine Mesylate Monohydrate Form 1 cation showing the atom naming and numbering scheme. Ellipsoids are at the 50% probability level and hydrogen atoms were drawn with arbitrary radii for clarity. The disordered sulfur atom is depicted with an open ellipsoid and open bonds.
Figure 14:
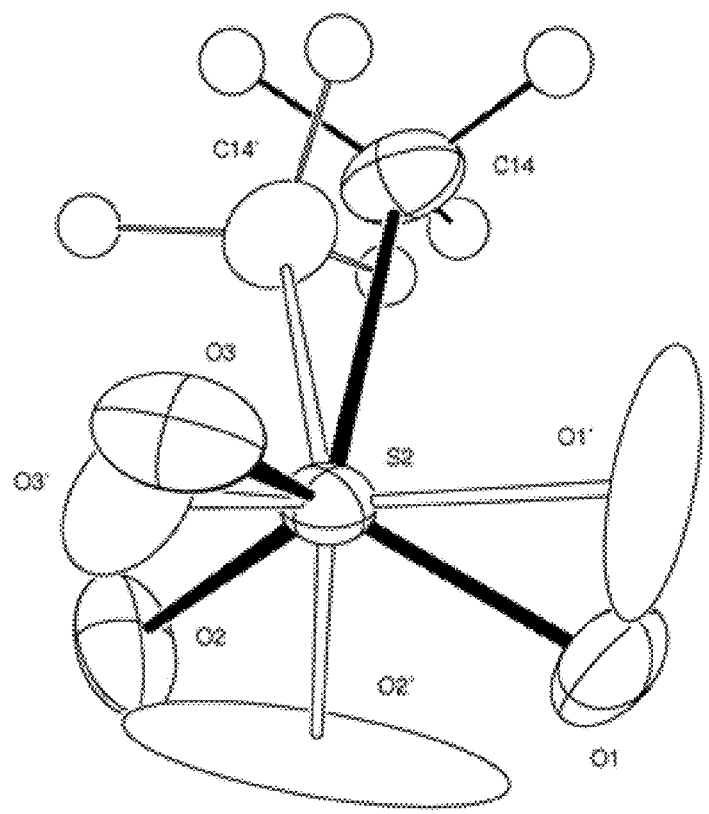
FIG. 14: ORTEP drawing of the 8-(4-methylpiperazin-1-yl)-5-(thiophen-2-yl)tetrazolo[1,5-a]pyrazine Mesylate Monohydrate Form 1 anion showing the atom naming and numbering scheme. Ellipsoids are at the 50% probability level and hydrogen atoms were drawn with arbitrary radii for clarity. The disordered component is drawn with open ellipsoids and bonds.

The hydrogen atoms were introduced at idealized positions and were treated in a mixed fashion. The hydrogen atoms in the ordered regions of the structure were allowed to refine isotropically while the hydrogen atoms in the disordered regions were allowed to ride on the parent atom. The hydrogen atom positions on the water oxygen were derived from a difference Fourier map. The structural model was fit to the data using full matrix least-squares based on F$^2$. The calculated structure factors included corrections for anomalous dispersion from the usual tabulation. The structure was refined using the XL program from SHELXTL, graphic plots were produced using the NRCVAX crystallographic program suite. Results are shown below in Tables 8-11 and in FIGS. 13 and 14.

TABLE 8

Summary Crystal Data: Compound 1 Mesylate Monohydrate, Form 1

| Identification Code | Compound 1 Mesylate |
|---|---|
| Formula | C$_{14}$H$_{21}$N$_7$O$_4$S$_2$ |
| Formula Weight (g/mol) | 415.50 |
| Crystal Dimensions (mm) | 0.30 × 0.26 × 0.25 |
| Crystal Color and Habit | colourless prism |
| Crystal System | Triclinic |
| Space Group | P-1 |
| Temperature, K | 110 |
| a, Å | 6.706(2) |
| b, Å | 8.396(2) |
| c, Å | 16.978(4) |
| α,° | 81.095(19) |
| β,° | 80.260(14) |
| γ,° | 76.100(13) |
| V, Å$^3$ | 908.0(4) |
| Number of reflections to determine final unit cell | 9906 |
| Min & Max 2θ for cell detn, ° | 5.34, 77.18 |
| Z | 2 |
| F(000) | 436 |
| ρ (g/cm) | 1.520 |
| λ, Å, (MoKα) | 0.71073 |
| μ, (cm$^{-1}$) | 0.332 |
| Diffractometer Type | Bruker-Nonius Kappa Axis X8 Apex2 |
| Scan Type(s) | omega and phi scans |
| Max 2θ for data collection, ° | 86.42 |
| Measured fraction of data | 0.984 |
| Number of reflections measured | 55627 |
| Unique reflections measured | 12971 |
| R$_{merge}$ | 0.0274 |
| Number of reflections included in refinement | 12971 |
| Cut off Threshold Expression | >2sigma(I) |
| Structure refined using | full matrix least-squares using F$^2$ |
| Weighting Scheme | Calcw = 1/[sigma$^2$(Fo$^2$) + (0.0625P)$^2$ + 0.0983P] where P = (Fo$^2$ + 2Fc$^2$)/3 |

TABLE 8-continued

Summary Crystal Data: Compound 1 Mesylate Monohydrate, Form 1

| Identification Code | Compound 1 Mesylate |
|---|---|
| Number of parameters in least-squares | 353 |
| $R_1$ | 0.0447 |
| $wR_2$ | 0.1144 |
| $R_1$ (all data) | 0.0687 |
| $wR_2$ (all data) | 0.1255 |
| GOF | 1.060 |
| Maximum shift/error | 0.002 |
| Min & Max peak heights on final ΔF Map (e⁻/Å) | −0.797, 1.302 |

TABLE 9

Atomic Coordinates for Compound 1 Mesylate Monohydrate, Form 1

| Atom | x | Y | Z | $U_{iso/equiv}$ |
|---|---|---|---|---|
| S1 | 0.69797(4) | 0.03947(3) | 0.597240(15) | 0.02220(7) |
| C1 | 0.5822(2) | −0.07071(11) | 0.67364(6) | 0.0330(2) |
| C2 | 0.3706(2) | −0.02735(13) | 0.67948(6) | 0.0358(2) |
| C3 | 0.2995(7) | 0.1015(5) | 0.61509(14) | 0.0225(4) |
| C4 | 0.47265(13) | 0.15065(9) | 0.56772(4) | 0.01878(12) |
| S1' | 0.2828(6) | 0.1027(5) | 0.63374(14) | 0.0259(5) |
| C1' | 0.3706(2) | −0.02735(13) | 0.67948(6) | 0.0358(2) |
| C2' | 0.5822(2) | −0.07071(11) | 0.67364(6) | 0.0330(2) |
| C3' | 0.69797(4) | 0.03947(3) | 0.597240(15) | 0.02220(7) |
| C4' | 0.47265(13) | 0.15065(9) | 0.56772(4) | 0.01878(12) |
| C5 | 0.45103(12) | 0.27895(9) | 0.49981(4) | 0.01653(11) |
| N1 | 0.61860(10) | 0.30314(8) | 0.44278(4) | 0.01570(10) |
| N2 | 0.82000(11) | 0.22518(9) | 0.44421(4) | 0.02066(12) |
| N3 | 0.92154(11) | 0.28471(11) | 0.37813(5) | 0.02339(13) |
| N4 | 0.79540(10) | 0.39905(9) | 0.33335(4) | 0.02012(12) |
| C6 | 0.60447(11) | 0.41025(9) | 0.37412(4) | 0.01549(11) |
| C7 | 0.40154(11) | 0.50528(9) | 0.35970(4) | 0.01533(11) |
| N5 | 0.24203(10) | 0.49362(8) | 0.41624(4) | 0.01820(11) |
| C8 | 0.26747(12) | 0.38308(10) | 0.48311(4) | 0.01879(12) |
| N6 | 0.36894(10) | 0.59998(9) | 0.28895(4) | 0.01820(11) |
| C9 | 0.15911(12) | 0.68583(10) | 0.27475(5) | 0.01932(13) |
| C10 | 0.12452(11) | 0.66585(9) | 0.19131(5) | 0.01716(12) |
| N7 | 0.28643(10) | 0.72183(8) | 0.12857(4) | 0.01634(10) |
| C11 | 0.49896(11) | 0.63176(9) | 0.14597(4) | 0.01647(11) |
| C12 | 0.52948(12) | 0.65612(10) | 0.22952(5) | 0.01830(12) |
| C13 | 0.25388(14) | 0.70349(12) | 0.04620(5) | 0.02387(15) |
| S2 | 1.22139(3) | 0.19829(2) | 0.102805(11) | 0.01754(4) |
| O3 | 1.3460(3) | 0.30462(15) | 0.12100(12) | 0.0312(3) |
| O2 | 1.2670(2) | 0.03656(11) | 0.15067(7) | 0.0375(3) |
| O1 | 1.23566(17) | 0.18381(17) | 0.01825(6) | 0.0349(2) |
| C14 | 0.96000(18) | 0.28738(18) | 0.13466(9) | 0.0270(3) |
| S2' | 1.22139(3) | 0.19829(2) | 0.102805(11) | 0.01754(4) |
| O1' | 1.1837(19) | 0.294(3) | 0.0236(5) | 0.076(7) |
| O2' | 1.2889(18) | 0.0384(12) | 0.087(2) | 0.131(13) |
| O3' | 1.363(2) | 0.2557(15) | 0.1293(7) | 0.030(2) |
| C14' | 0.9942(16) | 0.2238(18) | 0.1635(7) | 0.030(2) |
| O1W | 0.74775(11) | −0.03393(9) | 0.11716(5) | 0.02876(14) |
| H1 | 0.6552 | −0.1545 | 0.7093 | 0.040 |
| H2 | 0.2800 | −0.0752 | 0.7205 | 0.043 |
| H3 | 0.1592 | 0.1447 | 0.6068 | 0.027 |
| H1' | 0.2879 | −0.0907 | 0.7163 | 0.043 |
| H2' | 0.6552 | −0.1545 | 0.7093 | 0.040 |
| H3' | 0.8392 | 0.0396 | 0.5775 | 0.027 |
| H8 | 0.143(2) | 0.3792(16) | 0.5189(8) | 0.026(3) |
| H9A | 0.1399(19) | 0.8013(16) | 0.2802(8) | 0.024(3) |
| H9B | 0.0630(19) | 0.6403(15) | 0.3136(8) | 0.022(3) |
| H10A | 0.1316(18) | 0.5499(15) | 0.1870(7) | 0.017(3) |
| H10B | −0.011(2) | 0.7328(18) | 0.1806(8) | 0.030(3) |
| H7 | 0.272(2) | 0.8283(17) | 0.1300(8) | 0.028(3) |
| H11A | 0.5910(19) | 0.6728(16) | 0.1052(8) | 0.022(3) |
| H11B | 0.5128(17) | 0.5211(16) | 0.1395(7) | 0.015(3) |
| H12A | 0.671(2) | 0.5937(17) | 0.2378(8) | 0.029(3) |
| H12B | 0.5249(18) | 0.7694(15) | 0.2314(7) | 0.018(3) |
| H13A | 0.267(2) | 0.5949(18) | 0.0427(8) | 0.030(3) |
| H13B | 0.356(2) | 0.7482(16) | 0.0070(8) | 0.024(3) |
| H13C | 0.114(2) | 0.7702(18) | 0.0363(9) | 0.036(4) |

TABLE 9-continued

Atomic Coordinates for Compound 1 Mesylate Monohydrate, Form 1

| Atom | x | Y | Z | $U_{iso/equiv}$ |
|---|---|---|---|---|
| H14A | 0.9434 | 0.3061 | 0.1912 | 0.040 |
| H14B | 0.8727 | 0.2126 | 0.1290 | 0.040 |
| H14C | 0.9184 | 0.3930 | 0.1015 | 0.040 |
| H14D | 1.0176 | 0.1774 | 0.2187 | 0.045 |
| H14E | 0.9019 | 0.1671 | 0.1451 | 0.045 |
| H14F | 0.9302 | 0.3420 | 0.1623 | 0.045 |
| H1WA | 0.749(2) | −0.0665(17) | 0.0741(9) | 0.028(3) |
| H1WB | 0.611(3) | 0.010(3) | 0.1313(12) | 0.073(6) |

TABLE 10

Bond Lengths for Compound 1 Mesylate Monohydrate Form 1

| Bond | Length, Å | Bond | Length, Å |
|---|---|---|---|
| S1-C1 | 1.6653(12) | C10-N7 | 1.4945(10) |
| S1-C4 | 1.6850(10) | C10-H10A | 0.977(12) |
| C1-C2 | 1.3683(19) | C10-H10B | 0.976(14) |
| C1-H1 | 0.9500 | N7-C13 | 1.4876(11) |
| C2-C3 | 1.468(4) | N7-C11 | 1.4986(11) |
| C2-H2 | 0.9500 | N7-H7 | 0.879(14) |
| C3-C4 | 1.406(4) | C11-C12 | 1.5180(11) |
| C3-H3 | 0.9500 | C11-H11A | 0.929(13) |
| C4-C5 | 1.4518(11) | C11-H11B | 0.933(12) |
| C5-C8 | 1.3726(11) | C12-H12A | 0.991(14) |
| C5-N1 | 1.3864(10) | C12-H12B | 0.950(12) |
| N1-N2 | 1.3544(10) | C13-H13A | 0.905(14) |
| N1-C6 | 1.3596(10) | C13-H13B | 0.970(13) |
| N2-N3 | 1.3052(11) | C13-H13C | 0.994(14) |
| N3-N4 | 1.3478(10) | S2-O1 | 1.4447(10) |
| N4-C6 | 1.3378(10) | S2-O3 | 1.4567(15) |
| C6-C7 | 1.4419(11) | S2-O2 | 1.4631(9) |
| C7-N5 | 1.3225(10) | S2-C14 | 1.7604(12) |
| C7-N6 | 1.3538(10) | C14-H14A | 0.9800 |
| N5-C8 | 1.3574(11) | C14-H14B | 0.9800 |
| C8-H8 | 0.951(13) | C14-H14C | 0.9800 |
| N6-C12 | 1.4589(10) | C14'-H14D | 0.9800 |
| N6-C9 | 1.4599(11) | C14'-H14E | 0.9800 |
| C9-C10 | 1.5140(11) | C14'-H14F | 0.9800 |
| C9-H9A | 0.964(13) | O1W-H1WA | 0.818(15) |
| C9-H9B | 0.945(12) | O1W-H1WB | 0.91(2) |

TABLE 11

Bond Angles for Compound 1 Mesylate Monohydrate, Form 1

| Bond | Angle° | Bond | Angle° |
|---|---|---|---|
| C1-S1-C4 | 93.80(5) | C10-C9-H9B | 109.5(8) |
| C2-C1-S1 | 112.59(7) | H9A-C9-H9B | 108.9(11) |
| C2-C1-H1 | 123.7 | N7-C10-C9 | 111.11(6) |
| S1-C1-H1 | 123.7 | N7-C10-H10A | 107.6(7) |
| C1-C2-C3 | 112.25(18) | C9-C10-H10A | 110.4(7) |
| C1-C2-H2 | 123.9 | N7-C10-H10B | 108.3(8) |
| C3-C2-H2 | 123.9 | C9-C10-H10B | 109.2(8) |
| C4-C3-C2 | 109.0(3) | H10A-C10-H10B | 110.1(11) |
| C4-C3-H3 | 125.5 | C13-N7-C10 | 111.69(6) |
| C2-C3-H3 | 125.5 | C13-N7-C11 | 111.37(6) |
| C3-C4-C5 | 121.78(18) | C10-N7-C11 | 110.50(6) |
| C3-C4-S1 | 112.23(17) | C13-N7-H7 | 106.2(9) |
| C5-C4-S1 | 125.94(6) | C10-N7-H7 | 107.0(9) |
| C8-C5-N1 | 113.12(7) | C11-N7-H7 | 109.8(9) |
| C8-C5-C4 | 124.96(7) | N7-C11-C12 | 110.18(6) |
| N1-C5-C4 | 121.87(7) | N7-C11-H11A | 105.9(8) |
| N2-N1-C6 | 108.47(6) | C12-C11-H11A | 113.4(8) |
| N2-N1-C5 | 127.10(7) | N7-C11-H11B | 107.3(7) |
| C6-N1-C5 | 124.42(7) | C12-C11-H11B | 113.1(7) |
| N3-N2-N1 | 105.83(7) | H11A-C11-H11B | 106.4(10) |
| N2-N3-N4 | 112.02(7) | N6-C12-C11 | 109.62(6) |
| C6-N4-N3 | 105.77(7) | N6-C12-H12A | 112.9(8) |
| N4-C6-N1 | 107.90(7) | C11-C12-H12A | 106.6(8) |

TABLE 11-continued

Bond Angles for Compound 1 Mesylate Monohydrate, Form 1

| Bond | Angle° | Bond | Angle° |
|---|---|---|---|
| N4-C6-C7 | 134.31(7) | N6-C12-H12B | 110.8(7) |
| N1-C6-C7 | 117.79(6) | C11-C12-H12B | 109.5(7) |
| N5-C7-N6 | 119.37(7) | H12A-C12-H12B | 107.3(10) |
| N5-C7-C6 | 118.67(7) | N7-C13-H13A | 108.6(9) |
| N6-C7-C6 | 121.89(7) | N7-C13-H13B | 109.3(8) |
| C7-N5-C8 | 120.08(7) | H13A-C13-H13B | 110.7(12) |
| N5-C8-C5 | 125.55(7) | N7-C13-H13C | 108.5(9) |
| N5-C8-H8 | 114.1(8) | H13A-C13-H13C | 112.2(12) |
| C5-C8-H8 | 120.3(8) | H13B-C13-H13C | 107.5(11) |
| C7-N6-C12 | 125.22(7) | O1-S2-O3 | 114.67(9) |
| C7-N6-C9 | 120.22(6) | O1-S2-O2 | 111.86(7) |
| C12-N6-C9 | 113.19(6) | O3-S2-O2 | 110.16(8) |
| N6-C9-C10 | 110.06(6) | O1-S2-C14 | 106.18(6) |
| N6-C9-H9A | 109.3(8) | O3-S2-C14 | 107.25(7) |
| C10-C9-H9A | 110.0(8) | O2-S2-C14 | 106.18(7) |
| N6-C9-H9B | 108.9(7) | H1WA-O1W-H1WB | 102.4(15) |

SCHEME 3

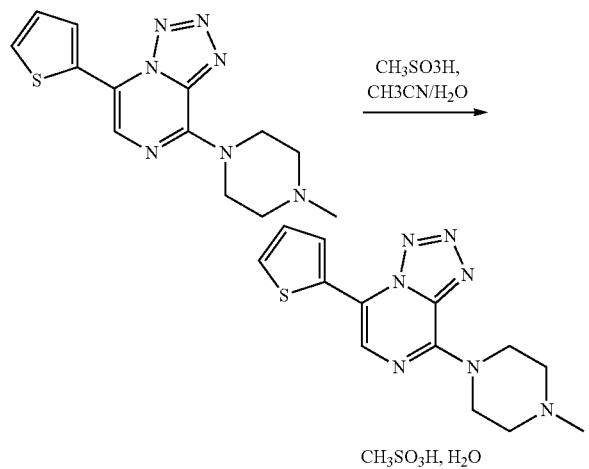

Alternative Preparation Compound 1 Mesylate Salt, Form 1

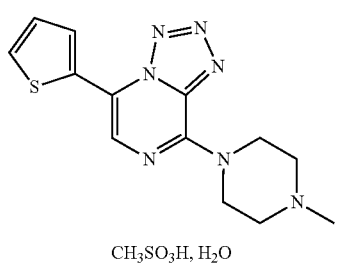 [SMILES: CN1CCN(c2ncc(-c3cccs3)n3nnnc23)CC1]

8-(4-Methylpiperazin-1-yl)-5-(thiophen-2-yl)tetrazolo[1,5-a]pyrazine Mesylate Monohydrate, Form 1

8-(4-Methylpiperazin-1-yl)-5-(thiophen-2-yl)tetrazolo[1,5-a]pyrazine (90 g, 0.298 mol 1.0 eq.) purified water (950 ml) and methanesulfonic acid (43.05 g 0.448 mol, 1.5 eq) were combined and the resulting solution heated to 50-55° C. The solution was washed with toluene (2×1 L) and the pH of the remaining aqueous phase adjusted to 9.5-10.5 by addition of sodium hydroxide (27%). The product precipitated during the pH adjustment, was isolated, suspended in toluene (2.5 L) and heated to 55-60° C. The resulting organic solution was washed with 1% cysteine solution and the pH of the solution is adjusted to 8.8-9.2 by addition of sodium hydroxide (27%). The separated organic phase was then washed with purified water at 55.60° C. 3-mercaptopropyl ethyl sulfide silica was added top the separated organic phase and the mixture is stirred for 20 minutes at 55-60° C. Activated carbon was added and the organic phase stirred for 20 minutes at 55-60° C., then filtered through a pad of Celite. The filter cake is washed with toluene, and the wash combined with the filtrate.

To the combined filtrates was added a solution of methanesulfonic acid in purified water, and the mixture stirred until all the product is extracted from the toluene phase into the aqueous phase. The aqueous phase was subjected to clear filtration. The pH of the filtrate was adjusted to 9.5-10.5 by addition of 27% aqueous sodium hydroxide. The precipitated free base was isolated, and dried in vacuum at 35° C. until the water content in the product does not exceed 21.7%. The partially dried material was suspended in acetonitrile (5.45 g/g crude material) and purified water (0.278 g/g crude material), heated to 55-60° C., and methanesulfonic acid (0.344 g/g crude material 1.08 eq) added. The clear solution was seeded at 60-70° C. and cooled to 50-60° C. The suspension was cooled to 5-10° C. and the product isolated, washed with acetonitrile, dried in vacuum at 30° C. and allowed to equilibrate in a moist atmosphere (92.9 g, 75%).

Compound 1, monomethanesulfonate monohydrate exhibits >5-fold improvement in solubility over Compound 1 in aqueous acetate buffer (80 mM) at pH3.5-4.5.

Characterization of Compound 1 Mesylate Salt Form 2

Figure 15:
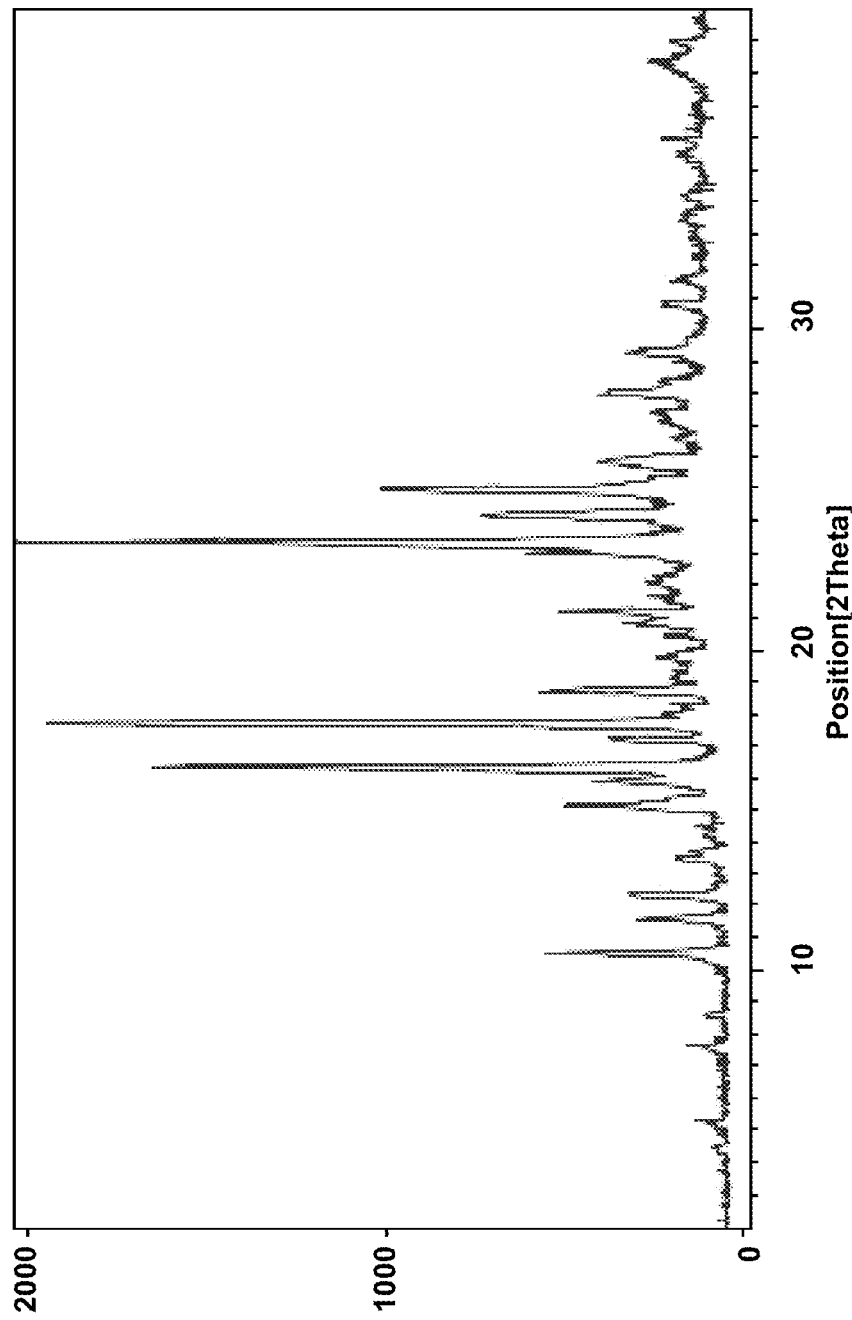
FIG. 15: PXRD diffractogram of 8-(4-Methylpiperazin-1-yl)-5-(thiophen-2-yl)tetrazolo[1,5-a]pyrazine Mesylate Form 2, also known as Compound 1 Mesylate Salt Form 2.

Compound 1 Mesylate Salt Form 2 was characterized as follows:

i) PXRD: The PXRD diffractogram of Compound 1, Mesylate Salt, Form 2 is depicted in FIG. 15; the associated PXRD Peaks are listed in Table 12 (where * indicates ±0.2° and ** indicates the relative intensity for each peak is determined by normalizing its intensity to that of the strongest peak at 23.4° angle as 100).

TABLE 12

PXRD Peaks of Compound 1 Mesylate Salt Form 2
PXRD Peaks of
Compound 1 Mesylate Form 2

| Two-Theta Angle* (degree) | Relative Intensity** (arbitrary) |
|---|---|
| 10.6 | 24.9 |
| 11.6 | 9.4 |
| 12.3 | 12.5 |
| 15.1 | 20.8 |
| 15.9 | 16.7 |
| 16.4 | 69.1 |
| 17.2 | 15.3 |
| 17.7 | 97.9 |
| 18.7 | 24.6 |
| 21.0 | 11.1 |
| 23.4 | 100.0 |
| 24.2 | 32.1 |
| 25.0 | 46.8 |
| 25.9 | 13.9 |

TABLE 12-continued

PXRD Peaks of Compound 1 Mesylate Salt Form 2
PXRD Peaks of
Compound 1 Mesylate Form 2

Figure 16:
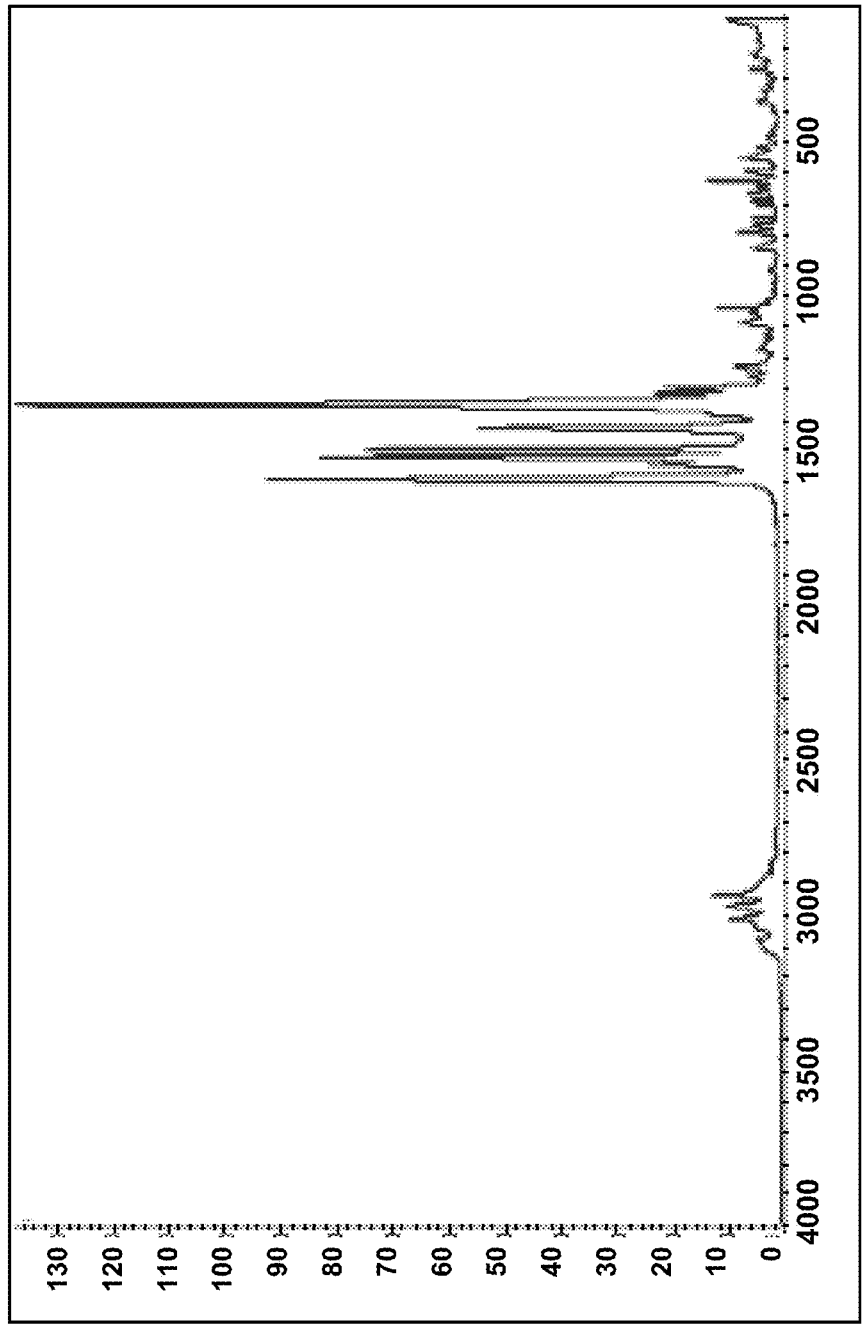
FIG. 16: FT-Raman Spectrum of 8-(4-Methylpiperazin-1-yl)-5-(thiophen-2-yl)tetrazolo[1,5-a]pyrazine Mesylate Form 2, also known as Compound 1 Mesylate Form 2. In the figure, the horizontal axis is the Raman shift in units of $cm^{-1}$.

| Two-Theta Angle* (degree) | Relative Intensity** (arbitrary) |
|---|---|
| 28.1 | 12.1 |
| 29.3 | 9.9 | ii) FT-Raman: The FT-Raman Spectrum of Compound 1, Mesylate Salt, Form 2 is depicted in FIG. 16; the associated FT-Raman Peaks are listed in Table 13.

TABLE 13

FT-Raman Peaks of Compound 1 Mesylate Salt Form 2
FT-Raman Peaks of
Compound 1 Mesylate Form 2

| Position (cm$^{-1}$) | Intensity |
|---|---|
| 626.1 | 13.6 |
| 794.1 | 8.4 |
| 1037.0 | 11.6 |
| 1226.5 | 8.6 |
| 1295.9 | 21.3 |
| 1312.5 | 23.1 |
| 1352.2 | 137.4 |
| 1423.5 | 54.4 |
| 1493.9 | 74.5 |
| 1521.6 | 82.8 |
| 1541.9 | 23.9 |
| 1589.8 | 92.4 |
| 2934.5 | 12.6 |
| 2970.5 | 9.8 |
| 3011.5 | 9.6 |

Characterization of Compound 1 Mesylate Salt Form 3

Compound 1 Mesylate Salt Form 1 was characterized as follows:

i) PXRD: The PXRD diffractogram of Compound 1, Mesylate Salt, Form 2 is depicted in FIG. 17; the associated PXRD Peaks are listed in Table 14 (where * indicates ±0.2° and ** indicates the relative intensity for each peak is determined by normalizing its intensity to that of the strongest peak at 24.0° angle as 100).

TABLE 14

PXRD Peaks of Compound 1 Mesylate Salt Form 3
PXRD Peaks of
Compound 1 Mesylate Form 3 (Anhydrous)

| Two-Theta Angle* (degree) | Relative Intensity** (arbitrary) |
|---|---|
| 7.8 | 18.7 |
| 10.4 | 23.1 |
| 13.2 | 8.0 |
| 15.1 | 11.6 |
| 16.3 | 43.3 |
| 17.2 | 27.0 |
| 17.8 | 46.0 |
| 19.6 | 18.8 |
| 22.8 | 45.8 |
| 24.0 | 100.0 |
| 26.5 | 12.6 |
| 27.8 | 55.3 |

TABLE 14-continued

PXRD Peaks of Compound 1 Mesylate Salt Form 3
PXRD Peaks of
Compound 1 Mesylate Form 3 (Anhydrous)

| Two-Theta Angle* (degree) | Relative Intensity** (arbitrary) |
|---|---|
| 29.4 | 8.9 |
| 32.9 | 12.4 | ii) FT-Raman: The FT-Raman Spectrum of Compound 1, Mesylate Salt, Form 2 is depicted in FIG. 18; the associated FT-Raman Peaks are listed in Table 15.

TABLE 15

FT-Raman Peaks of Compound 1, Mesylate Salt, Form 3
FT-Raman Peaks of
Compound 1 Mesylate Form 3 (Anhydrous)

Figure 19:
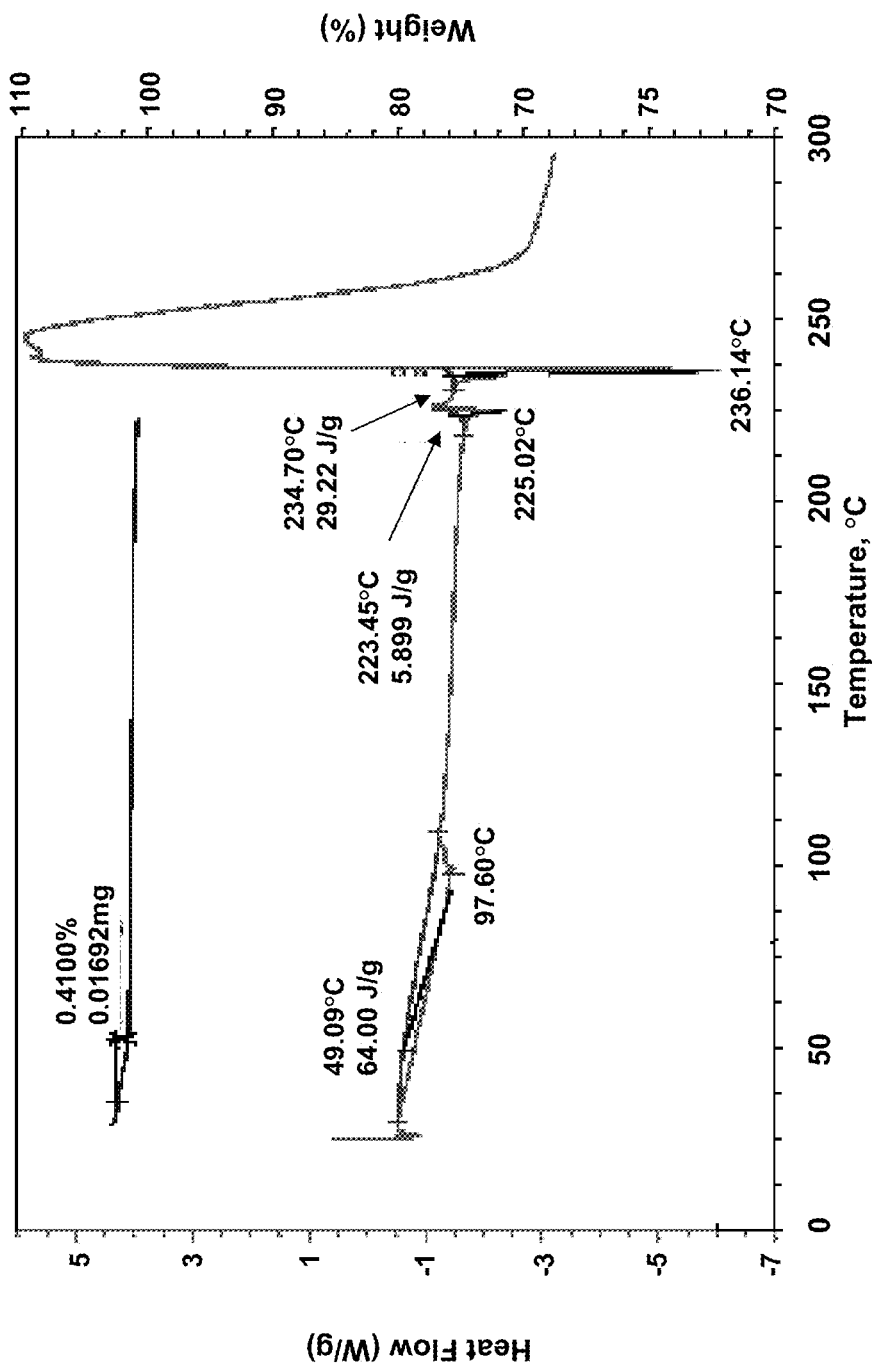
FIG. 19: DSC/TGA Analysis of 8-(4-Methylpiperazin-1-yl)-5-(thiophen-2-yl)tetrazolo[1,5-a]pyrazine Mesylate Form 3, also known as Compound 1, Mesylate Salt, Form 3.

| Position (cm$^{-1}$) | Intensity |
|---|---|
| 555.7 | 9.4 |
| 625.1 | 20.3 |
| 774.4 | 8.2 |
| 796.3 | 10.9 |
| 1034.5 | 11.1 |
| 1236.4 | 12.4 |
| 1269.8 | 11.3 |
| 1293.9 | 26.7 |
| 1309.6 | 25.1 |
| 1346.2 | 135.4 |
| 1422.6 | 89.4 |
| 1493.2 | 53.5 |
| 1524.1 | 116.6 |
| 1588.9 | 100.1 |
| 2931.0 | 14.6 |
| 3011.3 | 8.5 |
| 3084.5 | 9.6 | iii) DSC/TGA: The DSC scans Compound 1, Mesylate Salt, Form 3 is depicted in FIG. 19. The DSC curve indicates a melting onset at 223.5° C. followed by immediate recrystallization and subsequent melt/decomposition at 234.7° C. TGA-IR analysis indicated ~0.4% water loss below 50° C., suggesting that Compound 1, Mesylate Salt, Form 3 is a non-solvated form, Equilibrium Solubility Studies of Compound 1 Tartrate Salt Form 1, Compound 1 Tartrate Salt Form 2 and Compound 1 Mesylate Salt Form 1

Equilibrium solubility experiments were conducted for Compound 1 Tartrate Salt Form 1, Compound 1 Tartrate Salt Form 2 and Compound 1 Mesylate Salt Form 1 in water and pH-5 acetate buffer solution The results of the equilibrium solubility study are summarized in Table 16 (where "a" indicates Raman spectra of both samples matched each other, but were distinctly different from the known forms of FB or tartrate salt; NMR results showed a non-stoichiometric ratio of Free Base:Tartaric acid (1:0.8)).

TABLE 16

Equilibrium Solubility of Compound 1 Tartrate Salt Form 1,
Compound 1 Tartrate Salt Form 2
and Compound 1 Mesylate Salt Form 1

| Cpd. 1 Salt | Salt Weight (mg) | Solvent | Solvent (mL) | Residual Solid | Final pH | Filtrate Concentration (mg/mL) |
|---|---|---|---|---|---|---|
| Tartrate Form 1 | 24.6 | Water | 1.0 | Tartrate Form 1 | 3.48 | 8.18 |
| Tartrate Form 1 | 23.6 | 0.2M Acetate Buffer (pH5) | 1.0 | New Form/Salt[a] | 4.53 | 2.73 |
| Tartrate Form 2 | 29.1 | Water | 1.0 | Tartrate Form 2 | 3.55 | 4.43 |
| Tartrate Form 2 | 25.6 | 0.2M Acetate Buffer (pH5) | 1.0 | New Form/Salt[a] | 4.61 | 3.09 |
| Mesylate Form 1 | 50.7 | Water | 0.5 | Dissolved | 3.51 | >100 |
| Mesylate Form 1 | 53.1 | 0.2M Acetate Buffer (pH5) | 0.5 | Free Base | 4.17 | 58.2 |

Compound 1 Tartrate Salt Form 1 had solubility values of 8.18 mg/mL in water, but dissolution in 0.2M acetate buffer (pH5) resulted in a residual New Form/Salt with lower solubility of 2.73 mg/mL.

Compound 1 Tartrate Salt Form 2 had a solubility values of 4.43 mg/mL in water, but dissolution in 0.2M acetate buffer (pH5) resulted in a residual New Form/Salt with lower solubility of 3.09 mg/mL. Raman-FTIR spectra of both New Form/Salt samples matched each other, but were distinctly different from the known forms of Compound 1 and tartrate salt. NMR results showed a non-stoichiometric ratio of Compound 1 Free Base:Tartaric acid (1:0.8).

In the case of Compound 1 Mesylate Salt Form 1 in water, no residual solids were isolated as the sample completely dissolved. The equilibrium solubility of Compound 1 Mesylate Salt Form 1 is >100 mg/mL in water.

Compound 1 Mesylate Salt Form 1 in 0.2M Acetate Buffer (pH5) had equilibrium solubility of 58.2 mg/mL. The residual solid was identified as Compound 1 on the basis of Raman-FTIR analysis.

Compound 2

Salt Formation and Solid State Forms

In situ salt formation screening was performed by the method of Tong & Whitesell (Tong W-Q and Whitesell G *Pharmaceutical Development and Technology*, 1998, 3:215-223. Compound 2 was combined with 0.1M aqueous solutions of twelve acids at ambient temperature, reaction mixtures monitored, recharged with Compound 2 where appropriate and slurries temperature cycled between 5-40° C. for 48 hours. Reaction mixtures were then filtered and filtrant residual solids and filtrates analyzed as shown in Table 1 (where ND indicates Note Detectable).

TABLE 17

Results of In-Situ Salt Formation Screen for Compound 2.

| Cpd. 2 (mg) | Counterion | Filtrant PLM | FTIR | pH | Filtrate Solubility (mg/mL) |
|---|---|---|---|---|---|
| 55 | Acetic Acid | No Solids Isolated | | 5.41 | >24.53 |
| 25 | Citric Acid | Crystalline | Salt | 3.69 | 4.27 |
| 25.1 | Sulfuric Acid | Crystalline | Salt | 1.42 | 0.61 |
| 25 | Phosphoric Acid | Crystalline | Salt | 4.8 | 0.74 |
| 55 | Hydrochloric Acid | Crystalline | Salt | 2.32 | 15.25 |
| 40 | L-Aspartic Acid | No Solids Isolated | | 4.95 | >18.45 |
| 25 | L-Glutamic Acid | Crystalline | Free Base | 5.46 | 10.36 |
| 40 | L-Malic Acid | No Solids Isolated | | 5.13 | >21.1 |
| 25.1 | L-Tartaric Acid | Crystalline | Salt | 3.23 | 1.39 |
| 55 | Mesic Acid | No Solids Isolated | | 2.28 | >25.3 |
| 25.1 | Stearic Acid | Crystalline | Salt | 7.16 | ND |
| 40 | Succinic Acid | Crystalline | Salt | 4.75 | 0.1 |

The results indicate that Compound 2 sulfate, phosphate, L-tartrate and succinate salts have solubility of <5 mg/mL, whereas Compound 2 hydrochloride salt has solubility of >10 mg/mL under these conditions.

In certain embodiments, initially promising compounds are those which formed crystalline salts having high solubility in or near the range of pH4-5.

On the basis of the data presented in Table 17, three salt candidates, namely Compound 2 Citrate, Compound 2 Hydrochloride, and Compound 2 Mesylate were selected for more detailed assessment.

Compound 2 Citrate Salt

Crystallization experiments targeting the preparation of Compound 2 Citrate Salt were conducted in which the effect of solvent (acetone, acetonitrile, tetrahydrofuran, methanol, isopropyl alcohol, water/1% DMSO, ethyl acetate, dichloroethane, MTBE, Toluene, MIBK and dioxane) up crystallization by temperature cycling was surveyed.

Multiple crystal forms of Compound 2 Citrate Salt were obtained from these experiments. Compound 2 Citrate Salt Form 1 is a non-solvated, monocitrate solid state form that was obtained from six of the twelve screening experiments. Five other samples in the present study displayed unique FTIR & PXRD spectra, indicative of additional solid state forms and/or citrate salts of different stoichiometry. Two additional unique samples were obtained from equilibrium solubility experiments of Compound 2 Citrate Salt Form 1 in water and 0.2M Acetate buffer, pH 5.

Preparation of Compound 2 Citrate Salt, Form 1

Compound 2 (500 mg, 1.74 mmol) was added to 15 mL of acetone and the slurry heated, with stirring, to 40° C. Citric acid (1M in water, 1.75 mL, 1.0 eq.) was added to the slurry at 40° C. This solution was seeded with ~2 mg of Compound 2 Citrate salt Form 1 at 40° C. and stirred for 60 minutes resulting in a thick slurry. The slurry was cooled from 40° C. to 25° C. and then stirred at 25° C. for 16 hours. The solids were isolated by vacuum filtration, and rinsed and washed with acetone (~5 mL). The product was dried at 50° C. under vacuum for 3 hours to afford Compound 2 Citrate Salt, Form 1 (510 mg, 91% yield).

Compound 2 Citrate Salt Form 1 was characterized as follows:

i) $^1$H NMR: (500 MHz, D$_2$O) δ: 7.91 (s, 2H), 7.84 (d, J=3 Hz, 1H), 7.68 (d, J=5 Hz, 1H), 7.274, 7.268 (ABq, J$_{AB}$=3.75 Hz, 1H), 4.81 (brd, J=113 Hz, nd*), 4.46 (m, 1H), 2.90, 2.87 (s, s, 5H**), 2.78, 2.75 (d, J=15 Hz, 2H) (where * indicates nNot determined, obscured by DOH, and ** indicates combined).

ii) PXRD: The PXRD diffractogram of Compound 2 Citrate Salt Form 1 is depicted in FIG. 20; the associated PXRD Peaks are listed in Table 18 (where * indicates ±0.2° and ** indicates the relative intensity for each peak is determined by normalizing its intensity to that of the strongest peak at 18.9° angle as 100).

TABLE 18

PXRD Peaks of Compound 2, Citrate Salt, Form 1
PXRD Peaks of
Compound 2 Citrate Form 1

| Two-Theta Angle* (degree) | Relative Intensity** (arbitrary) |
|---|---|
| 9.4 | 37.2 |
| 9.9 | 9.2 |
| 11.1 | 12.7 |
| 12.4 | 18.0 |
| 18.9 | 100.0 |
| 19.9 | 49.1 |
| 24.9 | 10.1 |
| 26.2 | 76.9 |
| 28.6 | 74.4 |
| 31.4 | 9.3 |
| 33.4 | 4.7 |
| 36.2 | 8.0 |
| 39.0 | 6.7 | iii) FTIR: The FTIR Spectrum of Compound 2, Citrate Salt, Form 1 is depicted in FIG. 21; the associated FTIR Peaks are listed in Table 19.

TABLE 19

FTIR Peaks of Compound 2 Citrate Salt Form 1
FTIR Peaks of
Compound 2 Citrate Form 1

Figure 22:
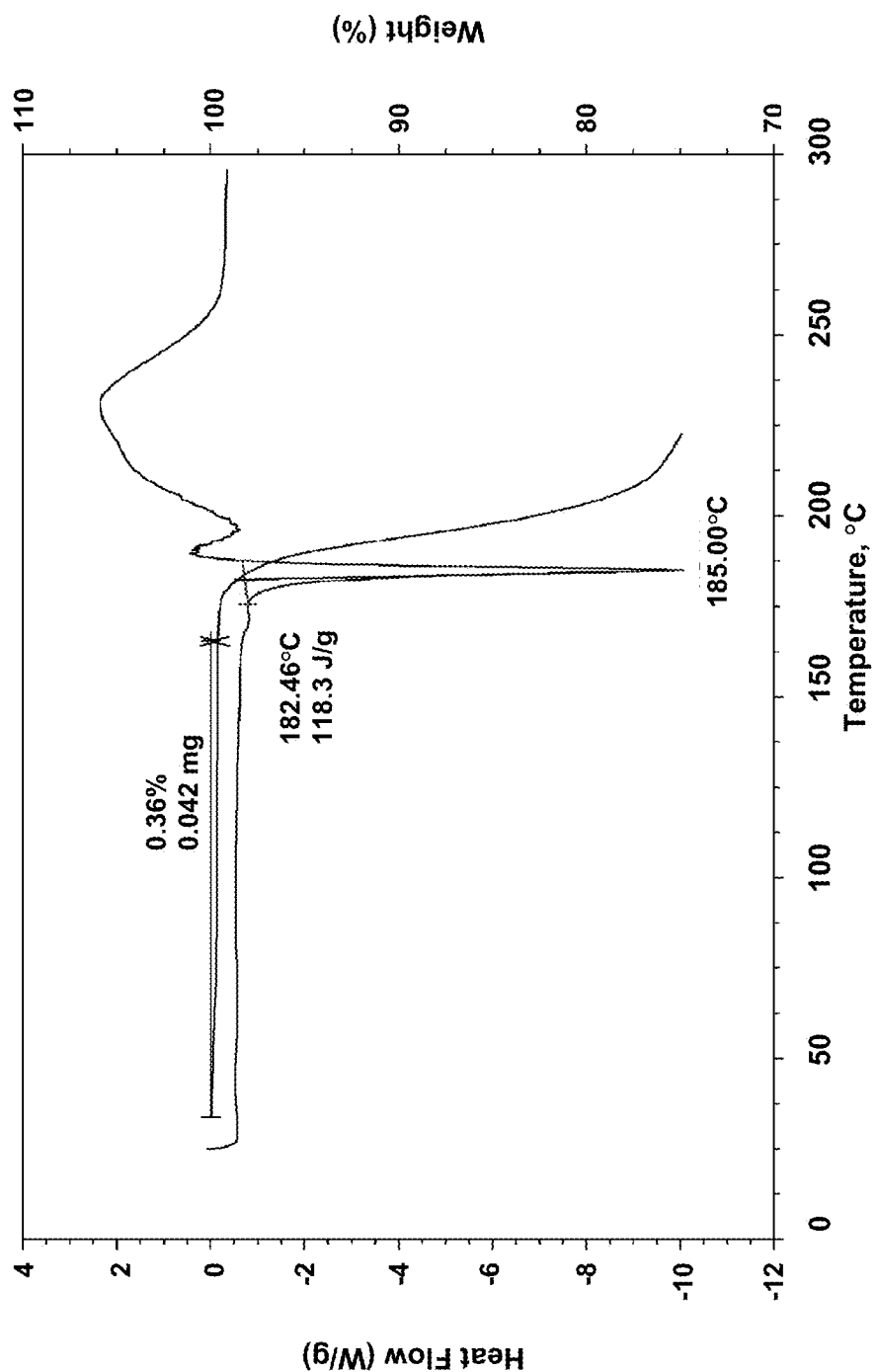
FIG. 22: DSC/TGA Analysis of N-methyl-1-(5-(thiophen-2-yl)tetrazolo[1,5-a]pyrazin-8-yl)azetidin-3-amine Citrate Form 1, also known as Compound 2 Citrate Salt Form 1.
Figure 23:
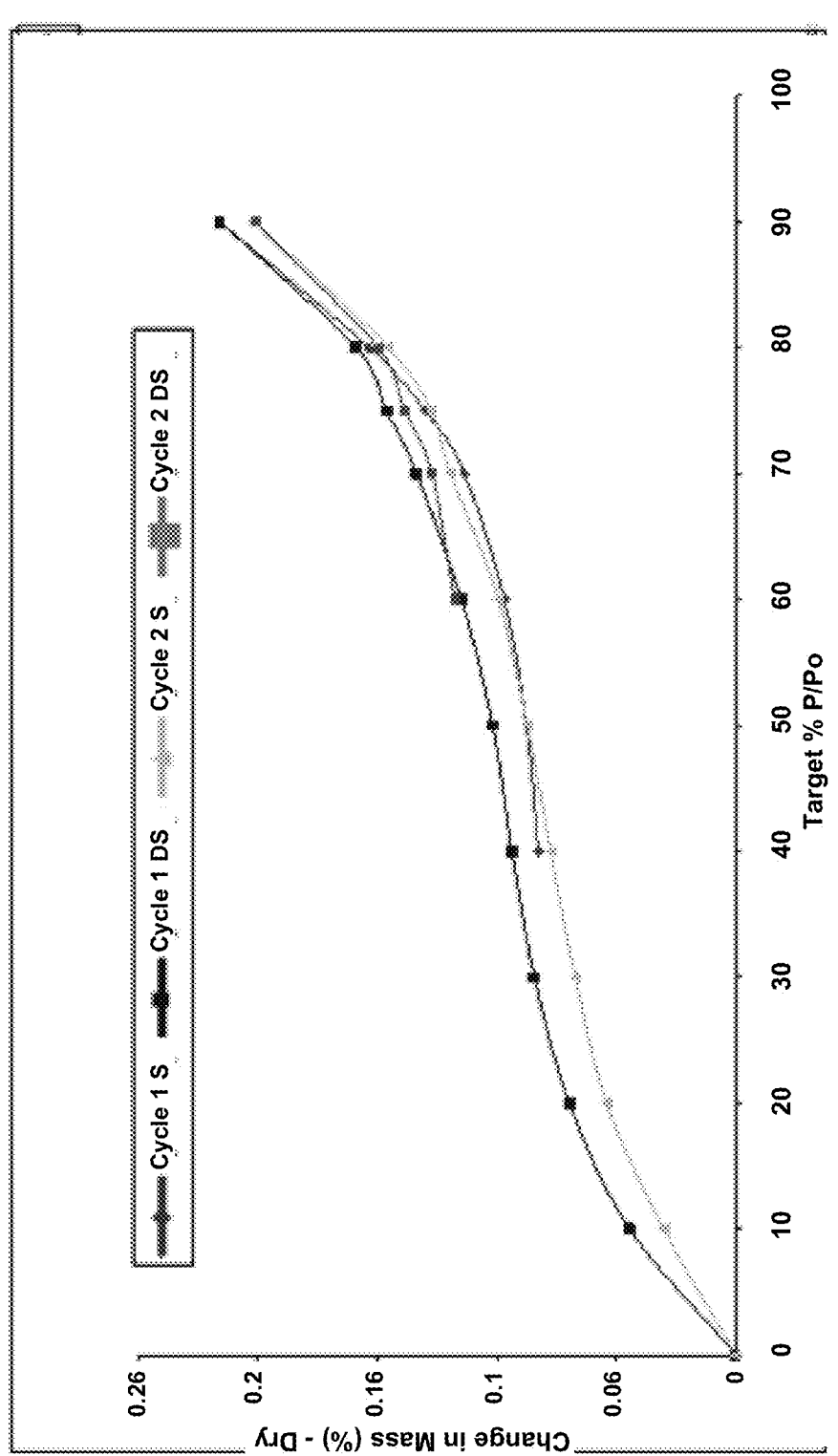
FIG. 23: GVS Isotherm Plot of N-methyl-1-(5-(thiophen-2-yl)tetrazolo[1,5-a]pyrazin-8-yl)azetidin-3-amine Citrate Form 1, also known as Compound 2 Citrate Salt Form 1. The last six data points of cycle 2 desorption were aberrant due to balance failure and not plotted.

| Position (cm$^{-1}$) | Intensity |
|---|---|
| 730.9 | 0.18 |
| 744.3 | 0.05 |
| 796.1 | 0.07 |
| 844.4 | 0.12 |
| 902.5 | 0.08 |
| 1110.1 | 0.14 |
| 1199.2 | 0.16 |
| 1209.3 | 0.12 |
| 1222.5 | 0.09 |
| 1309.5 | 0.13 |
| 1341.7 | 0.08 |
| 1372.2 | 0.07 |
| 1448.1 | 0.13 |
| 1564.0 | 0.19 |
| 1616.6 | 0.09 |
| 1710.8 | 0.06 | iv) DSC/TGA: The DSC/TGA scans Compound 2 Citrate Salt Form 1 is depicted in FIG. 22. DSC analysis indicates a broad melt onset at 171.4° C. TGA indicates neflible weight loss below 150° C.

v) GVS: The GVS curve for Compound 2 Citrate salt Form 1 is depicted in FIG. 23. The water content remained relatively constant between 0-90% RH, reaching a maximum weight increase of ~0.2% at 90% RH. These results indicate that Compound 2 Citrate Salt Form 1 is not hydroscopic. FTIR analysis of the sample before and after GVS confirmed that there was no change in crystal form.

Compound 2 Hydrochloride Salt

Crystallization experiments targeting the preparation of Compound 2 Hydrochloride Salt were conducted in which counterion stoichiometry, the effect of solvent (acetone, acetonitrile, tetrahydrofuran, methanol, isopropyl alcohol, water/1% DMSO, ethyl acetate, dichloroethane, MTBE, Toluene, MIBK and dioxane) and crystallization methods (temperature cycling, evaporation) were surveyed.

A single non-solvated form of Compound 2 Hydrochloride Salt was obtained from these experiments. Compound 2 Hydrochloride Salt Form 1 is a non-solvated anhydrous monohydrochloride solid state form that was obtained from all 24 crystallization experiments, regardless of whether one or two stoichiometric equivalents of hydrochloric acid were employed.

A Compound 2 Hydrochloride salt form screen was conducted involving about 160 crystallization experiments in 48 solvents and aqueous mixtures was performed conducted as previously described (vide supra).

Two crystal forms were identified and characterized in the context of this study.

Compound 2 Hydrochloride Form 1 is the predominant form and was obtained from a variety of crystallization conditions in many solvents and aqueous mixtures, including 48 slurry-ripening, 16 evaporative, 3 vapor diffusion and 5 solvent-antisolvent addition experiments.

Compound 2 Hydrochloride Form 2 was isolated from four evaporative crystallization experiments from aqueous mixtures. Compound 2 Hydrochloride Form 2 is poorly crystalline and difficult to scale up. The available data is consistent with a putative hydrate. DSC analysis shows a small endothermic event between 45 and 75° C. TGA was not performed due to limited sample size. A competitive ripening experiment conducted between Compound 2 Hydrochloride Salt Form 1 and Compound 2 Hydrochloride Salt Form 2 demonstrated that Compound 2 Hydrochloride Salt Form 1 is more stable than Compound 2 Hydrochloride Salt Form 2 in water at 23° C.

Preparation of Compound 2 Hydrochloride Salt, Form 1

Compound 2 (500 mg, 1.74 mmol) was added to 15.0 mL of methanol. The slurry was stirred and heated to 40° C. Hydrochloric acid (3M in water, 0.586 mL, 1.0 eq.) was added to the slurry at 40° C. The slurry was seeded with ~2 mg of Compound 2 HCl salt at 40° C. and stirred for 60 minutes, resulting in a thick slurry. The slurry was cooled from 40° C. to 25° C. and then stirred at 25° C. for 16 hours. The solids were isolated by vacuum filtration, rinsed and washed with ~5 mL methanol. The product was dried at 50° C. under vacuum for 3 hours to afford Compound 2 Hydrochloride salt Form 1 (510 mg, 91% yield) as a white crystalline powder.

Compound 2 Hydrochloride Salt Form 1 was characterized as follows:

i) PXRD: The PXRD diffractogram of Compound 2, Hydrochloride Salt, Form 1 is depicted in FIG. 24; the associated PXRD Peaks are listed in Table 20 (where * indicates ±0.2° and ** indicates the relative intensity for each peak is determined by normalizing its intensity to that of the strongest peak at 25.1° angle as 100).

TABLE 20

PXRD Peaks of Compound 2 Hydrochloride Salt Form 1

| Two-Theta Angle* (degree) | Relative Intensity** (arbitrary) |
|---|---|
| 6.0 | 63.3 |
| 9.5 | 6.9 |
| 10.8 | 37.1 |
| 12.0 | 6.3 |
| 12.7 | 82.4 |
| 17.2 | 5.8 |
| 17.5 | 12.3 |
| 18.1 | 99.3 |
| 19.1 | 25.4 |
| 20.2 | 65.0 |
| 25.1 | 100.0 |
| 25.4 | 42.7 |
| 25.7 | 22.4 |
| 26.4 | 8.1 |
| 28.1 | 11.0 | ii) FTIR: The FTIR Spectrum of Compound 2, Hydrochloride Salt, Form 1 is depicted in FIG. 25; the associated FTIR Peaks are listed in Table 21.

TABLE 21

FTIR Peaks of Compound 2 Hydrochloride Salt Form 1

Figure 26:
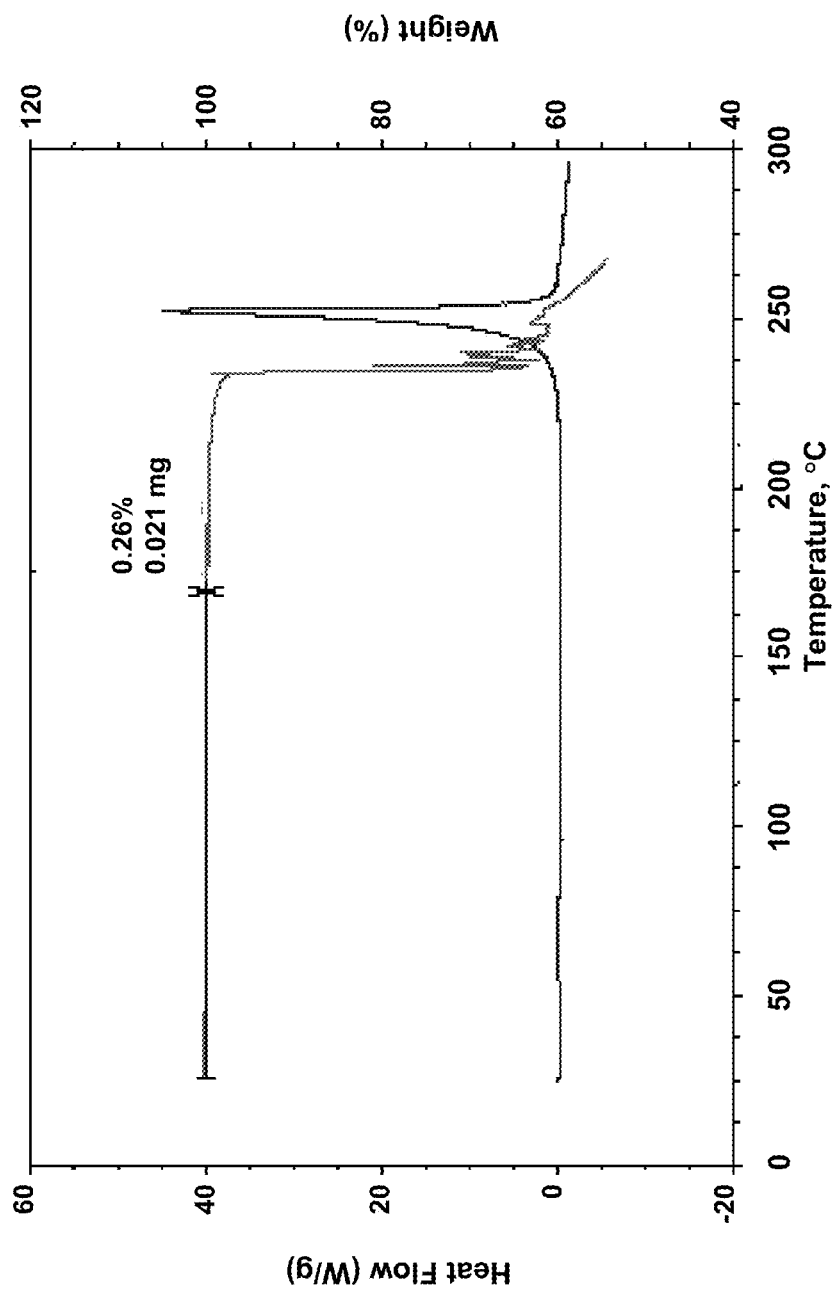
FIG. 26: DSC/TGA Analysis of N-methyl-1-(5-(thiophen-2-yl)tetrazolo[1,5-a]pyrazin-8-yl)azetidin-3-amine Hydrochloride Form 1, also known as Compound 2 Hydrochloride Salt Form 1.

| Position (cm$^{-1}$) | Intensity |
|---|---|
| 605.9 | 0.08 |
| 632.1 | 0.15 |
| 675.6 | 0.10 |
| 692.0 | 0.11 |
| 714.9 | 0.37 |
| 849.7 | 0.14 |
| 898.4 | 0.11 |
| 1011.5 | 0.10 |
| 1075.0 | 0.13 |
| 1196.2 | 0.15 |
| 1281.9 | 0.12 |
| 1420.8 | 0.17 |
| 1477.9 | 0.08 |
| 1492.5 | 0.11 |
| 1551.2 | 0.39 |
| 1590.1 | 0.13 |
| 2447.9 | 0.08 |
| 2689.3 | 0.14 | iv) DSC/TGA: The DSC scan Compound 2, Hydrochloride Salt, Form 1 is depicted in FIG. 26. Compound 2 Hydrochloride Form 1 exhibits no endothermic melting event before the apparent exothermic decomposition near 250° C. TGA indicates negligible weight loss below 200° C.

SCHEME 4

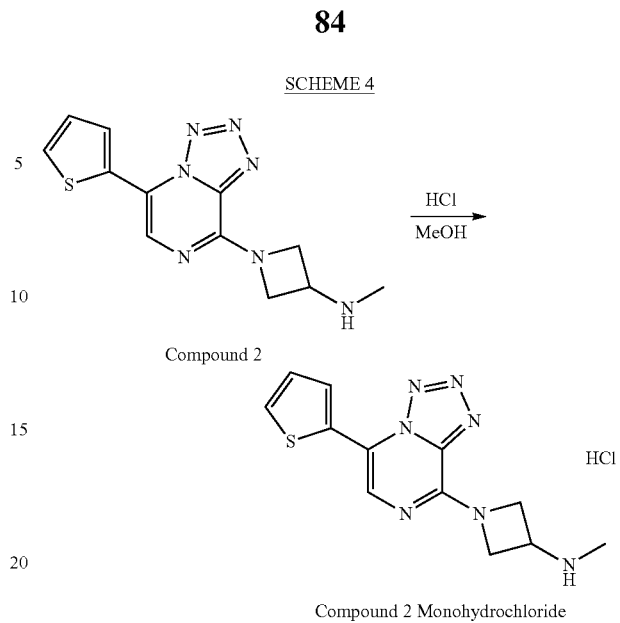

Compound 2

Compound 2 Monohydrochloride

Alternative Preparation of Compound 2, Hydrochloride Salt, Form 1

N-methyl-1-(5-(thiophen-2-yl)tetrazolo[1,5-a]pyrazin-8-yl)azetidin-3-amine (Compound 2, 5.0 g, 17.40 mmol) was added methanol (150 mL) and the slurry was stirred at room temperature. Aqueous hydrochloric acid (3M in water, 5.8 mL, 1.0 eq.) was added, and the slurry was seeded with ~2 mg of Compound 2, Hydrochloric Salt, Form 1 resulting in a thick slurry which was stirred for 3 hours at 25° C. The product was isolated by vacuum filtration, washed with methanol (~15 mL) and dried at 50° C. under vacuum for 3 hours to afford Compound 2, Hydrochloride Salt, Form 1 (4.9 g, 92% yield).

Characterization of Compound 2 Hydrochloride Salt Form 2

Figure 27:
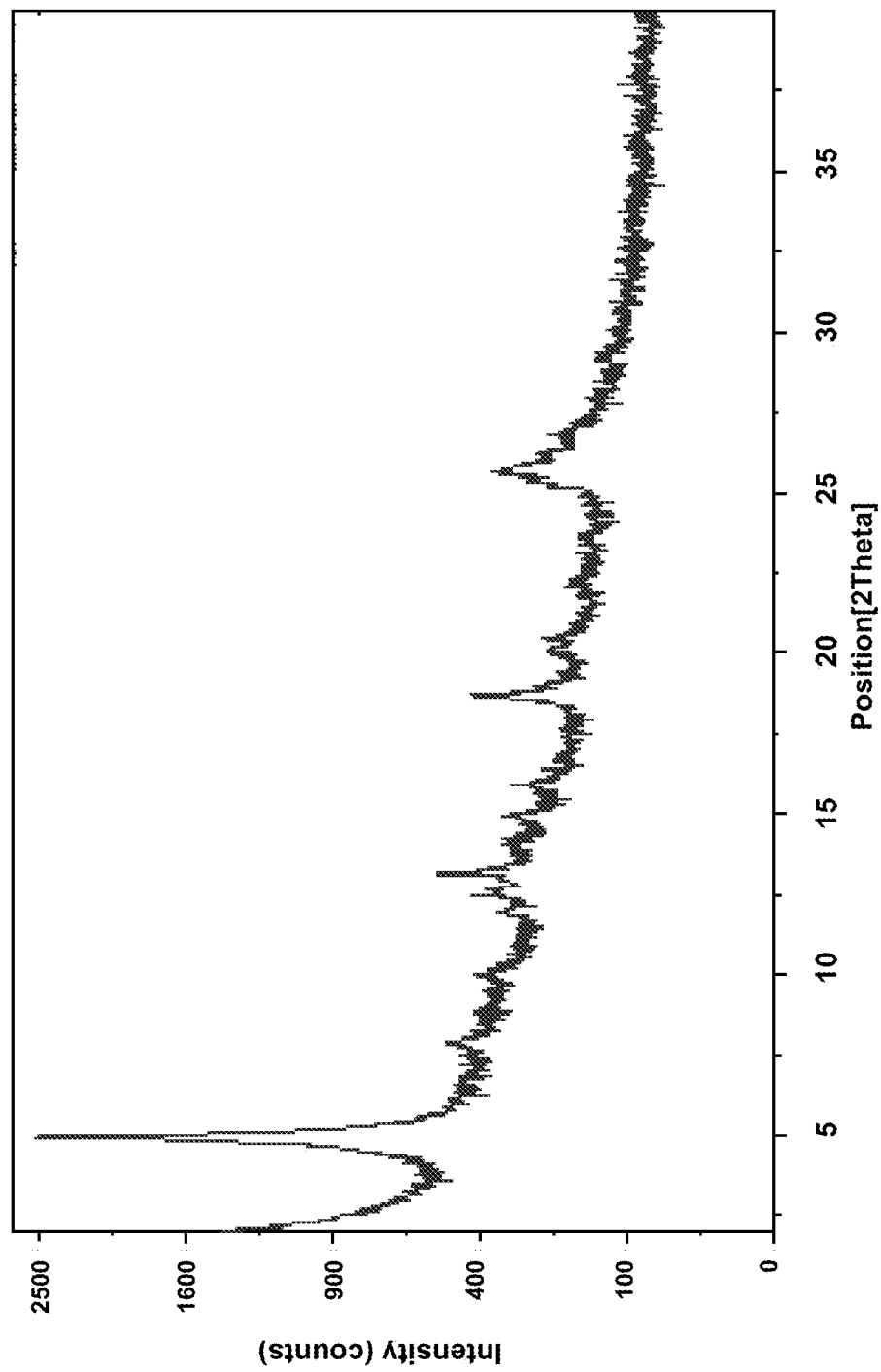
FIG. 27: PXRD diffractogram of N-methyl-1-(5-(thiophen-2-yl)tetrazolo[1,5-a]pyrazin-8-yl)azetidin-3-amine Hydrochloride Form 2, also known as Compound 2 Hydrochloric Salt Form 2.

Compound 2 Hydrochloride Salt Form 2 was characterized as follows:

i) PXRD: The PXRD diffractogram of Compound 2, Hydrochloride Salt, Form 2 is depicted in FIG. 27; the associated PXRD Peaks are listed in Table 22 (where * indicates ±0.2° and ** indicates the relative intensity for each peak is determined by normalizing its intensity to that of the strongest peak at 25.1° angle as 100).

TABLE 22

PXRD Peaks of Compound 2 Hydrochloride Salt Form 2
PXRD Peaks of
Compound 2 Hydrochloride Form 2

Figure 28:
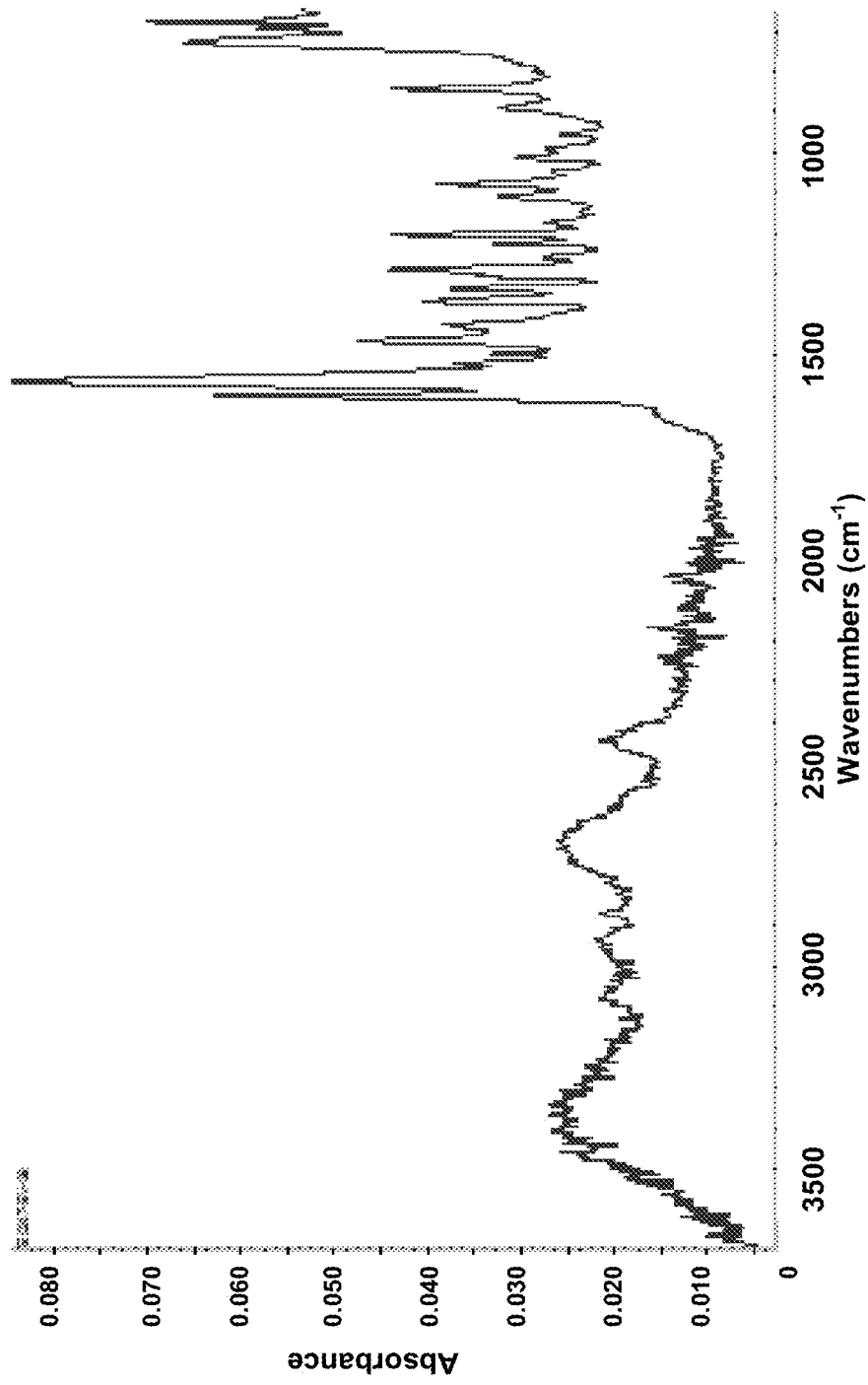
FIG. 28: FTIR Spectrum of N-methyl-1-(5-(thiophen-2-yl)tetrazolo[1,5-a]pyrazin-8-yl)azetidin-3-amine Hydrochloride Form 2, also known as Compound 2 Hydrochloride Salt Form 2.

| Two-Theta Angle* (degree) | Relative Intensity** (arbitrary) |
|---|---|
| 5.0 | 100 |
| 13.2 | 10.9 |
| 28.7 | 11.2 |
| 25.6 | 7.5 | ii) FTIR: The FTIR Spectrum of Compound 2 Hydrochloride Salt Form 2 is depicted in FIG. 28; the associated FTIR Peaks are listed in Table 23.

TABLE 23

FTIR Peaks of Compound 2 Hydrochloride Salt Form 2
FTIR Peaks of
Compound 2 Hydrochloride Form 2

| Position (cm$^{-1}$) | Intensity |
|---|---|
| 841.5 | 0.044 |
| 1076.6 | 0.039 |
| 1201.4 | 0.044 |
| 1287.6 | 0.044 |
| 1335.3 | 0.037 |
| 1365.2 | 0.040 |
| 1421.9 | 0.038 |
| 1464.1 | 0.047 |
| 1520.1 | 0.037 |
| 1562.9 | 0.085 |
| 1598.1 | 0.063 |

Compound 2 Mesylate Salt

Crystallization experiments targeting the preparation of Compound 2 Mesylate Salt were conducted in which the effect of solvent (acetone, acetonitrile, tetrahydrofuran, methanol, isopropyl alcohol, water/1% DMSO, ethyl acetate, dichloromethane, MTBE, Toluene, MIBK and dioxane) and crystallization methods (temperature cycling, evaporation) were surveyed.

Two crystal forms of Compound 2 Mesylate salt were obtained from these experiments. Compound 2 Mesylate Salt, Form 1 is a non-solvated, monomesylate solid state form that was obtained from nine of twelve crystallization experiments. Compound 2 Mesylate Salt Form 1 exhibits good physical properties and high aqueous solubility (>100 mg/ml). Compound 2 Mesylate Salt Form 2 is a hydrate that was obtained by slow evaporation of gummy solids at ambient temperature in two of twelve screening experiments. Several attempts to reproduce Compound 2 Mesylate Salt Form 2 were unsuccessful and produced Compound 2 Mesylate Salt, Form 1 instead.

A competitive ripening experiment was conducted between Compound 2 Mesylate Salt Form 1 and Compound 2 Mesylate Salt, Form 2 indicated that Form 1 is more stable than Form 2 in acetone/10% water at 23° C.

Preparation of Compound 2 Mesylate Salt, Form 1

Compound 2 (500 mg, 1.74 mmol) was added to 15 mL of acetonitrile. The slurry was stirred and heated to 40° C. Mesic acid (3M in water, 0.586 mL, 1.0 eq.) was added to the slurry at 40° C. The solution was seeded with ~2 mg of Compound 2 Mesylate Salt, Form 1 at 40° C. and stirred for 60 minutes resulting in a thick slurry. The slurry was cooled from 40° C. to 25° C. and then stirred at 25° C. for 16 hours. The solids were isolated by vacuum filtration, rinsed and washed with 5 mL acetonitrile. The product was dried at 50° C. under vacuum for 3 hours to afford Compound 2 Mesylate Salt, Form 1 (590 mg, 88% yield).

Compound 2 Mesylate Salt Form 1 was characterized as follows:

i) $^1$H NMR: (500 MHz, DMSO-d$_6$) δ: 9.21 (s, 2H), 8.29 (s, 1H), 8.031, 8.03 (d, J=3.0 Hz, 1H), 7.30, 7.29 (ABq, J$_{AB}$=4 Hz, 1H), 4.69 (brd, J=92.5 Hz, 3.75H), 4.29 (m, 1H), 2.68 (s, 3H), 2.33 (s, 3H)* (where * indicates 1H integration confirms Compound 2:Mesylate stoichiometry to be 1:1).

ii) PXRD: The PXRD diffractogram of Compound 2, Mesylate Salt, Form 1 is depicted in FIG. 29; the associated PXRD Peaks are listed in Table 24 (where * indicates ±0.2°, ** indicates the relative intensity for each peak is determined by normalizing its intensity to that of the strongest peak at 15.0° angle as 100).

TABLE 24

PXRD Peaks of Compound 2 Mesylate Salt Form 1
PXRD Peaks of
Compound 2 Mesylate Form 1 (Anhydrous)

| Two-Theta Angle* (degree) | Relative Intensity** (arbitrary) |
|---|---|
| 11.6 | 31.6 |
| 12.1 | 7.7 |
| 15.0 | 100.0 |
| 15.4 | 6.7 |
| 16.5 | 10.5 |
| 17.0 | 6.6 |
| 17.4 | 9.0 |
| 17.7 | 27.6 |
| 18.7 | 14.0 |
| 19.6 | 18.2 |
| 21.0 | 23.0 |
| 22.3 | 6.2 |
| 23.3 | 8.3 |
| 24.1 | 18.2 |
| 24.3 | 22.0 |
| 25.2 | 31.9 |
| 28.7 | 14.1 |
| 30.5 | 7.1 | iii) FTIR: The FTIR Spectrum of Compound 2, Mesylate Salt, Form 1 is depicted in FIG. 30; the associated FTIR Peaks are listed in Table 25.

TABLE 25

FTIR Peaks of Compound 2 Mesylate Salt Form 1
FTIR Peaks of
Compound 2 Mesylate Form 1 (Anhydrous)

Figure 31:
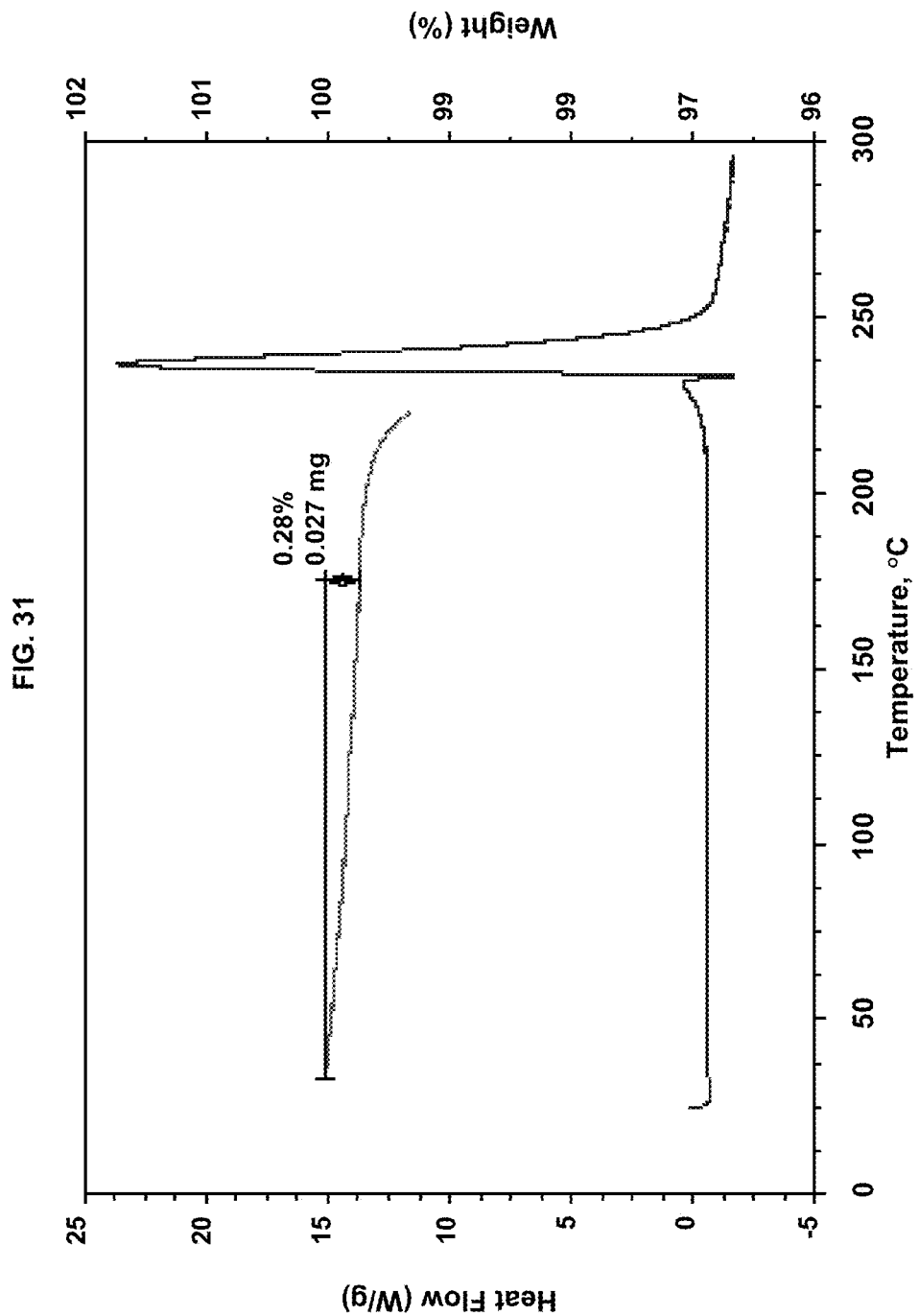
FIG. 31: DSC/TGA Analysis of N-methyl-1-(5-(thiophen-2-yl)tetrazolo[1,5-a]pyrazin-8-yl)azetidin-3-amine Mesylate Form 1, also known as Compound 2 Mesylate Salt Form 1.
Figure 32:
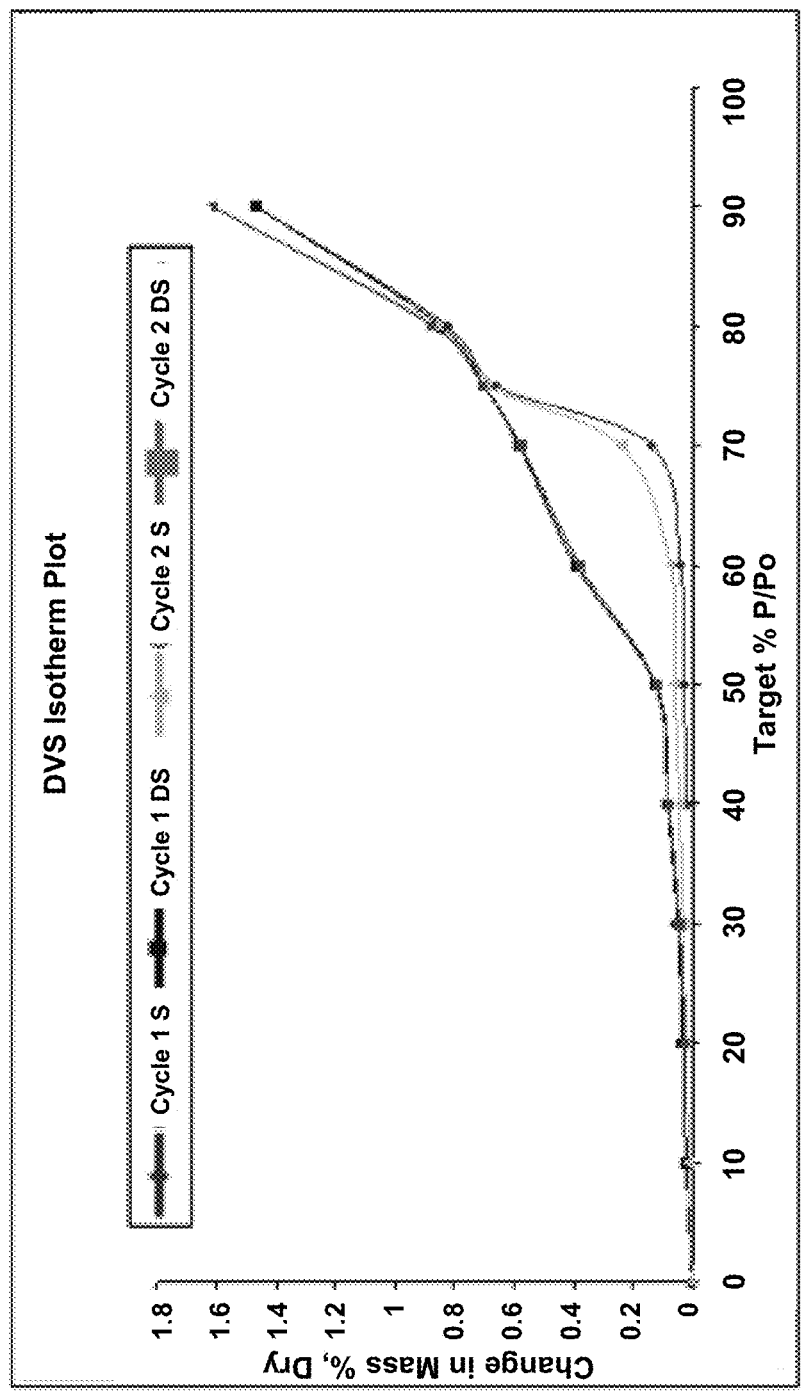
FIG. 32: GVS Isotherm Plot of N-methyl-1-(5-(thiophen-2-yl)tetrazolo[1,5-a]pyrazin-8-yl)azetidin-3-amine Mesylate Form 1, also known as Compound 2 Mesylate Salt Form 1. The last two data points of cycle 2 desorption were aberrant due to balance failure and not plotted.

| Position (cm$^{-1}$) | Intensity |
|---|---|
| 733.1 | 0.34 |
| 781.0 | 0.22 |
| 840.8 | 0.13 |
| 1008.1 | 0.16 |
| 1038.4 | 0.43 |
| 1079.7 | 0.15 |
| 1139.9 | 0.26 |
| 1199.0 | 0.30 |
| 1330.2 | 0.11 |
| 1461.2 | 0.17 |
| 1518.1 | 0.12 |
| 1556.6 | 0.33 |
| 1603.5 | 0.17 | iv) DSC/TGA: The DSC/TGA scans Compound 2 Mesylate Salt Form 1 is depicted in FIG. 31. The DSC curve showed no evidence for melting before decomposition at approximately 230° C. TGA showed a loss of 0.3% between 25° C. and 175° C.

v) GVS: The GVS isotherm plot for Compound 2, Mesylate Salt Form 1 is depicted in FIG. 32. Water content remained relatively constant between 0-50% RH. Above 50% RH there was a small increase in weight reaching 1.6% at 90% RH. FTIR analysis of the sample before and after GVS confirmed that there was no change in crystal form.

Equilibrium Solubility Studies of Compound 2 Citrate Form 1, Compound 2 Hydrochloride Form 1 and Compound 2 Mesylate Form 1

Equilibrium solubility experiments were conducted for Compound 2 Monohydrochloride Form 1, Compound 2 Monomesylate Form 1 and Compound 2 Monocitrate Form 1 salts in water and pH-5 acetate buffer solution. The results of the equilibrium solubility study are summarized in Table 26 (where "a" indicates FTIR and PXRD spectra of both samples were distinctly different from the known forms of Compound 2 or Compound 2 Monocitrate salt Form 1).

TABLE 26

Equilibrium Solubility of Compound 2 Citrate Form 1, Compound 2 Hydrochloride Form 1 and Compound 2 Mesylate Form 1

| Salt | Salt Weight (mg) | Solvent | Sol-vent (mL) | Resid-ual Solid | Final pH | Concen-tration (mg/mL) |
|---|---|---|---|---|---|---|
| Citrate Form 1 | 25.5 | Water | 1.0 | New Form[a] | 3.41 | 3.4 |
| Citrate Form 1 | 25.6 | 0.2M Acetate Buffer (pH5) | 1.0 | New Form[a] | 4.41 | 1.5 |
| HCl Form 1 | 50.2 | Water | 0.5 | HCl salt Form 1 | 4.93 | 18.1 |
| HCl Form 1 | 50.3 | 0.2M Acetate Buffer (pH5) | 0.5 | HCl salt Form 1 | 4.81 | 21.6 |
| Mesylate Form 1 | 50.1 | Water | 0.5 | None | 4.68 | >100 |
| Mesylate Form 1 | 50.4 | 0.2M Acetate Buffer (pH5) | 0.5 | None | 4.76 | >100 |

Compound 2 Citrate salt (New Form) had solubility values of 3.4 and 1.5 mg/mL in water and in pH 5 buffer, respectively. FTIR spectra of the residual solids from these two experiments were each unique, and were different from the known forms of Compound 2 or Compound 2 Citrate salt.

Compound 2 Monohydrochloride salt Form 1 had solubility values of 18.1 and 21.6 mg/mL in water and 0.2M acetate buffer (pH5). The FTIR spectra of the residual solids from these two experiments matched the reference spectra for Compound 2 Hydrochloride Salt Form 1.

In the case of Compound 2 Mesylate salt Form 1 no residual solids were isolated; the sample completely dissolved. The equilibrium solubility of Compound 2 Mesylate salt Form 1 is >100 mg/mL in water and in 0.2M acetate buffer (pH5).

In Vitro Biological Activity

The activity of the compounds in Examples 1-2 as $H_4R$ inhibitors is illustrated in the following assays. Similar compounds have activity in these assays as well.

In vitro Histamine Receptor Cell-Based Assays

The cell-based assays utilize an aequorin dependent bioluminescence signal. Doubly-transfected, stable CHO-K1 cell lines expressing human $H_4$, or $H_1$, mitochondrion-targeted aequorin, and ($H_4$ only) human G protein $G\alpha16$ are obtained from Perkin-Elmer. Cells are maintained in F12 (Ham's) growth medium, containing 10% (vol./vol.) fetal bovine serum, penicillin (100 IU/mL), streptomycin (0.1 mg/mL), zeocin (0.25 mg/mL) and geneticin (0.40 mg/mL). Cell media components are from Invitrogen, Inc. One day prior to assay, the growth medium is replaced with the same, excluding zeocin and geneticin. In some assays, cells previously frozen at "ready to use density" are thawed and immediately available for loading with coelenterazine-h dye as described below.

For assay preparation, growth medium is aspirated, and cells are rinsed with calcium-free, magnesium-free phosphate-buffered saline, followed by two to three minute incubation in Versene (Invitrogen, Inc.) at 37° C. Assay medium (DMEM:F12 [50:50], phenol-red free, containing 1 mg/mL protease-free bovine serum albumin) is added to collect the released cells, which are then centrifuged. The cell pellet is re-suspended in assay medium, centrifuged once more, and re-suspended in assay medium to a final density of $5\times10^6$ cells/mL. Coelenterazine-h dye (500 μM in ethanol) is added to a final concentration of 5 μM, and mixed immediately. The conical tube containing the cells is then wrapped with foil to protect the light-sensitive dye. The cells are incubated for four hours further at room temperature (approximately 21° C.) with end-over-end rotation to keep them in suspension.

Just before assay, the dye-loaded cells are diluted to $1.5\times10^6$ cells/mL ($H_4$ receptor) or $0.75\times10^6$ cells/mL ($H_1$ receptor) with additional assay medium. Cells are dispensed to 1536 well micro-titer plates at 3 μL/well. To assay receptor antagonism 60 nl of 100× concentration test compounds in 100% dimethyl sulfoxide (DMSO) are dispensed to the wells, one compound per well in concentration response array by passive pin transfer, and the plates are incubated for 15 minutes at room temperature. Assay plates are then transferred to a Lumilux bioluminescence plate reader (Perkin-Elmer) equipped with an automated 1536 disposable tip pipette. The pipette dispenses 3 μL/well of agonist (histamine, at twice the final concentration, where final concentration is a previously determined $EC_{80}$) in assay medium, with concurrent bioluminescence detection. Potential agonist activity of test compounds is measured by separate assays that measure response to test compounds alone, without added histamine agonist. CCD image capture on the Lumilux includes a 5 second baseline read and generally a 40 second read per plate after agonist (or test compound only in agonist mode assay) addition. A decrease in bioluminescence signal (measured either as area-under-the-curve, or maximum signal amplitude minus minimum signal amplitude) correlates with receptor antagonism in a dose dependent manner. The negative control is DMSO lacking any test compound. For antagonist assays, the positive controls are JNJ7777120 (1-[(5-Chloro-1H-indol-2-yl)carbonyl]-4-methyl-piperazine, 10 μM final concentration, $H_4$ receptor) and diphenhydramine (2-Diphenylmethoxy-N,N-dimethylethylamine, 10 μM final concentration, $H_1$ receptor). For agonist assays, the positive control is histamine (10 μM final concentration). Efficacy is measured as a percentage of positive control activity.

TABLE 27

| | Biological Activity | |
|---|---|---|
| Example No. | H4 Antagonist EC50, "+" indicates ≤10 µM, "−" indicates >10 µM | H4 Agonist EC50, "NA" indicates no activity to 100 µM "NT" indicates not tested |
| 1 | + | NA |
| 2 | + | NA |

In Vivo Activity

Assessment of H₄ Antagonism—Model of Allergic Rhinits in Balb/C Mice.

Animals.

Female BALB/c mice, 6-12 weeks of age, were obtained from Jackson Laboratories (Bar Harbor, Me.). All experimental animals used in this work were under a protocol approved by the Institutional Animal Care and Use Committee of the National Jewish Medical and Research Center, Denver, Colo.

Induction and Measurement of Allergic Rhinitis.

The assay protocol is similar to that described in Miyahara, S. et al. (2005), *J Allergy Clin Immunol.*, 116:1020-1027. The role of the H4 receptor in this model has been validated [Shiraishi, Y. et al. (2009), *J Allergy Clin Immunol.*, 123:556]. Briefly, mice received intraperitoneal injections of 20 µg ovalbumin (OVA, Grade V; Sigma-Aldrich, St. Louis, Mo.), previously emulsified in 2.25 mg of alum (AlumImuject; Pierce, Rockford, Ill.) in a total volume of 100 µL (sensitization phase). Injections occurred on days 0 and 14. Starting on day 28 onward (challenge phase), mice received daily intranasal instillation of OVA (25 mg/ml in phosphate-buffered saline), 15 µl in each nostril without anesthesia. Installations occurred for 6 days to evoke allergic nasal inflammation and congestion. Compounds were tested for the ability to prevent induction of nasal inflammation and congestion by intranasal instillation 2.5 hours prior to OVA instillation. Instillations of compounds were performed using 10 µl (0.1% weight/volume [1 mg/ml]) in each nostril without anesthesia, in formulation vehicle: either (a) unbuffered saline, [pH approximately 6.0], 0.2% volume/volume Tween-80 (Sigma-Aldrich, St. Louis, Mo.), or (b) 50 mM sodium acetate [pH 5.0], 100 mM sodium chloride, 0.2% volume/volume Tween-80. On day 4 (early phase) and day 7 (late phase) after starting OVA challenges, respiratory frequency (RF) was measured in conscious animals by single chamber restrained whole-body plethysmography (WBP) [Buxco Research Systems, Troy, N.Y.]. Because mice are obligate nasal breathers, OVA induced nasal inflammation and congestion results in decreased breathing frequency. Compounds that block OVA-induced nasal inflammation and congestion prevent the decrease in RF compared to positive control (instillation with formulation vehicle only prior to OVA challenge). The assay negative control measures baseline RF, where challenge is performed with phosphate-buffered saline lacking OVA. After whole-body plethysmography on day 7, nasal airflow impedance was measured as described ($R_{NA}$, see Methods section for Miyahara S. et al. [above] in the online supplemental material at the Journal of Allergy and Clinical Immunology: www.jacionline.org), using a custom-designed ventilator (Flexivent; Scireq, Montreal, Quebec, Canada). After airflow impedance measurement, the study was terminated and animals were euthanized.

It is expected that many of these compounds when tested will be active and will have utility similar to those that have been tested. In Table 28 below, entries with a "+" are active and statistically significant compared to positive control (based on standard error of the mean). Entries with a "−" are either weakly active, or inactive (statistically indistinguishable from positive control).

TABLE 28

| | In Vivo Activity | |
|---|---|---|
| Example # | Dosage | WBP, Day 4 +: increase in RF over positive control −: no increase in RF over positive control |
| 1 | 0.1%, w/v | + |
| 2 | 0.1%, w/v | + |

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound which is a salt, hydrate, or polymorph of structural Formula (XII)

(XII)

wherein:
  $X^8$ is chosen from CH and N;
  m and n are each an integer chosen from 1 and 2, and m=n;
  $R^{24}$ is chosen from lower amino, lower alkylamino, and lower alkyl;
  Y is chosen from a counterion and null; and
  Z is a chosen from a hydrate and null.

2. The compound as recited in claim 1, wherein:
  $X^8$ is N;
  m and n are each 2; and
  $R^{24}$ is lower alkyl.

3. The compound as recited in claim 2, wherein the compound is a salt, hydrate, or polymorph of 8-(4-Methylpiperazin-1-yl)-5-(thiophen-2-yl)tetrazolo[1,5-a]pyrazine.

4. The compound as recited in claim 1, wherein:
  $X^8$ is CH;
  m and n are each 1; and
  $R^{24}$ is chosen from lower amino and lower alkylamino.

5. The compound as recited in claim 4, wherein $R^{24}$ is lower alkylamino.

6. The compound as recited in claim 5, wherein the compound is a salt, hydrate, or polymorph of N-methyl-1-(5-(thiophen-2-yl)tetrazolo[1,5-a]pyrazin-8-yl)azetidin-3-amine.

7. The compound as recited in claim 1, wherein:
Y is a counterion, if the compound of Formula XII is a salt, or
Y is chosen from a counterion and null, if the compound of Formula XII is a polymorph.

8. The compound as recited in claim 7, wherein Y is a counterion and the compound is a salt.

9. The salt as recited in claim 8, or a polymorph or hydrate thereof, wherein Y is a counterion chosen from acetate, citrate, sulfate, phosphate, hydrochloride, aspartate, mesylate, malate, tartrate, stearate, and succinate.

10. The salt as recited in claim 9, or a polymorph or hydrate thereof, wherein the counterion is chosen from tartrate, mesylate, citrate, and hydrochloride.

11. The salt as recited in claim 10, wherein Z is chosen from a stoichiometric hydrate and a nonstoichiometric hydrate, or a polymorph thereof.

12. The salt as recited in claim 10, wherein Z is chosen from a monohydrate and a hemihydrate.

13. The salt as recited in claim 10, having structural Formula (XIII)

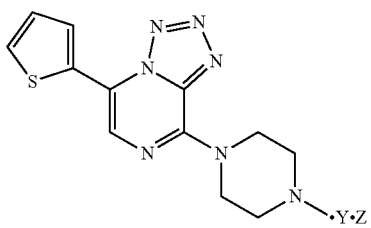

(XIII)

or a polymorph or hydrate thereof, wherein:
Y is a counterion chosen from tartrate and mesylate; and
Z is a chosen from a monohydrate, a hemihydrate, and null.

14. The salt as recited in claim 13, which is 8-(4-methylpiperazin-1-yl)-5-(thiophen-2-yl)tetrazolo[1,5-a]pyrazine mesylate, or a hydrate or polymorph thereof.

15. The hydrate of the salt as recited in claim 14, which is 8-(4-methylpiperazin-1-yl)-5-(thiophen-2-yl)tetrazolo[1,5-a]pyrazine mesylate monohydrate, or a polymorph thereof.

16. The polymorph of the hydrate as recited in claim 15, which is 8-(4-methylpiperazin-1-yl)-5-(thiophen-2-yl)tetrazolo[1,5-a]pyrazine mesylate monohydrate Form 1.

17. The polymorph as recited in claim 13, which is 8-(4-methylpiperazin-1-yl)-5-(thiophen-2-yl)tetrazolo[1,5-a]pyrazine mesylate Form 3.

18. The salt as recited in claim 13, which is 8-(4-methylpiperazin-1-yl)-5-(thiophen-2-yl)tetrazolo[1,5-a]pyrazine tartrate, or a hydrate or polymorph thereof.

19. The polymorph of the salt as recited in claim 18, which is 8-(4-methylpiperazin-1-yl)-5-(thiophen-2-yl)tetrazolo[1,5-a]pyrazine tartrate hemihydrate (Form 1).

20. The polymorph of the salt as recited in claim 18, which is 8-(4-methylpiperazin-1-yl)-5-(thiophen-2-yl)tetrazolo[1,5-a]pyrazine tartrate monohydrate (Form 2).

21. The salt has recited in claim 10, having structural Formula (XIV)

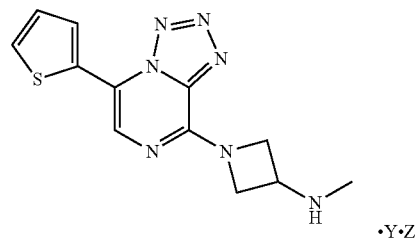

(XIV)

or a polymorph or hydrate thereof, wherein:
Y is a counterion chosen from citrate, hydrochloride, mesylate; and
Z is a chosen from a monohydrate, a hemihydrate, and null.

22. The salt as recited in claim 21, which is N-methyl-1-(5-(thiophen-2-yl)tetrazolo[1,5-a]pyrazin-8-yl)azetidin-3-amine citrate, or a hydrate or polymorph thereof.

23. The polymorph of the salt as recited in claim 22, which is N-methyl-1-(5-(thiophen-2-yl)tetrazolo[1,5-a]pyrazin-8-yl)azetidin-3-amine citrate Form 1.

24. The salt as recited in claim 21, which is N-methyl-1-(5-(thiophen-2-yl)tetrazolo[1,5-a]pyrazin-8-yl)azetidin-3-amine hydrochloride, or a hydrate or polymorph thereof.

25. The polymorph of the salt as recited in claim 24, which is N-methyl-1-(5-(thiophen-2-yl)tetrazolo[1,5-a]pyrazin-8-yl)azetidin-3-amine hydrochloride Form 1.

26. The salt as recited in claim 21, which is, N-methyl-1-(5-(thiophen-2-yl)tetrazolo[1,5-a]pyrazin-8-yl)azetidin-3-amine mesylate, or a hydrate or polymorph thereof.

27. The polymorph of the salt as recited in claim 26, which is N-methyl-1-(5-(thiophen-2-yl)tetrazolo[1,5-a]pyrazin-8-yl)azetidin-3-amine mesylate Form 1.

28. The compound as recited in claim 1 which forms a crystalline solid which has a solubility, in aqueous media at about pH 3.5 to about pH 5.0, of at least 2.5 mg/mL.

29. The compound as recited in claim 28, which has a solubility, in aqueous media at about pH 3.5 to about pH 5.0, of at least 5.0 mg/mL.

30. The compound as recited in claim 29, which has a solubility, in aqueous media at about pH 3.5 to about pH 5.0, of at least 10.0 mg/mL.

31. The compound as recited in claim 30, which has a solubility, in aqueous media at about pH 3.5 to about pH 5.0, of at least 20.0 mg/mL.

32. The compound as recited in claim 31, which has a solubility, in aqueous media at about pH 3.5 to about pH 5.0, of at least 30.0 mg/mL.

33. The compound as recited in claim 1, wherein the compound is a polymorph and Y is null.

34. The polymorph as recited in claim 33, which is a polymorph of 8-(4-methylpiperazin-1-yl)-5-(thiophen-2-yl)tetrazolo[1,5-a]pyrazine.

35. The polymorph as recited in claim 33, which is a polymorph of N-methyl-1-(5-(thiophen-2-yl)tetrazolo[1,5-a]pyrazin-8-yl)azetidin-3-amine.

36. The compound 8-(4-Methylpiperazin-1-yl)-5-(thiophen-2-yl)tetrazolo[1,5-a]pyrazine Tartrate Hemihydrate, having the structural formula (XV)

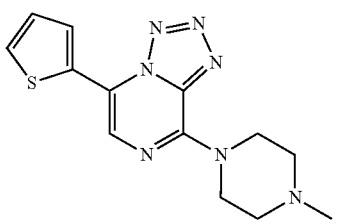

(XV)

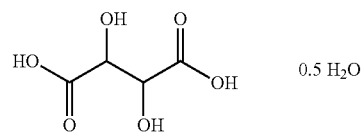

0.5 H₂O in a crystalline form.

37. The crystalline form of the compound as recited in claim 36, characterized in that said form has at least one of the following characteristics:
   a) an X-ray powder diffraction pattern with peaks at 10.2, 13.4, 17.4, 18.1, 23.5 and 26.0 degrees two theta (±0.2 degree) (CuKα λ=1.54059 A), or an X-ray powder diffraction pattern substantially in accordance with that shown in FIG. 1; and
   b) an FT-Raman spectrum with the bands at 1339, 1356, 1524 and 1589 cm⁻¹ or an FT-Raman spectrum substantially in accordance with that shown in FIG. 2.

38. The compound 8-(4-Methylpiperazin-1-yl)-5-(thiophen-2-yl)tetrazolo[1,5-a]pyrazine Tartrate Monohydrate, having the structural formula (XVI)

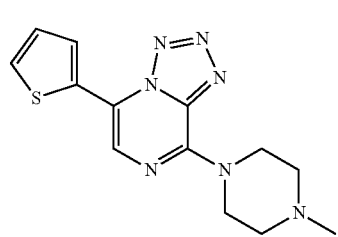

(XVI)

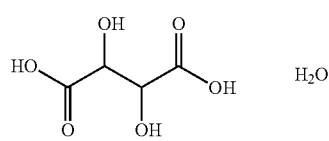

H₂O in a crystalline form.

39. The crystalline form of the compound as recited in claim 38, characterized in that said form has at least one of the following characteristics:
   a) an X-ray powder diffraction pattern with peaks at 11.4, 16.2, 17.1 19.0, 23.8 and 24.1 degrees two theta (±0.2 degree) (CuKα λ=1.54059 A), or an X-ray powder diffraction pattern substantially in accordance with that shown in FIG. 5; and
   b) an FT-Raman spectrum with the bands at 1350, 1422, 1494, 1522 and 1593 cm⁻¹ or an FT-Raman spectrum substantially in accordance with that shown in FIG. 6.

40. The compound 8-(4-Methylpiperazin-1-yl)-5-(thiophen-2-yl)tetrazolo[1,5-a]pyrazine Mesylate Monohydrate, having the structural formula (XVII)

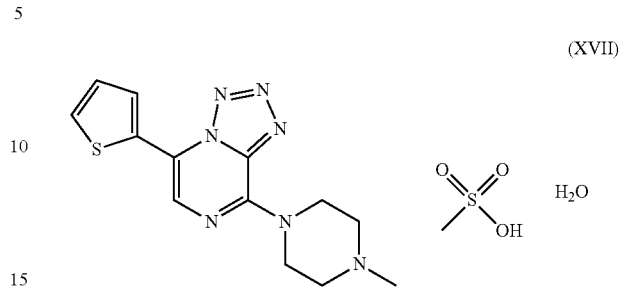

(XVII)

in crystalline form.

41. The crystalline form of the compound as recited in claim 40, characterized in that said form has at least one of the following characteristics:
   a) an X-ray powder diffraction pattern with peaks at 5.3, 10.5, 15.1, 20.4, 21.2, 21.8 and 23.0 degrees two theta (±0.2 degree) (CuKα λ=1.54059 A), or an X-ray powder diffraction pattern substantially in accordance with that shown in FIG. 9;
   b) an FT-Raman spectrum with the bands at 1299, 1313, 1354, 1422, 1494, 1523 and 1590 cm⁻¹ or an FT-Raman spectrum substantially in accordance with that shown in FIG. 10.

42. The compound 8-(4-Methylpiperazin-1-yl)-5-(thiophen-2-yl)tetrazolo[1,5-a]pyrazine Mesylate, having the structural formula (XVIII)

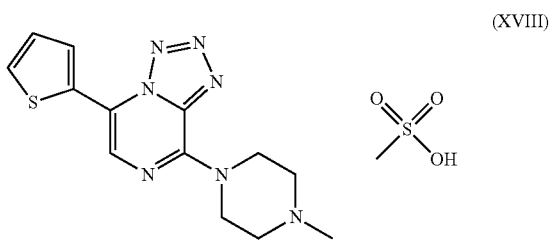

(XVIII)

in a crystalline form.

43. The crystalline form of the compound as recited in claim 42, characterized in that said form has at least one of the following characteristics:
   a) an X-ray powder diffraction pattern with peaks at 10.4, 16.3, 17.2, 17.8, 22.8, 24.0 and 27.8 degrees two theta (±0.2 degree) (CuKα λ=1.54059 A), or an X-ray powder diffraction pattern substantially in accordance with that shown in FIG. 17; and
   b) an FT-Raman spectrum with the bands at 1346, 1423, 1493, 1524 and 1589 cm⁻¹ or an FT-Raman spectrum substantially in accordance with that shown in FIG. 18.

44. The compound N-methyl-1-(5-(thiophen-2-yl)tetrazolo[1,5-a]pyrazin-8-yl)azetidin-3-amine Citrate, having the structural formula (XIX)

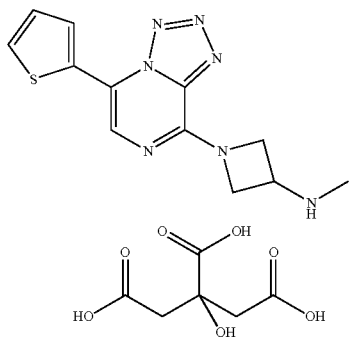

(XIX)

in a crystalline form.

45. The crystalline form of the compound as recited in claim 44, characterized in that said form has at least one of the following characteristics:
   a) an X-ray powder diffraction pattern with peaks at 9.4, 12.4, 18.9, 19.9, 26.2 and 28.6 degrees two theta (±0.2 degree) (CuKα λ=1.54059 A), or an X-ray powder diffraction pattern substantially in accordance with that shown in FIG. 20; and
   b) an FTIR spectrum with the bands at 731, 844, 1110, 1199, 1209, 1310, 1448 and 1564 cm$^{-1}$ or an FTIR spectrum substantially in accordance with that shown in FIG. 21.

46. The compound N-methyl-1-(5-(thiophen-2-yl)tetrazolo[1,5-a]pyrazin-8-yl)azetidin-3-amine Hydrochloride, having the structural formula (XX)

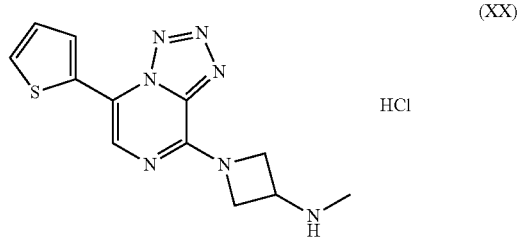 [SMILES: CNC1CN(c2ncc(-c3cccs3)n3nnnc23)C1 ; Cl]

(XX)

in a crystalline form.

47. The crystalline form of the compound as recited in claim 46, characterized in that said form has at least one of the following characteristics:
   a) an X-ray powder diffraction pattern with peaks at 6.0, 10.8, 12.7, 18.1, 20.2, 25.1 and 25.4 degrees two theta (±0.2 degree) (CuKα λ=1.54059 A), or an X-ray powder diffraction pattern substantially in accordance with that shown in FIG. 24; and
   b) an FTIR spectrum with the bands at 632, 715, 850, 1196, 1421, 1551 and 2689 cm$^{-1}$ or an FTIR spectrum substantially in accordance with that shown in FIG. 25.

48. The compound N-methyl-1-(5-(thiophen-2-yl)tetrazolo[1,5-a]pyrazin-8-yl)azetidin-3-amine Mesylate, having the structural formula (XXI)

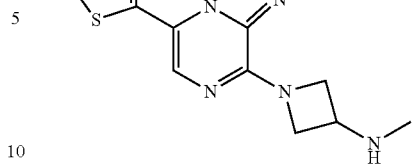

(XXI)

in a crystalline form.

49. The crystalline form of the compound as recited in claim 48, characterized in that said form has at least one of the following characteristics:
   a) an X-ray powder diffraction pattern with peaks at 11.6, 15.0, 17.7, 21.0, 24.3 and 25.2 degrees two theta (±0.2 degree) (CuKα λ=1.54059 A), or an X-ray powder diffraction pattern substantially in accordance with that shown in FIG. 29; and
   b) an FTIR spectrum with the bands at 733, 781, 1038, 1140, 1199 and 1557 cm$^{-1}$ or an FTIR spectrum substantially in accordance with that shown in FIG. 30.

50. A pharmaceutical composition comprising a compound as recited in claim 1, together with a pharmaceutically acceptable carrier.

51. The pharmaceutical composition as recited in claim 50, wherein the compound is chosen from a salt, polymorph or hydrate of 8-(4-methylpiperazin-1-yl)-5-(thiophen-2-yl)tetrazolo[1,5-a]pyrazine and a salt, polymorph or hydrate of N-methyl-1-(5-(thiophen-2-yl)tetrazolo[1,5-a]pyrazin-8-yl)azetidin-3-amine.

52. The pharmaceutical composition as recited in claim 51, wherein the compound is a salt and Y is chosen from tartrate, mesylate, citrate, and hydrochloride.

53. The pharmaceutical composition as recited in claim 52, comprising a salt, or a polymorph thereof, chosen from
   8-(4-methylpiperazin-1-yl)-5-(thiophen-2-yl)tetrazolo[1,5-a]pyrazine tartrate hemihydrate;
   8-(4-methylpiperazin-1-yl)-5-(thiophen-2-yl)tetrazolo[1,5-a]pyrazine tartrate monohydrate;
   8-(4-methylpiperazin-1-yl)-5-(thiophen-2-yl)tetrazolo[1,5-a]pyrazine mesylate monohydrate;
   N-methyl-1-(5-(thiophen-2-yl)tetrazolo[1,5-a]pyrazin-8-yl)azetidin-3-amine citrate;
   N-methyl-1-(5-(thiophen-2-yl)tetrazolo[1,5-a]pyrazin-8-yl)azetidin-3-amine hydrochloride; and
   N-methyl-1-(5-(thiophen-2-yl)tetrazolo[1,5-a]pyrazin-8-yl)azetidin-3-amine mesylate.

54. The pharmaceutical composition as recited in claim 53, comprising 8-(4-methylpiperazin-1-yl)-5-(thiophen-2-yl)tetrazolo[1,5-a]pyrazine mesylate monohydrate or a polymorph thereof.

55. The pharmaceutical composition as recited in claim 54, comprising 8-(4-methylpiperazin-1-yl)-5-(thiophen-2-yl)tetrazolo[1,5-a]pyrazine mesylate monohydrate Form 1.

56. The pharmaceutical composition as recited in claim 53, comprising N-methyl-1-(5-(thiophen-2-yl)tetrazolo[1,5-a]pyrazin-8-yl)azetidin-3-amine hydrochloride.

57. The pharmaceutical composition as recited in claim 56, comprising N-methyl-1-(5-(thiophen-2-yl)tetrazolo[1,5-a]pyrazin-8-yl)azetidin-3-amine hydrochloride Form 1.

58. The pharmaceutical composition as recited in claim 53, comprising N-methyl-1-(5-(thiophen-2-yl)tetrazolo[1,5-a]pyrazin-8-yl)azetidin-3-amine mesylate or a polymorph thereof.

59. The pharmaceutical composition as recited in claim 58, comprising N-methyl-1-(5-(thiophen-2-yl)tetrazolo[1,5-a]pyrazin-8-yl)azetidin-3-amine mesylate Form 1.

* * * * *